(12) United States Patent
Kobold et al.

(10) Patent No.: US 11,723,922 B2
(45) Date of Patent: Aug. 15, 2023

(54) CXCR6-TRANSDUCED T CELLS FOR TARGETED TUMOR THERAPY

(71) Applicant: LUDWIG-MAXIMILIANS-UNIVERSITÄT MÜNCHEN, Munich (DE)

(72) Inventors: Sebastian Kobold, Munich (DE); Stefan Endres, Munich (DE); Moritz Rapp, Zürich (CH); Simon Grassmann, Munich (DE)

(73) Assignee: LUDWIG-MAXIMILIANS-UNIVERSITÄT MÜNCHEN, Munich (DE)

( * ) Notice: Subject to any disclaimer, the term of this patent is extended or adjusted under 35 U.S.C. 154(b) by 467 days.

(21) Appl. No.: 15/768,301

(22) PCT Filed: Oct. 14, 2016

(86) PCT No.: PCT/EP2016/074644
§ 371 (c)(1),
(2) Date: Apr. 13, 2018

(87) PCT Pub. No.: WO2017/064222
PCT Pub. Date: Apr. 20, 2017

(65) Prior Publication Data
US 2018/0256645 A1    Sep. 13, 2018

(30) Foreign Application Priority Data
Oct. 16, 2015 (EP) .................................. 15190179

(51) Int. Cl.
| | |
|---|---|
| C12N 5/10 | (2006.01) |
| A61K 35/17 | (2015.01) |
| C07K 14/715 | (2006.01) |
| C12N 15/86 | (2006.01) |
| C07K 14/725 | (2006.01) |
| C07K 14/705 | (2006.01) |
| C12N 5/0783 | (2010.01) |
| C12N 5/16 | (2006.01) |
| C12N 15/85 | (2006.01) |
| A61P 35/00 | (2006.01) |
| A61K 39/00 | (2006.01) |

(52) U.S. Cl.
CPC .......... A61K 35/17 (2013.01); C07K 14/7051 (2013.01); C07K 14/70521 (2013.01); C07K 14/7158 (2013.01); C12N 5/0636 (2013.01); C12N 5/16 (2013.01); C12N 15/85 (2013.01); C12N 15/86 (2013.01); A61K 2039/5158 (2013.01); A61P 35/00 (2018.01); C12N 2510/00 (2013.01); C12N 2740/13043 (2013.01)

(58) Field of Classification Search
None
See application file for complete search history.

(56) References Cited

U.S. PATENT DOCUMENTS

2002/0076694 A1* 6/2002 Littman ................. A61K 39/39
435/5
2014/0271635 A1    9/2014 Brogdon et al.

FOREIGN PATENT DOCUMENTS

WO    2015028444 A1    3/2015

OTHER PUBLICATIONS

Blaak et al. (2005) J. Virology 79: 1686-1700.*
International Preliminary Report on Patentability to corresponding International Application No. PCT/EP2016/074644, dated Apr. 26, 2018 (10 pages).
Deng et al., "Expression Cloning of New Receptors used by Simian and Human Immunodeficiency Viruses," Nature, Nature Publishing Group, vol. 388, pp. 296-300 (1997).
Extended European Search Report to corresponding EP Application No. 15190179.0 dated Mar. 24, 2016 (11 pages).
International Search Report and Written Opinion to corresponding International Application No. PCT/EP2016/074644 dated Feb. 3, 2017 (17 pages).
Matsumura et al., "Radiation-Induced CXCL16 Released by Breast Cancer Cells Attracts Effector T Cells 1," The Journal of Immunology, pp. 3099-3107 (2008).
Sapoznik et al., "CXCR1 as a novel target for directing reactive T cells toward melanoma: implications for adoptive cell transfer immunotherapy," Cancer Immunology, Immunotherapy, vol. 61, No. 10, pp. 1833-1847 (2012).
Wennerberg et al., "CXCL10-induced migration of adoptively transferred human natural killer cells toward solid tumors causes regression of tumor growth in vivo," Cancer Immunology and Immunology, vol. 64, No. 2, pp. 225-235 (2014).
Xiao et al., "CXCL16/CXCR6 chemokine signaling mediates breast cancer progression by pERK1/2-dependent mechanisms," Oncotarget, vol. 6, No. 17, pp. 14165-14178 (2015).
Alkhatib et al., "A new SIV co-receptor, STRL33", Jul. 17, 1997, Nature, vol. 388, 1 page.
Schneider et al., "Characterization of EBV-Genome Negative "Null" and "T" Cell Lines Derived from Children with Acute Lymphoblastic Leukemia and Leukemic Transformed Non-Hodgkin Lymphoma", Int. J. Cancer : 19 (1977), pp. 621-626.
Jurkat, Clone E6-1, ATCC 2016, 6 pages. Copyright 2016.

* cited by examiner

Primary Examiner — Michael D Pak
(74) Attorney, Agent, or Firm — Jonathan D. Ball; Greenberg Traurig, LLP

(57) ABSTRACT

The present invention relates to CXCR6-transduced (a) T cell(s) such as (a) CD8+ T cell(s), (a) CD4+ T cell(s), (a) CD3+ T cell(s), (a) γδ T cell(s) or (a) natural killer (NK) T cell(s) for targeted tumor therapy, nucleic acid sequences, vectors capable of transducing such (a) T cell(s), (a) transduced T cell(s) carrying the nucleic acid sequences or vectors of the present invention, methods and kits comprising the nucleic acid sequences or vectors of the present invention. The invention also provides the use of said transduced T cell(s) in a method for the treatment of diseases characterized by CXCL16 overexpression as well as a pharmaceutical composition/medicament comprising (a) transduced T cell(s) expressing the CXCR6 for use in methods of treating diseases characterized by CXCL16 overexpression.

6 Claims, 27 Drawing Sheets

Figure 1:
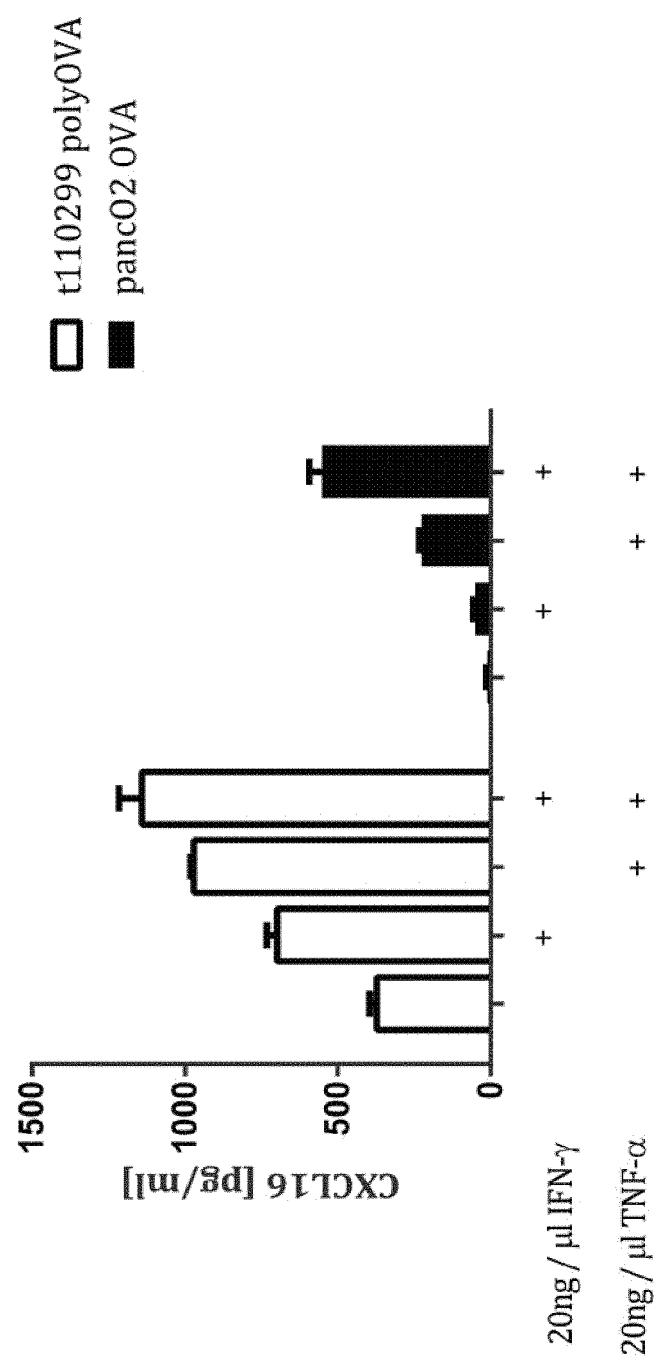

Specification includes a Sequence Listing.

SEQUENCE LISTING

```
<160> NUMBER OF SEQ ID NOS: 14

<210> SEQ ID NO 1
<211> LENGTH: 1026
<212> TYPE: DNA
<213> ORGANISM: Homo sapiens
<220> FEATURE:
<221> NAME/KEY: source
<222> LOCATION: 1..1026
<223> OTHER INFORMATION: /mol_type="unassigned DNA"
      /organism="Homo sapiens"
<220> FEATURE:
<221> NAME/KEY: CDS
<222> LOCATION: 1..1026
<223> OTHER INFORMATION: /transl_table=1

<400> SEQUENCE: 1 atg gcg gaa cat gat tat cat gaa gat tat ggc ttt agc agc ttt aac    48
Met Ala Glu His Asp Tyr His Glu Asp Tyr Gly Phe Ser Ser Phe Asn
1               5                   10                  15 gat agc agc cag gaa gaa cat cag gat ttt ctg cag ttt agc aaa gtg    96
Asp Ser Ser Gln Glu Glu His Gln Asp Phe Leu Gln Phe Ser Lys Val
            20                  25                  30
```

-continued

| | |
|---|---|
| ttt ctg ccg tgc atg tat ctg gtg gtg ttt gtg tgc ggc ctg gtg ggc<br>Phe Leu Pro Cys Met Tyr Leu Val Val Phe Val Cys Gly Leu Val Gly<br>          35                          40                          45 | 144 |
| aac agc ctg gtg ctg gtg att agc att ttt tat cat aaa ctg cag agc<br>Asn Ser Leu Val Leu Val Ile Ser Ile Phe Tyr His Lys Leu Gln Ser<br>50                         55                          60 | 192 |
| ctg acc gat gtg ttt ctg gtg aac ctg ccg ctg gcg gat ctg gtg ttt<br>Leu Thr Asp Val Phe Leu Val Asn Leu Pro Leu Ala Asp Leu Val Phe<br>65                         70                        75                        80 | 240 |
| gtg tgc acc ctg ccg ttt tgg gcg tat gcg ggc att cat gaa tgg gtg<br>Val Cys Thr Leu Pro Phe Trp Ala Tyr Ala Gly Ile His Glu Trp Val<br>                      85                          90                        95 | 288 |
| ttt ggc cag gtg atg tgc aaa agc ctg ctg ggc att tat acc att aac<br>Phe Gly Gln Val Met Cys Lys Ser Leu Leu Gly Ile Tyr Thr Ile Asn<br>                      100                       105                      110 | 336 |
| ttt tat acc agc atg ctg att ctg acc tgc att acc gtg gat cgc ttt<br>Phe Tyr Thr Ser Met Leu Ile Leu Thr Cys Ile Thr Val Asp Arg Phe<br>                 115                        120                       125 | 384 |
| att gtg gtg gtg aaa gcg acc aaa gcg tat aac cag cag gcg aaa cgc<br>Ile Val Val Val Lys Ala Thr Lys Ala Tyr Asn Gln Gln Ala Lys Arg<br>130                          135                        140 | 432 |
| atg acc tgg ggc aaa gtg acc agc ctg ctg att tgg gtg att agc ctg<br>Met Thr Trp Gly Lys Val Thr Ser Leu Leu Ile Trp Val Ile Ser Leu<br>145                        150                        155                        160 | 480 |
| ctg gtg agc ctg ccg cag att att tat ggc aac gtg ttt aac ctg gat<br>Leu Val Ser Leu Pro Gln Ile Ile Tyr Gly Asn Val Phe Asn Leu Asp<br>                        165                        170                      175 | 528 |
| aaa ctg att tgc ggc tat cat gat gaa gcg att agc acc gtg gtg ctg<br>Lys Leu Ile Cys Gly Tyr His Asp Glu Ala Ile Ser Thr Val Val Leu<br>                  180                        185                      190 | 576 |
| gcg acc cag atg acc ctg ggc ttt ttt ctg ccg ctg ctg acc atg att<br>Ala Thr Gln Met Thr Leu Gly Phe Phe Leu Pro Leu Leu Thr Met Ile<br>               195                        200                      205 | 624 |
| gtg tgc tat agc gtg att att aaa acc ctg ctg cat gcg ggc ggc ttt<br>Val Cys Tyr Ser Val Ile Ile Lys Thr Leu Leu His Ala Gly Gly Phe<br>210                          215                        220 | 672 |
| cag aaa cat cgc agc ctg aaa att att ttt ctg gtg atg gcg gtg ttt<br>Gln Lys His Arg Ser Leu Lys Ile Ile Phe Leu Val Met Ala Val Phe<br>225                        230                        235                        240 | 720 |
| ctg ctg acc cag atg ccg ttt aac ctg atg aaa ttt att cgc agc acc<br>Leu Leu Thr Gln Met Pro Phe Asn Leu Met Lys Phe Ile Arg Ser Thr<br>               245                        250                      255 | 768 |
| cat tgg gaa tat tat gcg atg acc agc ttt cat tat acc att atg gtg<br>His Trp Glu Tyr Tyr Ala Met Thr Ser Phe His Tyr Thr Ile Met Val<br>                      260                       265                      270 | 816 |
| acc gaa gcg att gcg tat ctg cgc gcg tgc ctg aac ccg gtg ctg tat<br>Thr Glu Ala Ile Ala Tyr Leu Arg Ala Cys Leu Asn Pro Val Leu Tyr<br>         275                        280                      285 | 864 |
| gcg ttt gtg agc ctg aaa ttt cgc aaa aac ttt tgg aaa ctg gtg aaa<br>Ala Phe Val Ser Leu Lys Phe Arg Lys Asn Phe Trp Lys Leu Val Lys<br>         290                        295                      300 | 912 |
| gat att ggc tgc ctg ccg tat ctg ggc gtg agc cat cag tgg aaa agc<br>Asp Ile Gly Cys Leu Pro Tyr Leu Gly Val Ser His Gln Trp Lys Ser<br>305                        310                        315                        320 | 960 |
| agc gaa gat aac agc aaa acc ttt agc gcg agc cat aac gtg gaa gcg<br>Ser Glu Asp Asn Ser Lys Thr Phe Ser Ala Ser His Asn Val Glu Ala<br>                      325                        330                      335 | 1008 |
| acc agc atg ttt cag ctg<br>Thr Ser Met Phe Gln Leu<br>               340 | 1026 |

<210> SEQ ID NO 2
<211> LENGTH: 342
<212> TYPE: PRT
<213> ORGANISM: Homo sapiens
<220> FEATURE:
<223> OTHER INFORMATION: [CDS]:1..1026 from SEQ ID NO 1

<400> SEQUENCE: 2

```
Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
            20                  25                  30

Phe Leu Pro Cys Met Tyr Leu Val Phe Val Cys Gly Leu Val Gly
        35                  40                  45

Asn Ser Leu Val Leu Val Ile Ser Ile Phe Tyr His Lys Leu Gln Ser
    50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
        115                 120                 125

Ile Val Val Val Lys Ala Thr Lys Ala Tyr Asn Gln Gln Ala Lys Arg
    130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
        195                 200                 205

Val Cys Tyr Ser Val Ile Ile Lys Thr Leu Leu His Ala Gly Gly Phe
    210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
        275                 280                 285

Ala Phe Val Ser Leu Lys Phe Arg Lys Asn Phe Trp Lys Leu Val Lys
    290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340
```

<210> SEQ ID NO 3

<211> LENGTH: 1050
<212> TYPE: DNA
<213> ORGANISM: Mus musculus
<220> FEATURE:
<221> NAME/KEY: source
<222> LOCATION: 1..1050
<223> OTHER INFORMATION: /mol_type="unassigned DNA"
      /organism="Mus musculus"
<220> FEATURE:
<221> NAME/KEY: CDS
<222> LOCATION: 1..1050
<223> OTHER INFORMATION: /transl_table=1

<400> SEQUENCE: 3

```
atg gat gat ggc cat cag gaa agc gcg ctg tat gat ggc cat tat gaa        48
Met Asp Asp Gly His Gln Glu Ser Ala Leu Tyr Asp Gly His Tyr Glu
1               5                   10                  15 ggc gat ttt tgg ctg ttt aac aac agc agc gat aac agc cag gaa aac        96
Gly Asp Phe Trp Leu Phe Asn Asn Ser Ser Asp Asn Ser Gln Glu Asn
                20                  25                  30 aaa cgc ttt ctg aaa ttt aaa gaa gtg ttt ctg ccg tgc gtg tat ctg       144
Lys Arg Phe Leu Lys Phe Lys Glu Val Phe Leu Pro Cys Val Tyr Leu
            35                  40                  45 gtg gtg ttt gtg ttt ggc ctg ctg ggc aac agc ctg gtg ctg att att       192
Val Val Phe Val Phe Gly Leu Leu Gly Asn Ser Leu Val Leu Ile Ile
        50                  55                  60 tat att ttt tat cag aaa ctg cgc acc ctg acc gat gtg ttt ctg ctg       240
Tyr Ile Phe Tyr Gln Lys Leu Arg Thr Leu Thr Asp Val Phe Leu Leu
65                  70                  75                  80 aac ctg ccg ctg gcg gat ctg gtg ttt gtg tgc acc ctg ccg ttt tgg       288
Asn Leu Pro Leu Ala Asp Leu Val Phe Val Cys Thr Leu Pro Phe Trp
                85                  90                  95 gcg tat gcg ggc acc tat gaa tgg gtg ttt ggc acc gtg atg tgc aaa       336
Ala Tyr Ala Gly Thr Tyr Glu Trp Val Phe Gly Thr Val Met Cys Lys
                100                 105                 110 acc ctg cgc ggc atg tat acc atg aac ttt tat gtg agc atg ctg acc       384
Thr Leu Arg Gly Met Tyr Thr Met Asn Phe Tyr Val Ser Met Leu Thr
            115                 120                 125 ctg acc tgc att acc gtg gat cgc ttt att gtg gtg gtg cag gcg acc       432
Leu Thr Cys Ile Thr Val Asp Arg Phe Ile Val Val Val Gln Ala Thr
        130                 135                 140 aaa gcg ttt aac cgc cag gcg aaa tgg aaa att tgg ggc cag gtg att       480
Lys Ala Phe Asn Arg Gln Ala Lys Trp Lys Ile Trp Gly Gln Val Ile
145                 150                 155                 160 tgc ctg ctg att tgg gtg gtg agc ctg ctg gtg agc ctg ccg cag att       528
Cys Leu Leu Ile Trp Val Val Ser Leu Leu Val Ser Leu Pro Gln Ile
                165                 170                 175 att tat ggc cat gtg cag gat att gat aaa ctg att tgc cag tat cat       576
Ile Tyr Gly His Val Gln Asp Ile Asp Lys Leu Ile Cys Gln Tyr His
                180                 185                 190 agc gaa gaa att agc acc atg gtg ctg gtg att cag atg acc ctg ggc       624
Ser Glu Glu Ile Ser Thr Met Val Leu Val Ile Gln Met Thr Leu Gly
            195                 200                 205 ttt ttt ctg ccg ctg ctg acc atg att ctg tgc tat agc ggc att att       672
Phe Phe Leu Pro Leu Leu Thr Met Ile Leu Cys Tyr Ser Gly Ile Ile
        210                 215                 220 aaa acc ctg ctg cat gcg cgc aac ttt cag aaa cat aaa agc ctg aaa       720
Lys Thr Leu Leu His Ala Arg Asn Phe Gln Lys His Lys Ser Leu Lys
225                 230                 235                 240 att att ttt ctg gtg gtg gcg gtg ttt ctg ctg acc cag acc ccg ttt       768
Ile Ile Phe Leu Val Val Ala Val Phe Leu Leu Thr Gln Thr Pro Phe
                245                 250                 255
```

```
aac ctg gcg atg ctg att cag agc acc agc tgg gaa tat tat acc att    816
Asn Leu Ala Met Leu Ile Gln Ser Thr Ser Trp Glu Tyr Tyr Thr Ile
            260                 265                 270 acc agc ttt aaa tat gcg att gtg gtg acc gaa gcg att gcg tat ttt    864
Thr Ser Phe Lys Tyr Ala Ile Val Val Thr Glu Ala Ile Ala Tyr Phe
        275                 280                 285 cgc gcg tgc ctg aac ccg gtg ctg tat gcg ttt gtg ggc ctg aaa ttt    912
Arg Ala Cys Leu Asn Pro Val Leu Tyr Ala Phe Val Gly Leu Lys Phe
    290                 295                 300 cgc aaa aac gtg tgg aaa ctg atg aaa gat att ggc tgc ctg agc cat    960
Arg Lys Asn Val Trp Lys Leu Met Lys Asp Ile Gly Cys Leu Ser His
305                 310                 315                 320 ctg ggc gtg agc agc cag tgg aaa agc agc gaa gat agc agc aaa acc   1008
Leu Gly Val Ser Ser Gln Trp Lys Ser Ser Glu Asp Ser Ser Lys Thr
                325                 330                 335 tgc agc gcg agc cat aac gtg gaa acc acc agc atg ttt cag            1050
Cys Ser Ala Ser His Asn Val Glu Thr Thr Ser Met Phe Gln
            340                 345                 350

<210> SEQ ID NO 4
<211> LENGTH: 350
<212> TYPE: PRT
<213> ORGANISM: Mus musculus
<220> FEATURE:
<223> OTHER INFORMATION: [CDS]:1..1050 from SEQ ID NO 3

<400> SEQUENCE: 4

Met Asp Asp Gly His Gln Glu Ser Ala Leu Tyr Asp Gly His Tyr Glu
1               5                   10                  15

Gly Asp Phe Trp Leu Phe Asn Asn Ser Ser Asp Asn Ser Gln Glu Asn
            20                  25                  30

Lys Arg Phe Leu Lys Phe Lys Glu Val Phe Leu Pro Cys Val Tyr Leu
        35                  40                  45

Val Val Phe Val Phe Gly Leu Leu Gly Asn Ser Leu Val Leu Ile Ile
    50                  55                  60

Tyr Ile Phe Tyr Gln Lys Leu Arg Thr Leu Thr Asp Val Phe Leu Leu
65                  70                  75                  80

Asn Leu Pro Leu Ala Asp Leu Val Phe Val Cys Thr Leu Pro Phe Trp
                85                  90                  95

Ala Tyr Ala Gly Thr Tyr Glu Trp Val Phe Gly Thr Val Met Cys Lys
            100                 105                 110

Thr Leu Arg Gly Met Tyr Thr Met Asn Phe Tyr Val Ser Met Leu Thr
        115                 120                 125

Leu Thr Cys Ile Thr Val Asp Arg Phe Ile Val Val Gln Ala Thr
    130                 135                 140

Lys Ala Phe Asn Arg Gln Ala Lys Trp Lys Ile Trp Gly Gln Val Ile
145                 150                 155                 160

Cys Leu Leu Ile Trp Val Val Ser Leu Leu Val Ser Leu Pro Gln Ile
                165                 170                 175

Ile Tyr Gly His Val Gln Asp Ile Asp Lys Leu Ile Cys Gln Tyr His
            180                 185                 190

Ser Glu Glu Ile Ser Thr Met Val Leu Val Ile Gln Met Thr Leu Gly
        195                 200                 205

Phe Phe Leu Pro Leu Leu Thr Met Ile Leu Cys Tyr Ser Gly Ile Ile
    210                 215                 220

Lys Thr Leu Leu His Ala Arg Asn Phe Gln Lys His Lys Ser Leu Lys
225                 230                 235                 240
```

```
Ile Ile Phe Leu Val Val Ala Val Phe Leu Thr Gln Thr Pro Phe
                245                 250                 255

Asn Leu Ala Met Leu Ile Gln Ser Thr Ser Trp Glu Tyr Tyr Thr Ile
        260                 265                 270

Thr Ser Phe Lys Tyr Ala Ile Val Thr Glu Ala Ile Ala Tyr Phe
            275                 280                 285

Arg Ala Cys Leu Asn Pro Val Leu Tyr Ala Phe Val Gly Leu Lys Phe
290                 295                 300

Arg Lys Asn Val Trp Lys Leu Met Lys Asp Ile Gly Cys Leu Ser His
305                 310                 315                 320

Leu Gly Val Ser Ser Gln Trp Lys Ser Glu Asp Ser Ser Lys Thr
            325                 330                 335

Cys Ser Ala Ser His Asn Val Glu Thr Thr Ser Met Phe Gln
            340                 345                 350

<210> SEQ ID NO 5
<211> LENGTH: 762
<212> TYPE: DNA
<213> ORGANISM: Homo sapiens
<220> FEATURE:
<221> NAME/KEY: source
<222> LOCATION: 1..762
<223> OTHER INFORMATION: /mol_type="unassigned DNA"
      /organism="Homo sapiens"
<220> FEATURE:
<221> NAME/KEY: CDS
<222> LOCATION: 1..762
<223> OTHER INFORMATION: /transl_table=1

<400> SEQUENCE: 5 atg ggc cgc gat ctg cgc ccg ggc agc cgc gtg ctg ctg ctg ctg           48
Met Gly Arg Asp Leu Arg Pro Gly Ser Arg Val Leu Leu Leu Leu
1               5                   10                  15 ctg ctg ctg ctg gtg tat ctg acc cag ccg ggc aac ggc aac gaa ggc       96
Leu Leu Leu Leu Val Tyr Leu Thr Gln Pro Gly Asn Gly Asn Glu Gly
                20                  25                  30 agc gtg acc ggc agc tgc tat tgc ggc aaa cgc att agc agc gat agc       144
Ser Val Thr Gly Ser Cys Tyr Cys Gly Lys Arg Ile Ser Ser Asp Ser
            35                  40                  45 ccg ccg agc gtg cag ttt atg aac cgc ctg cgc aaa cat ctg cgc gcg       192
Pro Pro Ser Val Gln Phe Met Asn Arg Leu Arg Lys His Leu Arg Ala
50                  55                  60 tat cat cgc tgc ctg tat tat acc cgc ttt cag ctg ctg agc tgg agc       240
Tyr His Arg Cys Leu Tyr Tyr Thr Arg Phe Gln Leu Leu Ser Trp Ser
65                  70                  75                  80 gtg tgc ggc ggc aac aaa gat ccg tgg gtg cag gaa ctg atg agc tgc       288
Val Cys Gly Gly Asn Lys Asp Pro Trp Val Gln Glu Leu Met Ser Cys
                85                  90                  95 ctg gat ctg aaa gaa tgc ggc cat gcg tat agc ggc att gtg gcg cat       336
Leu Asp Leu Lys Glu Cys Gly His Ala Tyr Ser Gly Ile Val Ala His
                100                 105                 110 cag aaa cat ctg ctg ccg acc agc ccg ccg att agc cag gcg agc gaa       384
Gln Lys His Leu Leu Pro Thr Ser Pro Pro Ile Ser Gln Ala Ser Glu
            115                 120                 125 ggc gcg agc agc gat att cat acc ccg gcg cag atg ctg ctg agc acc       432
Gly Ala Ser Ser Asp Ile His Thr Pro Ala Gln Met Leu Leu Ser Thr
130                 135                 140 ctg cag agc acc cag cgc ccg acc ctg ccg gtg ggc agc ctg agc agc       480
Leu Gln Ser Thr Gln Arg Pro Thr Leu Pro Val Gly Ser Leu Ser Ser
145                 150                 155                 160 gat aaa gaa ctg acc cgc ccg aac gaa acc acc att cat acc gcg ggc       528
```

```
Asp Lys Glu Leu Thr Arg Pro Asn Glu Thr Thr Ile His Thr Ala Gly
                165                 170                 175 cat agc ctg gcg gcg ggc ccg gaa gcg ggc gaa aac cag aaa cag ccg      576
His Ser Leu Ala Ala Gly Pro Glu Ala Gly Glu Asn Gln Lys Gln Pro
            180                 185                 190 gaa aaa aac gcg ggc ccg acc gcg cgc acc agc gcg acc gtg ccg gtg      624
Glu Lys Asn Ala Gly Pro Thr Ala Arg Thr Ser Ala Thr Val Pro Val
        195                 200                 205 ctg tgc ctg ctg gcg att att ttt att ctg acc gcg gcg ctg agc tat      672
Leu Cys Leu Leu Ala Ile Ile Phe Ile Leu Thr Ala Ala Leu Ser Tyr
    210                 215                 220 gtg ctg tgc aaa cgc cgc cgc ggc cag agc ccg cag agc agc ccg gat      720
Val Leu Cys Lys Arg Arg Arg Gly Gln Ser Pro Gln Ser Ser Pro Asp
225                 230                 235                 240 ctg ccg gtg cat tat att ccg gtg gcg ccg gat agc aac acc              762
Leu Pro Val His Tyr Ile Pro Val Ala Pro Asp Ser Asn Thr
                245                 250

<210> SEQ ID NO 6
<211> LENGTH: 254
<212> TYPE: PRT
<213> ORGANISM: Homo sapiens
<220> FEATURE:
<223> OTHER INFORMATION: [CDS]:1..762 from SEQ ID NO 5

<400> SEQUENCE: 6

Met Gly Arg Asp Leu Arg Pro Gly Ser Arg Val Leu Leu Leu Leu Leu
1               5                   10                  15

Leu Leu Leu Leu Val Tyr Leu Thr Gln Pro Gly Asn Gly Asn Glu Gly
            20                  25                  30

Ser Val Thr Gly Ser Cys Tyr Cys Gly Lys Arg Ile Ser Ser Asp Ser
        35                  40                  45

Pro Pro Ser Val Gln Phe Met Asn Arg Leu Arg Lys His Leu Arg Ala
    50                  55                  60

Tyr His Arg Cys Leu Tyr Tyr Thr Arg Phe Gln Leu Leu Ser Trp Ser
65                  70                  75                  80

Val Cys Gly Gly Asn Lys Asp Pro Trp Val Gln Glu Leu Met Ser Cys
                85                  90                  95

Leu Asp Leu Lys Glu Cys Gly His Ala Tyr Ser Gly Ile Val Ala His
            100                 105                 110

Gln Lys His Leu Leu Pro Thr Ser Pro Pro Ile Ser Gln Ala Ser Glu
        115                 120                 125

Gly Ala Ser Ser Asp Ile His Thr Pro Ala Gln Met Leu Leu Ser Thr
    130                 135                 140

Leu Gln Ser Thr Gln Arg Pro Thr Leu Pro Val Gly Ser Leu Ser Ser
145                 150                 155                 160

Asp Lys Glu Leu Thr Arg Pro Asn Glu Thr Thr Ile His Thr Ala Gly
                165                 170                 175

His Ser Leu Ala Ala Gly Pro Glu Ala Gly Glu Asn Gln Lys Gln Pro
            180                 185                 190

Glu Lys Asn Ala Gly Pro Thr Ala Arg Thr Ser Ala Thr Val Pro Val
        195                 200                 205

Leu Cys Leu Leu Ala Ile Ile Phe Ile Leu Thr Ala Ala Leu Ser Tyr
    210                 215                 220

Val Leu Cys Lys Arg Arg Arg Gly Gln Ser Pro Gln Ser Ser Pro Asp
225                 230                 235                 240

Leu Pro Val His Tyr Ile Pro Val Ala Pro Asp Ser Asn Thr
                245                 250
```

<210> SEQ ID NO 7
<211> LENGTH: 738
<212> TYPE: DNA
<213> ORGANISM: Mus musculus
<220> FEATURE:
<221> NAME/KEY: source
<222> LOCATION: 1..738
<223> OTHER INFORMATION: /mol_type="unassigned DNA"
     /organism="Mus musculus"
<220> FEATURE:
<221> NAME/KEY: CDS
<222> LOCATION: 1..738
<223> OTHER INFORMATION: /transl_table=1

<400> SEQUENCE: 7

| | | | | | | | | | | | | | | | |
|---|---|---|---|---|---|---|---|---|---|---|---|---|---|---|---|
| atg | cgc | cgc | ggc | ttt | ggc | ccg | ctg | agc | ctg | gcg | ttt | ttt | ctg | ttt | ctg | 48 |
| Met | Arg | Arg | Gly | Phe | Gly | Pro | Leu | Ser | Leu | Ala | Phe | Phe | Leu | Phe | Leu | |
| 1 | | | | 5 | | | | | 10 | | | | | 15 | | | ctg gcg ctg ctg acc ctg ccg ggc gat ggc aac cag ggc agc gtg gcg   96
Leu Ala Leu Leu Thr Leu Pro Gly Asp Gly Asn Gln Gly Ser Val Ala
            20                  25                  30 ggc agc tgc agc tgc gat cgc acc att agc agc ggc acc cag att ccg  144
Gly Ser Cys Ser Cys Asp Arg Thr Ile Ser Ser Gly Thr Gln Ile Pro
        35                  40                  45 cag ggc acc ctg gat cat att cgc aaa tat ctg aaa gcg ttt cat cgc  192
Gln Gly Thr Leu Asp His Ile Arg Lys Tyr Leu Lys Ala Phe His Arg
 50                  55                  60 tgc ccg ttt ttt att cgc ttt cag ctg cag agc aaa agc gtg tgc ggc  240
Cys Pro Phe Phe Ile Arg Phe Gln Leu Gln Ser Lys Ser Val Cys Gly
 65                  70                  75                  80 ggc agc cag gat cag tgg gtg cgc gaa ctg gtg gat tgc ttt gaa cgc  288
Gly Ser Gln Asp Gln Trp Val Arg Glu Leu Val Asp Cys Phe Glu Arg
                 85                  90                  95 aaa gaa tgc ggc acc ggc cat ggc aaa agc ttt cat cat cag aaa cat  336
Lys Glu Cys Gly Thr Gly His Gly Lys Ser Phe His His Gln Lys His
            100                 105                 110 ctg ccg cag gcg agc acc cag acc ccg gaa gcg gcg gaa ggc acc ccg  384
Leu Pro Gln Ala Ser Thr Gln Thr Pro Glu Ala Ala Glu Gly Thr Pro
        115                 120                 125 agc gat acc agc acc ccg gcg cat agc cag agc acc cag cat agc acc  432
Ser Asp Thr Ser Thr Pro Ala His Ser Gln Ser Thr Gln His Ser Thr
130                 135                 140 ctg ccg agc ggc gcg ctg agc ctg aac aaa gaa cat acc cag ccg tgg  480
Leu Pro Ser Gly Ala Leu Ser Leu Asn Lys Glu His Thr Gln Pro Trp
145                 150                 155                 160 gaa atg acc acc ctg ccg agc ggc tat ggc ctg gaa gcg cgc ccg gaa  528
Glu Met Thr Thr Leu Pro Ser Gly Tyr Gly Leu Glu Ala Arg Pro Glu
                165                 170                 175 gcg gaa gcg aac gaa aaa cag cag gat gat cgc cag cag gaa gcg ccg  576
Ala Glu Ala Asn Glu Lys Gln Gln Asp Asp Arg Gln Gln Glu Ala Pro
            180                 185                 190 ggc gcg ggc gcg agc acc ccg gcg tgg gtg ccg gtg ctg agc ctg ctg  624
Gly Ala Gly Ala Ser Thr Pro Ala Trp Val Pro Val Leu Ser Leu Leu
        195                 200                 205 gcg att gtg ttt ttt ctg acc gcg gcg atg gcg tat gtg ctg tgc aac  672
Ala Ile Val Phe Phe Leu Thr Ala Ala Met Ala Tyr Val Leu Cys Asn
    210                 215                 220 cgc cgc gcg acc cag cag aac agc gcg ggc ctg cag ctg tgg tat acc  720
Arg Arg Ala Thr Gln Gln Asn Ser Ala Gly Leu Gln Leu Trp Tyr Thr
225                 230                 235                 240

```
ccg gtg gaa ccg cgc ccg                                              738
Pro Val Glu Pro Arg Pro
            245
```

<210> SEQ ID NO 8
<211> LENGTH: 246
<212> TYPE: PRT
<213> ORGANISM: Mus musculus
<220> FEATURE:
<223> OTHER INFORMATION: [CDS]:1..738 from SEQ ID NO 7

<400> SEQUENCE: 8

```
Met Arg Arg Gly Phe Gly Pro Leu Ser Leu Ala Phe Leu Phe Leu
1               5                   10                  15

Leu Ala Leu Leu Thr Leu Pro Gly Asp Gly Asn Gln Gly Ser Val Ala
            20                  25                  30

Gly Ser Cys Ser Cys Asp Arg Thr Ile Ser Ser Gly Thr Gln Ile Pro
        35                  40                  45

Gln Gly Thr Leu Asp His Ile Arg Lys Tyr Leu Lys Ala Phe His Arg
    50                  55                  60

Cys Pro Phe Phe Ile Arg Phe Gln Leu Gln Ser Lys Ser Val Cys Gly
65                  70                  75                  80

Gly Ser Gln Asp Gln Trp Val Arg Glu Leu Val Asp Cys Phe Glu Arg
                85                  90                  95

Lys Glu Cys Gly Thr Gly His Gly Lys Ser Phe His His Gln Lys His
            100                 105                 110

Leu Pro Gln Ala Ser Thr Gln Thr Pro Glu Ala Ala Glu Gly Thr Pro
        115                 120                 125

Ser Asp Thr Ser Thr Pro Ala His Ser Gln Ser Thr Gln His Ser Thr
    130                 135                 140

Leu Pro Ser Gly Ala Leu Ser Leu Asn Lys Glu His Thr Gln Pro Trp
145                 150                 155                 160

Glu Met Thr Thr Leu Pro Ser Gly Tyr Gly Leu Glu Ala Arg Pro Glu
                165                 170                 175

Ala Glu Ala Asn Glu Lys Gln Gln Asp Asp Arg Gln Gln Glu Ala Pro
            180                 185                 190

Gly Ala Gly Ala Ser Thr Pro Ala Trp Val Pro Val Leu Ser Leu Leu
        195                 200                 205

Ala Ile Val Phe Phe Leu Thr Ala Ala Met Ala Tyr Val Leu Cys Asn
    210                 215                 220

Arg Arg Ala Thr Gln Gln Asn Ser Ala Gly Leu Gln Leu Trp Tyr Thr
225                 230                 235                 240

Pro Val Glu Pro Arg Pro
                245
```

<210> SEQ ID NO 9
<211> LENGTH: 88
<212> TYPE: PRT
<213> ORGANISM: Artificial Sequence
<220> FEATURE:
<223> OTHER INFORMATION: Recombinant CXCL16

<400> SEQUENCE: 9

```
Asn Gln Gly Ser Val Ala Gly Ser Cys Ser Cys Asp Arg Thr Ile Ser
1               5                   10                  15

Ser Gly Thr Gln Ile Pro Gln Gly Thr Leu Asp His Ile Arg Lys Tyr
            20                  25                  30

Leu Lys Ala Phe His Arg Cys Pro Phe Phe Ile Arg Phe Gln Leu Gln
```

-continued

```
                    35                  40                  45
Ser Lys Ser Val Cys Gly Gly Ser Gln Asp Gln Trp Val Arg Glu Leu
    50                  55                  60
Val Asp Cys Phe Glu Arg Lys Glu Cys Gly Thr Gly His Gly Lys Ser
 65                  70                  75                  80
Phe His His Gln Lys His Leu Pro
                85

<210> SEQ ID NO 10
<211> LENGTH: 8
<212> TYPE: PRT
<213> ORGANISM: Artificial Sequence
<220> FEATURE:
<223> OTHER INFORMATION: OVA257-264 peptide

<400> SEQUENCE: 10

Ser Ile Ile Asn Phe Glu Lys Leu
1               5

<210> SEQ ID NO 11
<211> LENGTH: 729
<212> TYPE: DNA
<213> ORGANISM: Artificial Sequence
<220> FEATURE:
<221> NAME/KEY: source
<222> LOCATION: 1..729
<223> OTHER INFORMATION: /mol_type="unassigned DNA"
      /note="GFP sequence"
      /organism="Artificial Sequence"
<220> FEATURE:
<221> NAME/KEY: CDS
<222> LOCATION: 1..729
<223> OTHER INFORMATION: /transl_table=1

<400> SEQUENCE: 11 atg gcc acc atg gtg agc aag ggc gag gag ctg ttc acc ggg gtg gtg      48
Met Ala Thr Met Val Ser Lys Gly Glu Glu Leu Phe Thr Gly Val Val
1               5                  10                  15 ccc atc ctg gtc gag ctg gac ggc gac gta aac ggc cac aag ttc agc      96
Pro Ile Leu Val Glu Leu Asp Gly Asp Val Asn Gly His Lys Phe Ser
            20                  25                  30 gtg tcc ggc gag ggc gag ggc gat gcc acc tac ggc aag ctg acc ctg     144
Val Ser Gly Glu Gly Glu Gly Asp Ala Thr Tyr Gly Lys Leu Thr Leu
        35                  40                  45 aag ttc atc tgc acc acc ggc aag ctg ccc gtg ccc tgg ccc acc ctc     192
Lys Phe Ile Cys Thr Thr Gly Lys Leu Pro Val Pro Trp Pro Thr Leu
    50                  55                  60 gtg acc acc ctg acc tac ggc gtg cag tgc ttc agc cgc tac ccc gac     240
Val Thr Thr Leu Thr Tyr Gly Val Gln Cys Phe Ser Arg Tyr Pro Asp
 65                  70                  75                  80 cac atg aag cag cac gac ttc ttc aag tcc gcc atg ccc gaa ggc tac     288
His Met Lys Gln His Asp Phe Phe Lys Ser Ala Met Pro Glu Gly Tyr
                85                  90                  95 gtc cag gag cgc acc atc ttc ttc aag gac gac ggc aac tac aag acc     336
Val Gln Glu Arg Thr Ile Phe Phe Lys Asp Asp Gly Asn Tyr Lys Thr
            100                 105                 110 cgc gcc gag gtg aag ttc gag ggc gac acc ctg gtg aac cgc atc gag     384
Arg Ala Glu Val Lys Phe Glu Gly Asp Thr Leu Val Asn Arg Ile Glu
        115                 120                 125 ctg aag ggc atc gac ttc aag gag gac ggc aac atc ctg ggg cac aag     432
Leu Lys Gly Ile Asp Phe Lys Glu Asp Gly Asn Ile Leu Gly His Lys
    130                 135                 140 ctg gag tac aac tac aac agc cac aac gtc tat atc atg gcc gac aag     480
```

```
Leu Glu Tyr Asn Tyr Asn Ser His Asn Val Tyr Ile Met Ala Asp Lys
145                 150                 155                 160 cag aag aac ggc atc aag gtg aac ttc aag atc cgc cac aac atc gag    528
Gln Lys Asn Gly Ile Lys Val Asn Phe Lys Ile Arg His Asn Ile Glu
                165                 170                 175 gac ggc agc gtg cag ctc gcc gac cac tac cag cag aac acc ccc atc    576
Asp Gly Ser Val Gln Leu Ala Asp His Tyr Gln Gln Asn Thr Pro Ile
            180                 185                 190 ggc gac ggc ccc gtg ctg ctg ccc gac aac cac tac ctg agc acc cag    624
Gly Asp Gly Pro Val Leu Leu Pro Asp Asn His Tyr Leu Ser Thr Gln
        195                 200                 205 tcc gcc ctg agc aaa gac ccc aac gag aag cgc gat cac atg gtc ctg    672
Ser Ala Leu Ser Lys Asp Pro Asn Glu Lys Arg Asp His Met Val Leu
    210                 215                 220 ctg gag ttc gtg acc gcc gcc ggg atc act ctc ggc atg gac gag ctg    720
Leu Glu Phe Val Thr Ala Ala Gly Ile Thr Leu Gly Met Asp Glu Leu
225                 230                 235                 240 tac aag taa                                                        729
Tyr Lys
```

<210> SEQ ID NO 12
<211> LENGTH: 242
<212> TYPE: PRT
<213> ORGANISM: Artificial Sequence
<220> FEATURE:
<223> OTHER INFORMATION: [CDS]:1..729 from SEQ ID NO 11

<400> SEQUENCE: 12

```
Met Ala Thr Met Val Ser Lys Gly Glu Glu Leu Phe Thr Gly Val Val
1               5                   10                  15

Pro Ile Leu Val Glu Leu Asp Gly Asp Val Asn Gly His Lys Phe Ser
                20                  25                  30

Val Ser Gly Glu Gly Glu Gly Asp Ala Thr Tyr Gly Lys Leu Thr Leu
            35                  40                  45

Lys Phe Ile Cys Thr Thr Gly Lys Leu Pro Val Pro Trp Pro Thr Leu
    50                  55                  60

Val Thr Thr Leu Thr Tyr Gly Val Gln Cys Phe Ser Arg Tyr Pro Asp
65                  70                  75                  80

His Met Lys Gln His Asp Phe Phe Lys Ser Ala Met Pro Glu Gly Tyr
                85                  90                  95

Val Gln Glu Arg Thr Ile Phe Phe Lys Asp Asp Gly Asn Tyr Lys Thr
                100                 105                 110

Arg Ala Glu Val Lys Phe Glu Gly Asp Thr Leu Val Asn Arg Ile Glu
            115                 120                 125

Leu Lys Gly Ile Asp Phe Lys Glu Asp Gly Asn Ile Leu Gly His Lys
    130                 135                 140

Leu Glu Tyr Asn Tyr Asn Ser His Asn Val Tyr Ile Met Ala Asp Lys
145                 150                 155                 160

Gln Lys Asn Gly Ile Lys Val Asn Phe Lys Ile Arg His Asn Ile Glu
                165                 170                 175

Asp Gly Ser Val Gln Leu Ala Asp His Tyr Gln Gln Asn Thr Pro Ile
            180                 185                 190

Gly Asp Gly Pro Val Leu Leu Pro Asp Asn His Tyr Leu Ser Thr Gln
        195                 200                 205

Ser Ala Leu Ser Lys Asp Pro Asn Glu Lys Arg Asp His Met Val Leu
    210                 215                 220

Leu Glu Phe Val Thr Ala Ala Gly Ile Thr Leu Gly Met Asp Glu Leu
```

-continued

```
225                 230                 235                 240
Tyr Lys

<210> SEQ ID NO 13
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
      /note="Primer"
      /organism="Artificial Sequence"

<400> SEQUENCE: 13
attagcggcc gcatggatga tggccatcag g                               31

<210> SEQ ID NO 14
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer"
      /organism="Artificial Sequence"

<400> SEQUENCE: 14
ggaaaccacc agcatgtttc aggaattc                                   28
```

CXCR6-TRANSDUCED T CELLS FOR TARGETED TUMOR THERAPY

The present application is a National Phase application of International Application No. PCT/EP2016/074644, filed Oct. 14, 2016, which claims priority to European Application No. 15190179.0 filed Oct. 16, 2015. The entirety of each application is incorporated by reference herein. The International Application was published in English on Apr. 20, 2017 as Publication No. WO 2017/064222 A1, the entire contents of which are hereby incorporated by reference herein.

The present invention relates to CXCR6-transduced (a) T cell(s) such as (a) CD8+ T cell(s), (a) CD4+ T cell(s), (a) CD3+ T cell(s), (a) γδ T cell(s) or (a) natural killer (NK) T cell(s) for targeted tumor therapy, nucleic acid sequences, vectors capable of transducing such (a) T cell(s), (a) transduced T cell(s) carrying the nucleic acid sequences or vectors of the present invention, methods and kits comprising the nucleic acid sequences or vectors of the present invention. The invention also provides the use of said transduced T cell(s) in a method for the treatment of diseases characterized by CXCL16 overexpression as well as a pharmaceutical composition/medicament comprising (a) transduced T cell(s) expressing the CXCR6 for use in methods of treating diseases characterized by CXCL16 overexpression.

Adoptive T cell therapy (ACT) is a powerful treatment approach using cancer-specific T cells (Rosenberg and Restifo, Science 348(6230) (2015), 62-68). ACT may use naturally occurring tumor-specific cells or T cells rendered specific by genetic engineering using T cell or chimeric antigen receptors (Rosenberg and Restifo, Science 348 (6230) (2015), 62-68). WO-A1 2015/028444 that is located in the field of adoptive T cell therapy (ACT) describes transduced T cells expressing an anti-CD30 chimeric antigen receptor (CAR) for use in treating CD30 positive cancer. Moreover, US-A1 2014/271635 discloses recombinant T cells expressing a chimeric antigen receptor specific for CD19 for use in the treatment of diseases associated with the expression of CD19. ACT can successfully treat and induce remission in patients suffering even from advanced and otherwise treatment refractory diseases such as acute lymphatic leukemia, non-hodgkins lymphoma or melanoma (Dudley et al., J Clin Oncol 26(32) (2008), 5233-5239; Grupp et al., N Engl J Med 368 (16) (2013), 1509-1518; Kochenderfer et al., J Clin Oncol. (2015) 33(6):540-9. doi: 10.1200/JCO.2014.56.2025. Epub 2014 Aug. 25). However, long term benefits are restricted to a small subset of patients while most will relapse and succumb to their refractory disease.

Access of T cells to tumor cells or tissue has been deemed essential for the success of ACT. Thus strategies enabling T cell entry need to be developed and implemented (Gattinoni et al., Nat Rev Immunol 6(5) (2006), 383-393). The currently most effective method to achieve enhanced T cell infiltration is total body irradiation, which permeabilizes tumor tissue, remodels the vasculature and depletes suppressive cells (Dudley et al., J Clin Oncol 23(10) (2005), 2346-2357). While this strategy has shown efficacy in clinical trials, its unspecific nature induces severe side effects, limiting its applicability and calling for more specific strategies (Dudley et al., J Clin Oncol 23(10) (2005), 2346-2357).

T cell entry and trafficking into tissues is a tightly regulated process where integrins and chemokines play a central role (Franciszkiewicz et al., Cancer Res 72(24) (2012), 6325-6332; Kalos and June, Immunity 39(1) (2013), 49-60). Chemokines are secreted by resident cells and form gradients, which attract cells bearing their corresponding receptor, regulating cellular entry (Franciszkiewicz et al., Cancer Res 72(24) (2012), 6325-6332). Tumors use this principle to attract immune suppressive cellular populations while excluding proinflammatory subsets (Curiel et al., Nat Med 10(9) (2004), 942-949). Wennerberg et al., Cancer Immunol Immunother 64 (2015), 225-235, located in the field of adoptive T cell therapy (ACT), discloses that ex vivo expansion of natural killer (NK) cells results in an increased expression of the CXCR3 receptor. Further, it is described in Wennerberg et al. that these expanded NK cells displayed an improved migration capacity toward solid tumors secreting CXCL10. However, the NK cells as described in Wennerberg et al. were not genetically engineered to express the chemokine receptor CXCR3. Introducing chemokine receptors (that are targeted by chemokines expressed within the tumor tissue) into T cells has been used to redirect antigen-specific T cells and to enhance their migration into the tumor tissue. CCR2, CCR4 and CXCR2 have been tested in preclinical models. They lead to enhanced therapeutic efficacy of ACT but generally fail to reject tumors, indicating insufficient infiltration and functionality of T cells at the tumor site (Di Stasi et al., Blood 113(25) (2009), 6392-6402; Peng et al., Clin Cancer Res 16(22) (2010), 5458-5468; Asai et al., PLoS One 8(2) (2013), e56820). Further, Sapoznik et al., Cancer Immunol Immunother 61 (2012), 1833-1847 discloses that tumor infiltrating lymphocyte (TIL) cells engineered to express CXCR1 showed enhanced migration towards melanoma cells secreting the chemokine CXCL8. Further, the transfection of the murine B cell line Baf-3 cells with a vector construct harbouring the mouse CXCR6 was described (Matsumura et al., J. Immunol. 181 (2013), 3099-3107). However, the sole purpose of the experimental procedure described in the Matsumura et al. publication was to prove that CXCL16 secreted by mouse tumor cells previously treated with radiation was functional, i.e. that such mouse tumor cells could induce the migration of CXCR6 positive cells. Thus the transfection of the murine B cell line Baf-3 cells with a vector construct harbouring the mouse CXCR6 was made in order to generate a functional cell line for CXCL16 effects and not vice versa for CXCR6 impact. As mentioned above, the transfected cell line described in the Matsumura et al. publication is a murine B cell line, i.e. a lineage totally independent of T cells functionality and development. Thus the herein demonstrated therapeutic efficacy of CXCR6 transduced T cells cannot be extrapolated from the murine B cell line described in the Matsumura et al. publication. Further, Xiao et al., Oncotarget, 6(16) (2015), 14165-14178 discloses the construction of a vector expressing the full-length human CXCR6 for the transduction of human breast cells. Moreover, Deng et al., Nature 388 (1997), 296-300 discloses vectors harboring the human CXCR6 sequence as deposited under the accession number AF007545. However, the vectors as described in Xiao et al. and Deng et al. have neither been completely structurally characterized nor have been deposited.

Accordingly, the targeted tumor therapy, particularly the adoptive T cell therapy needs to be improved in order to suffice the needs of the cancer patients. Thus, there is still a need to provide improved means having the potential to improve safety and efficacy of the ACT and overcome the above disadvantages.

This need is addressed by the present invention by providing the embodiments as defined in the claims.

The present invention relates to a vector capable of transducing (a) T cell(s), preferably (a) CD8+ T cell(s), (a) CD4+ T cell(s), (a) CD3+ T cell(s), (a) γδ T cell(s) or (a) natural killer (NK) T cell(s), most preferably (a) CD8+ T cell(s), comprising/which comprise a nucleic acid encoding a chemokine receptor 6 (CXCR6) or a fragment thereof, which is characterized by having chemokine receptor 6 (CXCR6) activity.

CXCR6 is the receptor for CXCL16, which is secreted by myeloid cells but also by malignant cells such as pancreatic cancer cells (Gaida et al., Clin Exp Immunol 154(2) (2008), 216-223; van der Voort et al., J Leukoc Biol 87(6) (2010), 1029-1039). The expression of CXCR6 is restricted to certain CD4+ T cell subsets, natural killer (NK) T cells and myeloid cells but is absent from cytotoxic CD8+ T cells (Matloubian et al, Nat Immunol 1(4) (2000), 298-304; van der Voort et al, J Leukoc Biol 87(6) (2010), 1029-1039). The ligand of CXCR6 exists in two forms: membrane bound CXL16 and a secreted soluble form of CXCL16. This explains the dual function of CXCR6. CXCR6 mediates migration towards soluble CXCL16 and mediates adhesion through the membrane bound form (Matloubian et al., Nat Immunol 1(4) (2000), 298-304; Gough et al., J Immunol 172(6) (2004), 3678-3685). These properties render CXCR6 unique among chemokine receptors. In the context of the present invention, it has surprisingly and unexpectedly been found that CXCR6 can be transduced into CD8+ T cells and thereby mediates their migration towards tumor cells. In addition, the data that have been obtained in context of the present invention indicate that CXCR6-transduced T cells, preferably CD8+ T cells, CD4+ T cells, CD3+ T cells, γδ T cells or natural killer (NK) T cells, most preferably CD8+ T cells, have the further advantage that they adhere to the target tumor cells in an antigen-independent manner, and thus support tumor cell recognition at the tumor site. Accordingly, the present invention relates to the transduction of (a) T cell(s), preferably (a) CD8+ T cell(s), (a) CD4+ T cell(s), (a) CD3+ T cell(s), (a) γδ T cell(s) or (a) natural killer (NK) T cell(s), most preferably (a) CD8+ T cell(s), with CXCR6 thereby mediating their migration towards (a) tumor cell(s) secreting CXCL16. As shown in the appended Examples, the treatment of (a) tumor(s) with (a) transduced T cell(s) expressing a chemokine receptor 6 (CXCR6) significantly reduces the tumor size compared to control experiments (see FIG. 17). Accordingly, it was surprisingly found that transduced T cell(s) expressing a chemokine receptor 6 (CXCR6) can be used for the treatment of diseases characterized by CXCL16 overexpression such as pancreatic cancer.

Thus, transduction of (a) T cell(s), preferably (a) CD8+ T cell(s), (a) CD4+ T cell(s), (a) CD3+ T cell(s), (a) γδ T cell(s) or (a) natural killer (NK) T cell(s), most preferably (a) CD8+ T cell(s), with CXCR6 will advantageously result in an improved adoptive T cell therapy. Accordingly, the present invention relates to a vector capable of transducing (a) T cell(s), preferably (a) CD8+ T cell(s), (a) CD4+ T cell(s), (a) CD3+ T cell(s), (a) γδ T cell(s) or (a) natural killer (NK) T cell(s), most preferably (a) CD8+ T cell(s), comprising/ which comprise a nucleic acid sequence encoding CXCR6 or a fragment thereof, which is characterized by having CXCR6 activity.

In the context of the present invention the vector may comprise a nucleic acid sequence, which encodes a fragment/polypeptide part of the full length chemokine receptor 6 (CXCR6). Thus, the chemokine receptor 6 (CXCR6), which is comprised in the herein provided vector is a fragment/polypeptide part of the full length CXCR6. The nucleic acid sequence encoding the full length chemokine receptor 6 (CXCR6) is shown herein as SEQ ID NO: 1 (human) and 3 (murine/mouse). The amino acid sequences of murine/mouse and human full length CXCR6 are shown herein as SEQ ID NOs: 4 (murine/mouse) and 2 (human), respectively (the Uni Prot Entry number of the human full length CXCR6 is 000574 (accession number with the entry version number 139 and version 1 of the sequence. The Uni Prot Entry number of the mouse full length CXCR6 is Q9EQ16 (accession number with the entry version number 111 and version 1 of the sequence)).

In the context of the present invention, the nucleic acid sequence encodes "a chemokine receptor 6 (CXCR6)". The term "chemokine receptor 6 (CXCR6)" and its scientific meaning relating to structure and function are well known in the art and is used accordingly in the context of the present invention (Shimaoka et al., J Leukoc Biol. 75(2) (2004), 267-274; Alkhatib G. et al., Nature 388(6639) (1997), 238; Paust et al., Nat Immunol. 11(12) (2010), 1127-1135). The function of the chemokine receptor 6 (CXCR6) within the vector of the present invention is to act as an attractor and a connector between a cell, preferably a T cell such as a CD8+ T cell, a CD4+ T cell, a CD3+ T cell, a γδ T cell or a natural killer (NK) T cells, most preferably a CD8+ T cell, that is to be transduced by a nucleic acid sequence expressing said chemokine receptor 6 (CXCR6) and target cell that (over-) expresses the chemokine (C-X-C motif) ligand 16 (CXCL16). The nucleic acid sequences of the full length CXCL16 is shown herein as SEQ ID NO: 5 (human) and 7 (murine/mouse). The amino acid sequences of murine/ mouse and human full length CXCL16 are shown herein as SEQ ID NOs: 8 (murine/mouse) and 6 (human), respectively (the Uni Prot Entry number of the human full length CXCL16 is Q9H2A7 (accession number with the entry version number 129 and version 4 of the sequence). The Uni Prot Entry number of the mouse full length CXCL16 is Q8BSU2 (accession number with the entry version number 103 and version 2 of the sequence)). Thus, the transduced T cell(s) expressing a chemokine receptor 6 (CXCR6) encoded by a nucleic acid sequence described herein is capable of migrating towards and binding to (a) target cell(s) that (over-) expresses CXCL16 such as, e.g., progenitor disease cells, primary cell lines, epithelial cells, neuronal cells, lymphoid lineage cells, stem cells or tumor cells.

The term "migrating" in the context of the present invention, refers to the capability of (transduced) T cells, which are characterized by (over-) expressing the CXCR6 towards (transduced) cells that (over-) express CXCL16 such as, e.g., progenitor disease cells, primary cell lines, epithelial cells, neuronal cells, lymphoid lineage cells, stems or tumor cells. The migration capacity of the target cells can be measured by flow cytometry, ELISA, microscopy or any other suitable device or system (Justus et al., J. Vis. Exp. (88) (2014), e51046, doi:10.3791/51046). In brief, such cell migration assays work as follows: transduced T cells (e.g. CD8+ T cells) are labelled with a suitable fluorescent dye and seeded in serum free medium in the upper well of a transwell insert in a 96 well plate. Recombinant CXCL16 is added to the lower chamber. Migration of cells is allowed at 37° C. Thereafter, cells reaching the lower well are quantified. Methods to measure migration are extensively known in the literature (Valster A. et al., Methods 37(2) (2005), 208-215) and include transwell-assays, confocal microscopy and flow cytometry for in vitro analysis, while flow cytometry, bioluminescence imaging and immunohistochemistry are used for in vivo analysis (see also Example section 2.5, infra, for further details).

The term "binding" in the context of the present invention, refers to the capability of the chemokine receptor 6 (CXCR6) to associate with the target cell, which is characterized by (over-) expressing CXCL16, for example via covalent or non-covalent interactions. A "covalent" interaction is a form of chemical bonding that is characterized by the sharing of pairs of electrons between atoms, or between atoms and other covalent bonds. Covalent bonding includes many kinds of interaction well-known in the art such as, e.g., σ-bonding, π-bonding, metal to non-metal bonding, agostic interactions and three-center two-electron bonds. A "non-covalent" bond is a chemical bond that does not involve the sharing of pairs of electrons. Non-covalent bonds are critical in maintaining the three-dimensional structure of large molecules, such as proteins and nucleic acids, and are involved in many biological processes in which molecules bind specifically but transiently to one another. There are several types of non-covalent bonds, such as hydrogen bonding, ionic interactions, Van-der-Waals interactions, charge-charge, charge-dipole, dipole-dipole bonds and hydrophobic bonds. Non-covalent interactions often involve several different types of non-covalent bonds working in concert, e.g., to keep a ligand in position on a target binding site on the cell membrane. An interaction may occur with a group such as a charge or a dipole, which may be present many times at the surface of the cell membrane. Preferably, the interaction (i.e. the binding) occurs at a defined site (involves a specific cell membrane constituent/epitope) of the cell membrane, and goes along with the formation of at least one interaction, preferably the formation of a network of several specific interactions. Even more preferably, the binding is specific for the target cell, i.e. the binding occurs at the cell membrane of the target cell but not, or not significantly, at the cell membrane of a non-target cell.

In the context of the present invention, the vector capable of transducing cells, comprises a nucleic acid sequence selected from the group consisting of SEQ ID NOs: 1 (human) and 3 (murine/mouse) or a nucleic acid sequence, which is at least 84%, 85%, 86%, 87%, 88%, 89%, 90%, 91%, 92%, 93%, 94%, 95%, 96%, 97%, 98% or 99% identical to the sequence of SEQ ID NOs: 1 (human) or 3 (murine/mouse) and which is characterized by having a chemokine receptor 6 (CXCR6) activity. Accordingly, also encompassed by the present invention are nucleic acid molecules, nucleic acid sequences or sequence segments having at least 84%, 85%, 86%, 87%, 88%, 89%, 90%, 91%, 92%, 93%, 94%, 95%, 96%, 97%, 98% or 99% identity with the nucleic acid molecule/nucleic acid sequence depicted in SEQ ID NOs: 1 (human) or 3 (murine/mouse). Such variant molecules may be splice forms or homologous molecules from other specifies. It will be appreciated that these variant nucleic acid molecule/nucleic acid sequences nonetheless have to encode an amino acid sequence having the indicated function, i.e. the sequence encoded by a variant of SEQ ID NOs: 1 (human) or 3 (murine/mouse) has to be characterized by having a chemokine receptor 6 (CXCR6) activity as defined herein below.

Accordingly, in the context of the present invention the nucleic acid sequence may be SEQ ID NOs: 1 (human) and 3 (murine/mouse) or a nucleic acid sequence, which is at least 84%, 85%, 86%, 87%, 88%, 89%, 90%, 91%, 92%, 93%, 94%, 95%, 96%, 97%, 98% or 99% identical to the sequence of SEQ ID NOs: 1 (human) or 3 (murine/mouse). If the herein provided vector capable of transducing (a) T cell(s), preferably (a) CD8+ T cell(s), (a) CD4+ T cell(s), (a) CD3+ T cell(s), (a) γδ T cell(s) or (a) natural killer (NK) T cell(s), most preferably (a) CD8+ T cell(s), comprises a nucleic acid sequence selected from the group consisting of SEQ ID NOs: 1 (human) and 3 (murine/mouse) or a nucleic acid sequence, which is at least 84%, 85%, 86%, 87%, 88%, 89%, 90%, 91%, 92%, 93%, 94%, 95%, 96%, 97%, 98% or 99% identical to the sequence of SEQ ID NOs: 1 (human) or 3 (murine/mouse), then said nucleic acid sequence is characterized by having a chemokine 6 receptor (CXCR6) activity. The chemokine 6 receptor (CXCR6) activity is defined by the ability to migrate towards a CXCL16 gradient orchestered by CXCL16-producing cells in vitro and in vivo and allowing the accumulation of CXCR6-positive T cells at the target site, i.e. tumor site and/or by the ability to mediate adhesion directly by CXCL16-binding or indirectly through integrine activation to CXCL16-producing tumor cells, thereby increasing tumor cell recognition. Methods to measure migration are extensively known in the literature (Valster A. et al., Methods 37(2) (2005), 208-215) and include transwell-assays, confocal microscopy and flow cytometry for in vitro analysis, while flow cytometry, bioluminescence imaging and immunohistochemistry are used for in vivo analysis.

In accordance with the present invention, the term "at least % identical to" in connection with nucleic acid sequences/nucleic acid molecules describes the number of matches ("hits") of identical nucleic acids of two or more aligned nucleic acid sequences as compared to the number of nucleic acid residues making up the overall length of the amino acid sequences (or the overall compared part thereof). In other terms, using an alignment, for two or more sequences or subsequences, the percentage of nucleic acid residues that are the same (e.g. at least 84%, 85%, 86%, 87%, 88%, 89%, 90%, 91%, 92%, 93%, 94%, 95%, 96%, 97%, 98% or 99% identity) may be determined, when the (sub)sequences are compared and aligned for maximum correspondence over a window of comparison, or over a designated region as measured using a sequence comparison algorithm as known in the art, or when manually aligned and visually inspected. Preferred nucleic acids in accordance with the invention are those where the described identity exists over a region that is at least 100 to 150 nucleotides in length, more preferably, over a region that is at least 200 to 400 nucleotides in length. More preferred nucleic acids in accordance with the present invention are those having the described sequence identity over the entire length of the nucleic acid sequence shown in SEQ ID NO: 1 (human) or 3 (murine/mouse).

It is well known in the art how to determine percent sequence identity between/among sequences using, for example, algorithms such as those based on CLUSTALW computer program (Thompson Nucl. Acids Res. 2 (1994), 4673-4680) or FASTA (Pearson and Lipman, Proc. Natl. Acad. Sci., 1988, 85; 2444). Although the FASTA algorithm typically does not consider internal non-matching deletions or additions in sequences, i.e., gaps, in its calculation, this can be corrected manually to avoid an overestimation of the % sequence identity. CLUSTALW, however, does take sequence gaps into account in its identity calculations. Also available to those having skill in this art are the BLAST and BLAST 2.0 algorithms (Altschul, Nucl. Acids Res., 25 (1977), 3389). The BLASTN program for nucleic acid sequences uses as default a word length (W) of 11, an expectation (E) of 10, M=5, N=4, and a comparison of both strands. For amino acid sequences, the BLASTP program uses as default a word length (W) of 3, and an expectation (E) of 10. The BLOSUM62 scoring matrix (Henikoff, Proc. Natl. Acad. Sci., 89 (1989), 10915) uses alignments (B) of 50, expectation (E) of 10, M=5, N=4, and a comparison of both strands. All those programs may be used for the purposes of the present invention. However, preferably the BLAST program is used. Accordingly, all the nucleic acid molecules having the prescribed function and further having a sequence identity of at least 84%, 85%, 86%, 87%, 88%, 89%, 90%, 91%, 92%, 93%, 94%, 95%, 96%, 97%, 98% or 99% as determined with any of the above recited or further programs available to the skilled person and preferably with the BLAST program fall under the scope of the invention.

In accordance with the present invention, nucleic acid sequences, which are also referred to herein as polynucleotides or nucleic acid molecules, include DNA, such as cDNA or genomic DNA, and RNA. It is understood that the term "RNA" as used herein comprises all forms of RNA including mRNA, tRNA and rRNA but also genomic RNA, such as in case of RNA of RNA viruses. Preferably, embodiments reciting "RNA" are directed to mRNA. Further included are nucleic acid mimicking molecules known in the art such as synthetic or semi-synthetic derivatives of DNA or RNA and mixed polymers, both sense and antisense strands. They may contain additional non-natural or derivatized nucleotide bases, as will be readily appreciated by those skilled in the art. Such nucleic acid mimicking molecules or nucleic acid derivatives according to the invention include peptide nucleic acid (PNA), phosphorothioate nucleic acid, phosphoramidate nucleic acid, 2'-O-methoxy-ethyl ribonucleic acid, morpholino nucleic acid, hexitol nucleic acid (HNA) and locked nucleic acid (LNA), an RNA derivative in which the ribose ring is constrained by a methylene linkage between the 2'-oxygen and the 4'-carbon (see, for example, Braasch and Corey, Chemistry & Biology 8 (2001), 1-7). PNA is a synthetic DNA-mimic with an amide backbone in place of the sugar-phosphate backbone of DNA or RNA, as described by Nielsen et al., Science 254 (1991):1497; and Egholm et al., Nature 365(1993), 666.

The nucleic acid molecules/nucleic acid sequences of the invention may be of natural as well as of synthetic or semi-synthetic origin. Thus, the nucleic acid molecules may, for example, be nucleic acid molecules that have been synthesized according to conventional protocols of organic chemistry. The person skilled in the art is familiar with the preparation and the use of such nucleic acid molecules (see, e.g., Sambrook and Russel "Molecular Cloning, A Laboratory Manual", Cold Spring Harbor Laboratory, N.Y. (2001)).

The term comprising, as used herein, denotes that further sequences, components and/or method steps can be included in addition to the specifically recited sequences, components and/or method steps. However, this term also encompasses that the claimed subject-matter consists of exactly the recited sequences, components and/or method steps.

In those embodiments where the nucleic acid molecule comprises (rather than consists of) the recited sequence, additional nucleotides extend over the specific sequence either on the 5' end or the 3' end, or both. Those additional nucleotides may be of heterologous or homologous nature. In the case of homologous sequences, these sequences may comprise up to 1500 nucleotides at the 5' and/or the 3' end, such as e.g. up to 1000 nucleotides, such as up to 900 nucleotides, more preferably up to 800 nucleotides, such as up to 700 nucleotides, such as e.g. up to 600 nucleotides, such as up to 500 nucleotides, even more preferably up to 400 nucleotides, such as up to 300 nucleotides, such as e.g. up to 200 nucleotides, such as up to 100 nucleotides, more preferably up to 50 nucleotides, such as up to 40 nucleotides such as e.g. up to 30 nucleotides, such as up to 20 nucleotides, more preferably up to 10 nucleotides and most preferably up to 5 nucleotides at the 5' and/or the 3' end. The term "up to [ . . . ] nucleotides", as used herein, relates to a number of nucleotides that includes any integer below and including the specifically recited number. For example, the term "up to 5 nucleotides" refers to any of 1, 2, 3, 4 and 5 nucleotides. Furthermore, in the case of homologous sequences, those embodiments do not include complete genomes or complete chromosomes.

Additional heterologous sequences may, for example, include heterologous promoters, which are operatively linked to the coding sequences of the invention, as well as further regulatory nucleic acid sequences well known in the art and described in more detail herein below. Thus, in the context of the present invention, the nucleic acid sequences may be under the control of regulatory sequences. Accordingly, in the context of the present invention, the vector of the present invention further comprises a regulatory sequence, which is operably linked to the nucleic acid sequences described herein. For example, promoters, transcriptional enhancers and/or sequences, which allow for induced expression of the CXCR6 described herein may be employed. In the context of the present invention, the nucleic acid molecules are expressed under the control of a constitutive or an inducible promoter. Suitable promoters are e.g. the CMV promoter (Qin et al., PLoS One 5(5) (2010), e10611), the UBC promoter (Qin et al., PLoS One 5(5) (2010), e10611), PGK (Qin et al., PLoS One 5(5) (2010), e10611), the EF1A promoter (Qin et al., PLoS One 5(5) (2010), e10611), the CAGG promoter (Qin et al., PLoS One 5(5) (2010), e10611), the SV40 promoter (Qin et al., PLoS One 5(5) (2010), e10611), the COPIA promoter (Qin et al., PLoS One 5(5) (2010), e10611), the ACT5C promoter (Qin et al., PLoS One 5(5) (2010), e10611), the TRE promoter (Qin et al., PLoS One. 5(5) (2010), e10611), the Oct3/4 promoter (Chang et al., Molecular Therapy 9 (2004), S367-S367 (doi: 10.1016/j.ymthe.2004.06.904)), or the Nanog promoter (Wu et al., Cell Res. 15(5) (2005), 317-24).

The term "regulatory sequence" refers to DNA sequences, which are necessary to effect the expression of coding sequences to which they are ligated. The nature of such control sequences differs depending upon the host organism. In prokaryotes, control sequences generally include (a) promoter(s), (a) ribosomal binding site(s), and (a) terminator(s). In eukaryotes generally control sequences include (a) promoter(s), (a) terminator(s) and, in some instances, (an) enhancer(s), (a) transactivator(s) or (a) transcription factor(s). The term "control sequence" is intended to include, at a minimum, all components the presence of which are necessary for expression, and may also include additional advantageous components.

Furthermore, it is envisaged for further purposes that nucleic acid molecules may contain, for example, thioester bonds and/or nucleotide analogues. Said modifications may be useful for the stabilization of the nucleic acid molecule against endo- and/or exonucleases in the transduced T cell. Said nucleic acid molecules may be transcribed by an appropriate vector containing a chimeric gene, which allows for the transcription of said nucleic acid molecule in the transduced T cell. In this respect, it is also to be understood that such polynucleotide can be used for "gene targeting" or "gene therapeutic" approaches. In another embodiment said nucleic acid sequences are labeled. Methods for the detection of nucleic acids are well known in the art, e.g., Southern and Northern blotting, PCR or primer extension. This embodiment may be useful for screening methods for verifying successful introduction of the nucleic acid sequences described above during gene therapy approaches. Said nucleic acid sequence(s) may be a recombinantly produced chimeric nucleic acid sequence comprising any of the aforementioned nucleic acid sequences either alone or in combination. In the context of the present invention, the nucleic acid molecule is part of a vector of the present invention.

The present invention therefore also relates to (a) vector(s) comprising the nucleic acid molecule described in the present invention. Herein the term "vector" relates to a circular or linear nucleic acid molecule, which can autonomously replicate in a host cell (i.e. in a transduced T cell) into which it has been introduced. The "vector" as used herein particularly refers to a plasmid, a cosmid, a virus, a bacteriophage and other vectors commonly used in genetic engineering. In the context of the present invention, the vector of the invention is suitable for the transformation of (a) T cell(s), preferably of (a) CD8+ T cell(s), (a) CD4+ T cell(s), (a) CD3+ T cell(s), (a) γδ T cell(s) or (a) natural killer (NK) T cell(s), most preferably (a) CD8+ T cell(s). Accordingly, in one aspect of the invention, the vector as provided herein is an expression vector. Expression vectors have been widely described in the literature. In particular, the herein provided vector preferably comprises a recombinant polynucleotide (i.e. a nucleic acid sequence encoding the chemokine receptor 6 (CXCR6) or a fragment thereof, which is characterized by having a CXCR6 activity as described herein) as well as (an) expression control sequence(s) operably linked to the nucleotide sequence to be expressed. The vector as provided herein preferably further comprises (a) promoter(s). The herein described vector may also comprise a selection marker gene and a replication-origin ensuring replication in the host (i.e. the transduced T cell). Moreover, the herein provided vector may also comprise a termination signal for transcription. Between the promoter and the termination signal there is preferably at least one restriction site or a polylinker, which enables the insertion of a nucleic acid molecule (e.g. a nucleic acid sequence encoding the CXCR6 described herein) desired to be expressed. The skilled person knows how such insertion can be put into practice. Examples of vectors suitable to comprise a nucleic acid molecule of the present invention to form the vector of the present invention are known in the art. For example, in context of the invention suitable vectors include cosmids, plasmids (e.g., naked or contained in liposomes) and viruses (e.g., lentiviruses, retroviruses, adenoviruses, and adeno-associated viruses) that incorporate the nucleic acid molecule of the invention (i.e. the nucleic acid sequence encoding the chemokine receptor 6 (CXCR6) or a fragment thereof, which is characterized by having a CXCR6 activity as described herein). Preferably, the vector of the present invention is a viral vector. More preferably, the vector of the present invention is a lentiviral vector, and even more preferably, the vector of the present invention is a retroviral vector (e.g. the pMP71 vector). Accordingly, in the context of the present invention, the vector is a lentiviral vector or a retroviral vector. The vector of the present invention allows for constitutive or conditional expression of the nucleic acid sequence of the present invention encoding the chemokine receptor 6 (CXCR6). In this context, suitable retoviral vectors for the expression of the CXCR6 are known in the art such as SAMEN CMV/SRa (Clay et al., J. Immunol. 163 (1999), 507-513), LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl. Acad. Sci. USA 83 (1986), 6563-6567), pDOL (Desiderio, J. Exp. Med. 167 (1988), 372-388), N2 (Kasid et al., Proc. Natl. Acad. Sci. USA 87 (1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7 (1996), 1123-1129), pG1XsNa (Taylor et al., J. Exp. Med. 184 (1996), 2031-2036), LCNX (Sun et al., Hum. Gene Ther. 8 (1997), 1041-1048), SFG (Gallardo et al., Blood 90 (1997), 1041-1048), LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sci. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J. Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423), or pMX (de Witte et al., J. Immunol. 181 (2008), 5128-5136). Further, in the context of the present invention suitable lentiviral vectors for the expression of the chemokine receptor 6 (CXCR6) as encoded by the nucleic acid sequence of the present invention are, e.g. PL-SIN lentiviral vector (Hotta et al., Nat Methods. 6(5) (2009), 370-376), p156RRL-sinPPT-CMV-GFP-PRE/Nhel (Campeau et al., PLoS One 4(8) (2009), e6529), pCMVR8.74 (Addgene Catalogoue No.:22036), FUGW (Lois et al., Science 295(5556) (2002), 868-872, pLVX-EF1 (Addgene Catalogue No.: 64368), pLVE (Brunger et al., Proc Natl Acad Sci USA 111(9) (2014), E798-806), pCDH1-MCS1-EF1 (Hu et al., Mol Cancer Res. 7(11) (2009), 1756-1770), pSLIK (Wang et al., Nat Cell Biol. 16(4) (2014), 345-356), pLJM1 (Solomon et al., Nat Genet. 45(12) (2013), 1428-30), pLX302 (Kang et al., Sci Signal. 6(287) (2013), rs13), pHR-IG (Xie et al., J Cereb Blood Flow Metab. 33(12) (2013), 1875-85), pRRLSIN (Addgene Catalogoue No.: 62053), pLS (Miyoshi et al., J Virol. 72(10) (1998), 8150-8157), pLL3.7 (Lazebnik et al., J Biol Chem. 283(7) (2008), 11078-82), FRIG (Raissi et al., Mol Cell Neurosci. 57 (2013), 23-32), pWPT (Ritz-Laser et al., Diabetologia. 46(6) (2003), 810-821), pBOB (Man et al., J Mol Neurosci. 22(1-2) (2004), 5-11), or pLEX (Addgene Catalogue No.: 27976).

The invention also relates to (a) transduced T cell(s), preferably (a) CD8+ T cell(s), (a) CD4+ T cell(s), (a) CD3+ T cell(s), (a) γδ T cell(s) or (a) natural killer (NK) T cell(s), most preferably (a) CD8+ T cell(s), expressing a chemokine receptor 6 (CXCR6) encoded by a nucleic acid sequence of the present invention. Accordingly, the invention refers to (a) T cell(s), preferably (a) CD8+ T cell(s), (a) CD4+ T cell(s), (a) CD3+ T cell(s), (a) γδ T cell(s) or (a) natural killer (NK) T cell(s), most preferably (a) CD8+ T cell(s), transduced with a vector expressing a chemokine receptor (CXCR6) encoded by a nucleic acid sequence selected from the group consisting of (a) a nucleic acid sequence of SEQ ID NO: 1 (human) or 3 (murine/mouse); and (b) a nucleic acid sequence, which is at least 84%, 85%, 86%, 87%, 88%, 89%, 90%, 91%, 92%, 93%, 94%, 95%, 96%, 97%, 98% or 99% identical to the sequence of SEQ ID NO: 1 (human) or 3 (murine/mouse) and which is characterized by having a chemokine receptor 6 (CXCR6) activity. Accordingly, in the context of the present, the transduced T cell(s) may comprise a nucleic acid sequence of the present invention encoding the chemokine receptor 6 (CXCR6) or a vector of the present invention, which expresses a chemokine receptor 6 (CXCR6) as encoded by a nucleic acid sequence of the present invention. Thus, in the context of the present invention the transduced T cell relates to a transduced T cell, preferably a CD8+ T cell, CD4+ T cell, a CD3+ T cell, a γδ T cell or a natural killer (NK) T cell, most preferably a CD8+ T cell, expressing a chemokine receptor 6 (CXCR6) encoded by a nucleic acid sequence selected from the group consisting of: (a) a nucleic acid sequence of SEQ ID NO: 1 (human) or 3 (murine/mouse); and (b) a nucleic acid sequence, which is at least 84%, 85%, 86%, 87%, 88%, 89%, 90%, 91%, 92%, 93%, 94%, 95%, 96%, 97%, 98% or 99% identical to the sequence of SEQ ID NO: 1 (human) or 3 (murine/mouse) and which is characterized by having a chemokine receptor 6 (CXCR6) activity.

In the context of the present, the term "transduced T cell" relates to a genetically modified T cell (i.e. a T cell wherein a nucleic acid molecule has been introduced deliberately). The herein provided transduced T cell may comprise the vector of the present invention. In the context of the present invention, the term "transduced T cell" refers to (a) T cell(s), preferably (a) CD8+ T cell(s), (a) CD4+ T cell(s), (a) CD3+ T cell(s), (a) γδ T cell(s) or (a) natural killer (NK) T cell(s), most preferably (a) CD8+ T cell(s), which is (are) characterized by not expressing a chemokine receptor 6 (CXCR6) encoded by a nucleic acid sequence selected from the group consisting of (a) a nucleic acid sequence of SEQ ID NO: 1 (human) or 3 (murine/mouse); and (b) a nucleic acid sequence, which is at least 84%, 85%, 86%, 87%, 88%, 89%, 90%, 91%, 92%, 93%, 94%, 95%, 96%, 97%, 98% or 99% identical to the sequence of SEQ ID NO: 1 (human) or 3 (murine/mouse) and which is characterized by having a chemokine receptor 6 (CXCR6) activity. Preferably, the herein provided transduced T cell comprises the nucleic acid sequence of the present invention encoding the chemokine receptor 6 (CXCR6) and/or the vector of the present invention. The transduced T cell of the invention may be a T cell, which transiently or stably expresses the foreign DNA (i.e. the nucleic acid molecule, which has been introduced into the T cell). In particular, the nucleic acid sequence of the present invention encoding the chemokine receptor 6 (CXCR6) can be stably integrated into the genome of the T cell by using a retroviral or lentiviral transduction. By using mRNA transfection, the nucleic acid molecule of the present invention encoding the CXCR6 described herein may be expressed transiently. Preferably, the herein provided transduced T cell has been genetically modified by introducing a nucleic acid molecule in the T cell via a viral vector (e.g. a retroviral vector or a lentiviral vector). The expression can be constitutive or constitutional, depending on the system used. The chemokine receptor 6 (CXCR6) is a seven transmembrane receptor thereby only a part of the receptor is accessible from the intracellular spaced. Once transduced in T cells, CXCR6 expression on the surface of the transduced T cell can be detected by flow cytometry or microscopy, using anti-CXCR6 antibodies. Antibodies for the detection of CXCR6 are extensively described in the literature and are commercially available. Exemplarily, anti-CXCR6 antibodies are available from R&D Systems, Inc., MN, USA under the catalogue number "MAB699". A full list of all commercially available anti-CXCR6 antibodies can be found at the Biocompare homepage (see http://www.biocompare.com/pfu/110447/soids/321781/Antibodies/CXCR6).

T cells are cells of the adaptive immune system recognizing their target in an antigen specific manner. These cells are characterized by surface expression of CD3 and a T cell receptor (TCR), recognizing a cognate antigen in the context of major histocompatibility complexes (MHC). T cells may be further subdivided in CD4+ or CD8+ T cells. CD4+ T cells recognize an antigen through their TCR in the context of MHC class II molecules which are predominantly expressed by antigen-presenting cells. CD8+ T cells recognize their antigen in the context of MHC class I molecules which are present on most cells of the human body. While the main function of CD4+ T cells is to provide "help", i.e. costimulatory factors to other antigen-specific cells such CD8+ T cells, CD8+ are directly cytotoxic to the target cell after TCR engagement.

Methods for detecting CD4+ and CD8+ T cells are well known to those skilled in the art and include flow cytometry, microscopy, immunohistochemistry, RT-PCR or western blot (Kobold, J Natl Cancer Inst (2015), 107; Kobold, J Natl Cancer Inst 107 (2015), 364).

The transduced T cell(s) of the present invention may be, e.g., (a) CD8+ T cell, (a) CD4+ T cell(s), (a) γδ T cell(s) or (a) natural killer (NK) T cell(s). Preferably, the transduced T cell of the present invention is (are) (a) transduced CD8+ T cell(s), (a) transduced CD4+ T cell(s), (a) γδ T cell(s) or (a) natural killer (NK) T cell(s), more preferably the transduced T cell(s) of the present invention is (are) (a) transduced CD8+ T cell(s) or (a) transduced CD4+ T cell(s), most preferably the transduced T cell is (are) (a) CD8+ T cell(s). Accordingly, in the context of the present invention, the transduced T cell is (are) most preferably (a) CD8+ T cell(s). Further, in the context of the present invention, it is also preferred that the transduced T cell(s) is (are) (an) autologous T cell(s).

Accordingly, in the context of the present invention, the transduced T cell is (are) preferably (a) transduced autologous CD8+ T cell(s), (a) transduced autologous CD4+ T cell(s), (a) transduced autologous γδ T cell or (a) transduced autologous natural killer (NK) T cell(s). In addition to the use of (an) autologous T cell(s) isolated from the subject, the present invention also comprehends the use of (an) allogeneic T cell(s). Accordingly, in the context of the present invention the transduced T cell may also be an allogeneic T cell, such as a transduced allogeneic CD8+ T cell. The use of allogeneic T cells is based on the fact that these cells can recognize a specific antigen epitope presented by foreign antigen-presenting cells (APC), provided that the APC express the MHC molecule, class I or class II, to which the specific responding cell population, i.e. T cell population is restricted, along with the antigen epitope recognized by the T cells. An "allogeneic T cell" is a T cell, of which the donor is of the same species as the recipient but genetically not identical with the recipient. Thus, the term allogeneic refers to cells coming from an unrelated donor individual/subject, which has human leukocyte antigen (HLA) compatible to the individual/subject, which will be treated by e.g. the herein described CXCR6 expressing transduced T cell. An "Autologous T cell" refers to (a) T cell(s), which is (are) isolated/obtained as described herein above from the subject to be treated with the transduced T cell described herein. Accordingly, (an) "autologous T cell(s)" is (are) (a) T cell(s), wherein donor and recipient is the same individual.

As described above, the transduced T cell(s) of the present invention is (are) transduced with a nucleic acid sequence expressing the herein provided chemokine receptor 6 (CXCR6). In the case of (a) cell(s) bearing natural anti-tumoral specificity such as tumor-infiltrating lymphocyte cells (TIL, Dudley et al., J Clin Oncol. 31(17) (2013), 2152-2159 (doi: 10.1200/JCO.2012.46.6441)) or (an) antigen-specific cell(s) sorted from the peripheral blood of patients for their tumor-specificity by flow cytometry (Hunsucker et al., Cancer Immunol Res. 3(3) (2015), 228-235 (doi: 10.1158/2326-6066.CIR-14-0001)), the cell(s) described herein would only be transduced with the chimeric receptor 6 (CXCR6) of the present invention. However, the transduced T cell(s) of the invention may be co-transduced with further nucleic acid molecules, e.g. with a nucleic acid sequence encoding a T cell receptor or a chimeric antigen receptor.

In accordance with this invention, the term "T cell receptor" is commonly known in the art. In particular, herein the term "T cell receptor" refers to any T cell receptor, provided that the following three criteria are fulfilled: (i) tumor specificity, (ii) recognition of (most) tumor cells, which means that an antigen or target should be expressed in (most) tumor cells and (iii) that the TCR matches to the HLA-type of the subject to be treated. In this context, suitable T cell receptors, which fulfill the above mentioned three criteria are known in the art such as receptors recognizing WT1 (Wilms tumor specific antigen 1; for sequence information(s) see, e.g., Sugiyama, Japanese Journal of Clinical Oncology 40 (2010), 377-87), MAGE (for sequence see, e.g., WO-A1 2007/032255 and PCT/US2011/57272), SSX (U.S. Provisional Application No. 61/388,983), NY-ESO-1 (for sequence information(s) see, e.g., PCT/GB2005/001924) and/or HER2neu (for sequence information(s) see WO-A1 2011/0280894).

The term "chimeric antigen receptor" or "chimeric receptor" is known in the art and refers to a receptor constituted of an extracellular portion of a single chain antibody domain fused by a spacer sequence to the signal domains of CD3z and CD28. Again, this chimeric antigen receptor should provide tumor specify and allow for the recognition of most tumor cells. Suitable chimeric receptors include: anti-EGFRv3-CAR (for sequence see WO-A1 2012/138475), anti-CD22-CAR (see WO-A1 2013/059593), anti-BCMA-CAR (see WO-A1 2013/154760), anti-CD19-CAR (see WO-A1 2012/079000 or US-A1 2014/0271635), anti-CD123-CAR (see US-A1 2014/0271582), anti-CD30-CAR (see WO-A1 2015/028444) or anti-Mesothelin-CAR (see WO-A1 2013/142034).

The present invention also relates to a method for the production of (a) transduced T cell(s) expressing a chemokine receptor 6 (CXCR6) encoded by a nucleic acid sequence of the present invention, comprising the steps of transducing (a) T cell(s), preferably (a) CD8+ T cell(s), (a) CD4+ T cell(s), (a) γδ T cell(s) or (a) natural killer (NK) T cell(s), most preferably (a) CD8+ T cell(s), with a vector of the present invention, culturing the transduced T cell(s) under conditions allowing the expressing of the CXCR6 in or on said transduced T cell(s) and recovering said transduced T cell(s).

In the context of the present invention, the transduced T cell(s) of the present invention is (are) preferably produced by/obtainable by the following process: (a) T cell(s), preferably (a) CD8+ T cell(s), (a) CD4+ T cell(s), (a) γδ T cell(s) or (a) natural killer (NK) T cell(s), most preferably (a) CD8+ T cell(s) is (are) isolated/obtained from a subject, preferably a human patient. Methods for isolating/obtaining (a) T cell(s), preferably (a) CD8+ T cell(s), (a) CD4+ T cell(s), (a) γδ T cell(s) or (a) natural killer (NK) T cell(s), most preferably (a) CD8+ T cell(s) from (a) patient(s) or from (a) donor(s) is (are) well known in the art and in the context of the present invention the T cell(s), preferably CD8+ T cell(s), CD4+ T cell(s), γδ T cell(s) or natural killer (NK) T cell(s), most preferably CD8+ T cell(s) from (a) subject(s)/patient(s) or from (a) donor(s) may be isolated by blood draw or removal of bone marrow. After isolating/obtaining (a) T cell(s) as a sample of the subject(s)/patient(s) or donor(s), the T cell(s) is (are) separated from the other ingredients of the sample. Several methods for separating T cell(s) from the sample is (are) known and include, without being limiting, e.g. leukapheresis for obtaining (a) T cell(s) from the peripheral blood sample from a patient or from a donor, isolating/obtaining T cells by using a FACSort apparatus, picking living of dead T cell(s) from fresh biopsy specimens harboring (a) living T cell(s) by hand or by using a micromanipulator (see, e.g., Dudley, Immunother. 26 (2003), 332-342; Robbins, Clin. Oncol. 29 (201 1), 917-924 or Leisegang, J. Mol. Med. 86 (2008), 573-58). Herein the term "fresh patient biopsy" refers to tissue, preferably tumor tissue, removed from a subject by surgical or any other known means as well as (a) tumor cell line(s) or (an) (isolated) cell(s) from a tumor tissue/tumor cell. The isolated/obtained T cell(s), preferably CD8+ T cell(s), CD4+ T cell(s), γδ T cell(s) or natural killer (NK) T cell(s), most preferably CD8+ T cell(s), is (are) subsequently cultivated and expanded, e.g., by using an anti-CD3 antibody, by using anti-CD3 and anti-CD28 monoclonal antibodies and/or by using an anti-CD3 antibody, an anti-CD28 antibody and in the presence of cytokines, e.g. interleukin-2 (IL-2) and/or interleukin-15 (IL-15) (see, e.g., Dudley, Immunother. 26 (2003), 332-342 or Dudley, Clin. Oncol. 26 (2008), 5233-5239).

In a subsequent step the T cell(s) is (are) artificially/genetically modified/transduced by methods known in the art (see, e.g., Lemoine, J Gene Med 6 (2004), 374-386). Methods for transducing (a) cell(s), particularly (a) T cell(s), is (are) known in the art and include, without being limited, in a case where nucleic acid or a recombinant nucleic acid is transduced, for example, an electroporation method, calcium phosphate method, cationic lipid method or liposome method. The nucleic acid to be transduced can be conventionally and highly efficiently transduced by using a commercially available transfection reagent, for example, Lipofectamine (manufactured by Invitrogen, catalogue no.: 11668027). In a case where a vector is used, the vector can be transduced in the same manner as the above-mentioned nucleic acid as long as the vector is a plasmid vector (i.e. a vector that is not a viral vector In the context of the present invention, the methods for transducing (a) T cell(s) include(s) retroviral or lentiviral T cell transduction as well as mRNA transfection. "mRNA transfection" refers to a method well known to those skilled in the art to transiently express a protein of interest, like in the present case the CXCR6, in (a) T cell(s) to be transduced. In brief (a) T cell(s) may be electroporated with the mRNA coding for the CXCR6 described herein by using an electroporation system (such as e.g. Gene Pulser, Bio-Rad) and thereafter cultured by standard cell (e.g. T cell) culture protocol as described above (see Zhao et al., Mol Ther. 13(1) (2006), 151-159.) Preferably, the transduced T cell(s) of the invention is (are) (a) CD8+ T cell(s), (a) CD4+ T cell(s), (a) γδ T cell(s) or (a) natural killer (NK) T cell(s), ormost preferably (a) CD8+ T cell(s), and is (are) generated by lentiviral, or most preferably retroviral T cell transduction.

In this context, suitable retroviral vectors for transducing (a) T cell(s) is (are) known in the art such as SAMEN CMV/SRa (Clay et al., J. Immunol. 163 (1999), 507-513), LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl. Acad. Sci. USA 83 (1986), 6563-6567), pDOL (Desiderio, J. Exp. Med. 167 (1988), 372-388), N2 (Kasid et al., Proc. Natl. Acad. Sci. USA 87 (1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7 (1996), 1123-1129), pG1XsNa (Taylor et al., J. Exp. Med. 184 (1996), 2031-2036), LCNX (Sun et al., Hum.

Gene Ther. 8 (1997), 1041-1048), SFG (Gallardo et al., Blood 90 (1997), LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sci. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J. Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423), or pMX (de Witte et al., J. Immunol. 181 (2008), 5128-5136). In the context of the present invention, suitable lentiviral vector for transducing T cells are, e.g. PL-SIN lentiviral vector (Hotta et al., Nat Methods. 6(5) (2009), 370-376), p156RRL-sinPPT-CMV-GFP-PRE/Nhel (Campeau et al., PLoS One 4(8) (2009), e6529), pCMVR8.74 (Addgene Catalogoue No.:22036), FUGW (Lois et al., Science 295(5556) (2002), 868-872, pLVX-EF1 (Addgene Catalogue No.: 64368), pLVE (Brunger et al., Proc Natl Acad Sci USA 111(9) (2014), E798-806), pCDH1-MCS1-EF1 (Hu et al., Mol Cancer Res. 7(11) (2009), 1756-1770), pSLIK (Wang et al., Nat Cell Biol. 16(4) (2014), 345-356), pLJM1 (Solomon et al., Nat Genet. 45(12) (2013), 1428-30), pLX302 (Kang et al., Sci Signal. 6(287) (2013), rs13), pHR-IG (Xie et al., J Cereb Blood Flow Metab. 33(12) (2013), 1875-85), pRRLSIN (Addgene Catalogoue No.: 62053), pLS (Miyoshi et al., J Virol. 72(10) (1998), 8150-8157), pLL3.7 (Lazebnik et al., J Biol Chem. 283(7) (2008), 11078-82), FRIG (Raissi et al., Mol Cell Neurosci. 57 (2013), 23-32), pWPT (Ritz-Laser et al., Diabetologia. 46(6) (2003), 810-821), pBOB (Man et al., J Mol Neurosci. 22(1-2) (2004), 5-11), or pLEX (Addgene Catalogue No.: 27976).

The transduced T cell/T cells of the present invention is/are preferably grown under controlled conditions, outside of their natural environment. In particular, the term "culturing" means that cells (e.g. the transduced T cell(s) of the invention), which are derived from multi-cellular eukaryotes, preferably from a human patient, are grown in vitro. Culturing cells is a laboratory technique of keeping cells alive, which are separated from their original tissue source. Herein, the transduced T cell(s) of the present invention is (are) cultured under conditions allowing the expression of the CXCR6 described herein in or on said transduced T cell(s). Conditions that allow the expression or a transgene (i.e. of the CXCR6 described herein) are commonly known in the art and include, e.g., agonistic anti-CD3- and anti-CD28 antibodies and the addition of cytokines such as interleukin 2 (IL-2), interleukin 7 (IL-7), interleukin 12 (IL-12) and/or interleukin 15 (IL-15). After expression of the CXCR6 described herein in the cultured transduced T cell(s), the transduced T cell(s) is (are) recovered (i.e. re-extracted) from the culture (i.e. from the culture medium).

Also encompassed by the invention is (are) (a) transduced T cell(s) expressing a chemokine receptor 6 (CXCR6) as encoded by a nucleic acid molecule of the invention produced by/obtainable by the method of the present invention.

Furthermore, the invention provides a pharmaceutical composition/medicament comprising (a) transduced T cell(s) expressing a chemokine receptor 6 (CXCR6) encoded by a nucleic acid sequence of the present invention or a transduced T cell as obtained by/produced by the method disclosed above. In the context of the present invention, said composition is a pharmaceutical composition further comprising, optionally, suitable formulations of carrier, stabilizers and/or excipients.

In accordance with the present invention, the term "medicament" is used interchangeably with the term "pharmaceutical composition" and relates to a composition for administration to a patient, preferably a human patient. Accordingly, the invention provides (a) transduced T cell(s), preferably (a) CD8+ T cell(s), (a) CD4+ T cell(s), (a) γδ T cell(s) or (a) natural killer (NK) T cell(s), most preferably (a) CD8+ T cell(s), expressing a chemokine receptor 6 (CXCR6) as encoded by a nucleic acid molecule of the invention, or produced/obtainable by the method of the present invention for use as a medicament. In the context of the present invention that medicament/pharmaceutical composition is to be administered to a patient from which the transduced T cell(s) was (were) isolated/obtained. In the context of the present invention, the patient refers to a human patient. Furthermore, in the context of the present invention that patient suffers from a disease characterized by CXCL16 overexpression. In the context of the present invention diseases that are characterized by CXCL16 overexpression are known in the art and include e.g. colorectal cancer (Wagsater et al., Int J Mol Med. 14(1) (2004), 65-69), brain cancer (Ludwig et al., J Neurochem. 93(5) (2005), 1293-1303), ovarian cancer (Son et al., Cancer Biol Ther. 6(8) (2007), 1302-1312), prostate cancer (Lu et al., Mol Cancer Res. 6(4) (2008), 546-554), pancreatic cancer (Wente et al., Int J Oncol. 33(2) (2008), 297-308), breast cancer (Matsumura et al., J Immunol. 181(5) (2008), 3099-3107), renal cancer (Gutwein et al., Eur J Cancer. 45(3) (2009), 478-89), nasopharyngeal carcinoma (Parsonage et al., Am J Pathol. 180(3) (2012), 1215-22), hepatocellular carcinoma (Gao et al., Cancer Res. 72(14) (2012), 3546-3556), gastric cancer (Xing et al., Hum Pathol. 43(12) (2012), 2299-2307), cervical cancer (Huang et al., Chin J Cancer. 32(5) (2013), 289-296), bladder cancer (Lee et al., Oncol Lett. 5(1) (2013), 229-235), lymphoma (Liu et al., Oncol Rep. 30(2) (2013), 783-792), sarcoma (Na et al., Hum Pathol. 45(4) (2014), 753-760), or lung cancer (Hu et al., PLoS One. 9(6) (2014), e990562014). Accordingly, in the context of the present invention, the disease characterized by CXCL16 overexpression refers in the context of the present invention to a disease selected from the group consisting of colorectal cancer, brain cancer, ovarian cancer, prostate cancer, pancreatic cancer, breast cancer, renal cancer, nasopharyngeal carcinoma, hepatocellular carcinoma, gastric cancer, cervical cancer, bladder cancer, lymphoma, sarcoma, and lung cancer.

In the context of the present invention the pharmaceutical composition that comprises (a) transduced T cell(s) of the present invention or (a) transduced T cell(s) produced by/obtainable by the method of the present invention is (are) to be administered in combination intervening treatment protocols. Examples of such intervening treatment protocols include but are not limited to, administration of pain medications, administration of chemotherapeutics, surgical handling of the disease or a symptom thereof. Accordingly the treatment regimens as disclosed herein encompass the administration of the transduced T cell(s) expressing a CXCR6 as described herein together with none, one, or more than one treatment protocol suitable for the treatment or prevention of a disease, or a symptom thereof, as described herein or as known in the art.

Accordingly, in the context of the present invention transduced T cell(s) expressing the chemokine receptor 6 (CXCR6) as encoded by a nucleic acid sequence of the present invention can be used for the treatment of a proliferative disease, preferably cancer. More preferably, the herein provided transduced T cell(s) expressing the chemokine receptor 6 (CXCR6) as described herein is (are) used for the treatment of a disease (preferably a cancer), which is characterized by CXCL16 overexpression. Cancer types that are preferably treated with the herein provided transduced T cell expressing the chemokine receptor 6 (CXCR6) are described herein above. Thus, the transduced T cell(s) expressing a chemokine receptor 6 (CXCR6) encoded by a nucleic acid sequence described herein can be used in a method of treating any disease where tumor cells overexpress CXCL16. The treatment method preferably involves cell collection by a method described above like isolating/collection of the cells by blood draw or removal of bone marrow. Subsequently, the isolated cell(s) is (are) modified virally or by mRNA electroporation with the fusion receptor (and optionally co-transduced with further nucleic acid molecules, e.g. with a nucleic acid sequence encoding (a) T cell receptor(s) or (a) chimeric receptor(s)). After cell expansion, as outlined above, the transduced T cell(s), preferably CD8+ T cell(s), CD4+ T cell(s), γδ T cell(s) or natural killer (NK) T cell(s), most preferably CD8+ T cell(s), is (are) transferred intravenously back to the patient. Moreover, the present invention provides a method for the treatment of diseases comprising the steps of isolating (a) T cell(s), preferably (a) CD8+ T cell(s), (a) CD4+ T cell(s), (a) γδ T cells or (a) natural killer (NK) T cell(s), most preferably (a) CD8+ T cell(s), from a subject, transducing said isolated T cell(s) with a nucleic acid encoding the chemokine receptor 6 (CXCR6) as described herein above, co-transducing said isolated T cell(s) with further nucleic acid molecules, e.g. with a nucleic acid sequence encoding (a) T cell receptor or (a) chimeric receptor(s) as described above, expanding the transduced T cell(s), and administering the transduced T cell(s) back to said subject. This treatment method described herein may be repeated e.g. one or two times per week The invention also relates to a method for treatment of a disease characterized by CXCL16 overexpression in a subject comprising the steps of
(a) isolating (a) T cell(s), preferably (a) CD8+ T cell(s), (a) CD4+ T cell(s), (a) γδ T cell(s) or (a) natural killer (NK) T cell(s), most preferably (a) CD8+ T cell(s), from a subject;
(b) transducing said isolated (a) T cell(s), e.g., (a) CD8+ T cell(s), with a vector comprising a nucleic acid sequence selected from the group consisting of:
  (i) a nucleic acid sequence of SEQ ID NOs: 1 or 3, and
  (ii) a nucleic acid sequence, which is at least 86%, 87%, 88%, 89%, 90%, 91%, 92%, 93%, 94%, 95%, 96%, 97%, 98% or 99% identical to the sequence of SEQ ID NOs: 1 or 3 and which is characterized by having a chemokine receptor 6 (CXCR6) activity; and
(c) administering said transduced T cell(s), e.g. CD8+ T cell(s), to said subject.

In the context of the present invention, said transduced T cell(s), e.g., CD8+ T cell(s), is (are) administered to said subject by intravenous infusion.

Moreover, the present invention provides a method for the treatment of a disease characterized by CXCL16 overexpression comprising the steps of
(a) isolating (a) T cell(s), preferably (a) CD8+ T cell(s), (a) CD4+ T cell(s), (a) γδ T cell(s) or (a) natural killer (NK) T cell(s), most preferably (a) CD8+ T cell(s), from a subject;
(b) transducing said isolated T cell(s), e.g., (a) CD8+ T cell(s), with a vector comprising a nucleic acid sequence selected from the group consisting of:
  (i) a nucleic acid sequence of SEQ ID NOs: 1 or 3, and
  (ii) a nucleic acid sequence, which is at least 84%, 85%, 86%, 87%, 88%, 89%, 90%, 91%, 92%, 93%, 94%, 95%, 96%, 97%, 98% or 99% identical to the sequence of SEQ ID NOs: 1 or 3 and which is characterized by having a chemokine receptor 6 (CXCR6) activity; and
(c) co-transducing said isolated T cell(s), e.g., (a) CD8+ T cell(s), with (a) T cell receptor(s);
(d) expanding the T cell(s), e.g., (a) CD8+ T cell(s), by, e.g., anti-CD3 and anti-CD28 antibodies; and
(e) administering the transduced T cell(s), e.g. CD8+ T cell(s), to said subject.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a subject and includes: (a) preventing and/or ameliorating a proliferative disease (preferably cancer) from occurring in a subject that may be predisposed to the disease; (b) inhibiting the disease, i.e. arresting its development, like the inhibition cancer progression; or (c) relieving the disease, i.e. causing regression of the disease, like the repression of cancer. Preferably, the term "treatment" as used herein relates to medical intervention of an already manifested disorder, like the treatment of a diagnosed cancer.

For the purposes of the present invention the "subject" (or "patient") may be a vertebrate. In context of the present invention, the term "subject" includes both humans and other animals, particularly mammals, and other organisms. Thus, the herein provided methods are applicable to both human therapy and veterinary applications. Accordingly, said subject may be an animal such as a mouse, rat, hamster, rabbit, guinea pig, ferret, cat, dog, chicken, sheep, bovine species, horse, camel, or primate. Preferably, the subject is a mammal. Most preferably the subject is a human being.

As described above, the present invention relates to a "pharmaceutical composition" comprising the herein provided transduced T cell expressing the chemokine receptor 6 (CXCR6) described herein (encoded by the nucleic acid molecule of the present invention). Said pharmaceutical composition may further comprise a pharmaceutically acceptable carrier, excipient and/or diluent. Examples of suitable pharmaceutical carriers are well known in the art and include phosphate buffered saline solutions, water, emulsions, such as oil/water emulsions, various types of wetting agents, sterile solutions etc. The carrier may be a solution that is isotonic with the blood of the recipient. Compositions comprising such carriers can be formulated by well known conventional methods. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. For example, the pharmaceutical composition of the invention may be administered to the subject at a dose of $10^4$ to $10^{10}$ T cells/kg body weight, preferably $10^5$ to $10^6$ T cells/kg body weight. In the context of the present invention the pharmaceutical composition may be administered in such a way that an upscaling of the T cells to be administered is performed by starting with a subject dose of about $10^5$ to $10^6$ T cells/kg body weight and then going up to dose of $10^{10}$ T cells/kg body weight. The pharmaceutical composition of the invention may be administered intravenously (i.e. by intravenous infusion) but also intraperitoneally, intrapleurally, intrathecally, subcutaneously or intranodally. Intravenous carriers include fluid and nutrient replenishers, electrolyte replenishers (such as those based on Ringer's dextrose), and the like preservatives and other additives may also be present in the pharmaceutical composition of the present invention, such as, e.g., antimicrobials, anti-oxidants, chelating agents, inert gases and the like.

The pharmaceutical composition of the present invention may be used in co-therapy in conjunction with, e.g., molecules capable of providing an activation signal for immune effector cells, for cell proliferation or for cell stimulation. Said molecule may be, e.g., a further primary activation signal for T cells (e.g. a further costimulatory molecule: molecules of B7 family, Ox40L, 4.1 BBL, CD40L, anti-CTLA-4, anti-PD-1), or a further cytokine interleukin (e.g., IL-2).

In context of the present invention, the components of the pharmaceutical composition to be used for therapeutic administration are preferably sterile. Sterility may readily be accomplished by, e.g., filtration through sterile filtration membranes (e.g., 0.2 micron membranes). The pharmaceutical composition of the present invention may be prepared by contacting the components of the pharmaceutical composition uniformly with liquid carriers. After its production, the pharmaceutical composition of the invention may be placed into a container having a sterile access port, for example, an intravenous solution bag or vial having a stopper pierceable by a hypodermic injection needle.

The invention also relates to a method for the treatment of diseases that are characterized by overexpressing CXCL16 such as, e.g., colorectal cancer, brain cancer, ovarian cancer, prostate cancer, pancreatic cancer, breast cancer, renal cancer, nasopharyngeal carcinoma, hepatocellular carcinoma, gastric cancer, cervical cancer, bladder cancer, lymphoma, sarcoma, or lung cancer comprising the administration of a transduced T cell as described herein to a subject. In the context of the present invention, said subject is a human (as explained above). In the context of the present invention, a method for the treatment of a disease is described that comprises the steps of isolating (a) T cell(s), preferably (a) CD8+ T cell(s), (a) CD4+ T cell(s), (a) γδ T cell(s) or (a) natural killer (NK) T cell(s), most preferably (a) CD8+ T cell(s), from a subject, transducing said isolated T cell(s) with a nucleic acid encoding the chemokine receptor 6 (CXCR6) as described herein above or with a vector comprising a nucleic acid encoding the CXCR6 as described herein above, and administering the transduced T cells to said subject. In the context of the present invention, said transduced T cells are administered to said subject by intravenous infusion. Moreover, the present invention provides a method for the treatment of diseases comprising the steps of isolating T cells, preferably CD8+ T cells, CD4+ T cells, γδ T cells or natural killer (NK) T cells, most preferably CD8+ T cells, from a subject, transducing said isolated T cells with a nucleic acid encoding the chemokine receptor 6 (CXCR6) as described herein above, co-transducing said isolated T cell(s) with further nucleic acid molecules, e.g. with a nucleic acid sequence encoding (a) T cell receptor(s) or (a) chimeric receptor(s) as described above, expanding the transduced cells, and administering the transduced cells back to said subject.

The above mentioned expanding step of the transduced T cell(s) may be performed in the presence of (stimulating) cytokines such as interleukin-2 (IL-2) and/or interleukin-15 (IL-15). In the context of the present invention, the expanding step may also be performed in the presence of interleukin-12 (IL-12), interleukin-7 (IL-7) and/or interleukin-21 (IL-21). In accordance with the present invention, the expanding step of the transduced T cell(s) may also be performed in the presence of anti-CD3 and/or anti-CD28 antibodies.

As described herein, the present invention relates to a kit comprising the nucleic acid molecule of the invention, the vector of the invention and/or the transduced T cell(s) of the invention. In the context of the present invention, a kit for incorporating a nucleic acid sequence selected from the group consisting of (a) a nucleic acid sequence of SEQ ID NO: 1, and (b) a nucleic acid sequence, which is at least 84%, 85%, 86%, 87%, 88%, 89%, 90%, 91%, 92%, 93%, 94%, 95%, 96%, 97%, 98% or 99% identical to the sequence of SEQ ID NO: 1 and which is characterized by having a chemokine receptor 6 (CXCR6) activity into a CD8+ T cell comprising a vector of the present invention is provided. Thus, the herein provided treatment methods may be realized by using this kit. Advantageously, the kit of the present invention further comprises optionally (a) reaction buffer(s), storage solutions (i.e. preservatives), wash solutions and/or remaining reagents or materials required for the conduction of the assays as described herein. Furthermore, parts of the kit of the invention can be packaged individually in vials or bottles or in combination in containers or multicontainer units. In addition, the kit may contain instructions for use. The manufacture of the kit of the present invention follows preferably standard procedures, which are known to the person skilled in the art. As mentioned above, the kit provided herein is useful for treating a subject, preferably a human patient, which has a disease that is characterized by over-expression of CXCL16 such as, e.g., colorectal cancer, brain cancer, ovarian cancer, prostate cancer, pancreatic cancer, breast cancer, renal cancer, nasopharyngeal carcinoma, hepatocellular carcinoma, gastric cancer, cervical cancer, bladder cancer, lymphoma, sarcoma, or lung cancer.

THE FIGURES SHOW

FIG. 1: CXCL16 induction by pancreatic cancer cells Panc02-OVA and T110299 upon IFN-γ or TNF-α stimulation Tumor cells (i.e. pancreatic cancer cell lines Panc02-OVA and T110299) ($0.01 \times 10^6$/well) were seeded in a 96-well plate (flat bottom) and stimulated with recombinant IFN-γ (20 ng/ml) or TNF-α (20 ng/ml) (Peprotech, Hamburg). Supernatants were harvested after 48 hours. CXCL16 secretion was measured with a CXCL16 ELISA kit (R&D Systems, Inc., MN, USA). As shown in the Figure, the pancreatic cancer cell lines Panc02-OVA and T110299 release CXCL16 in the presence and absence of IFN-γ and TNF-α in vitro.

Figure 2:
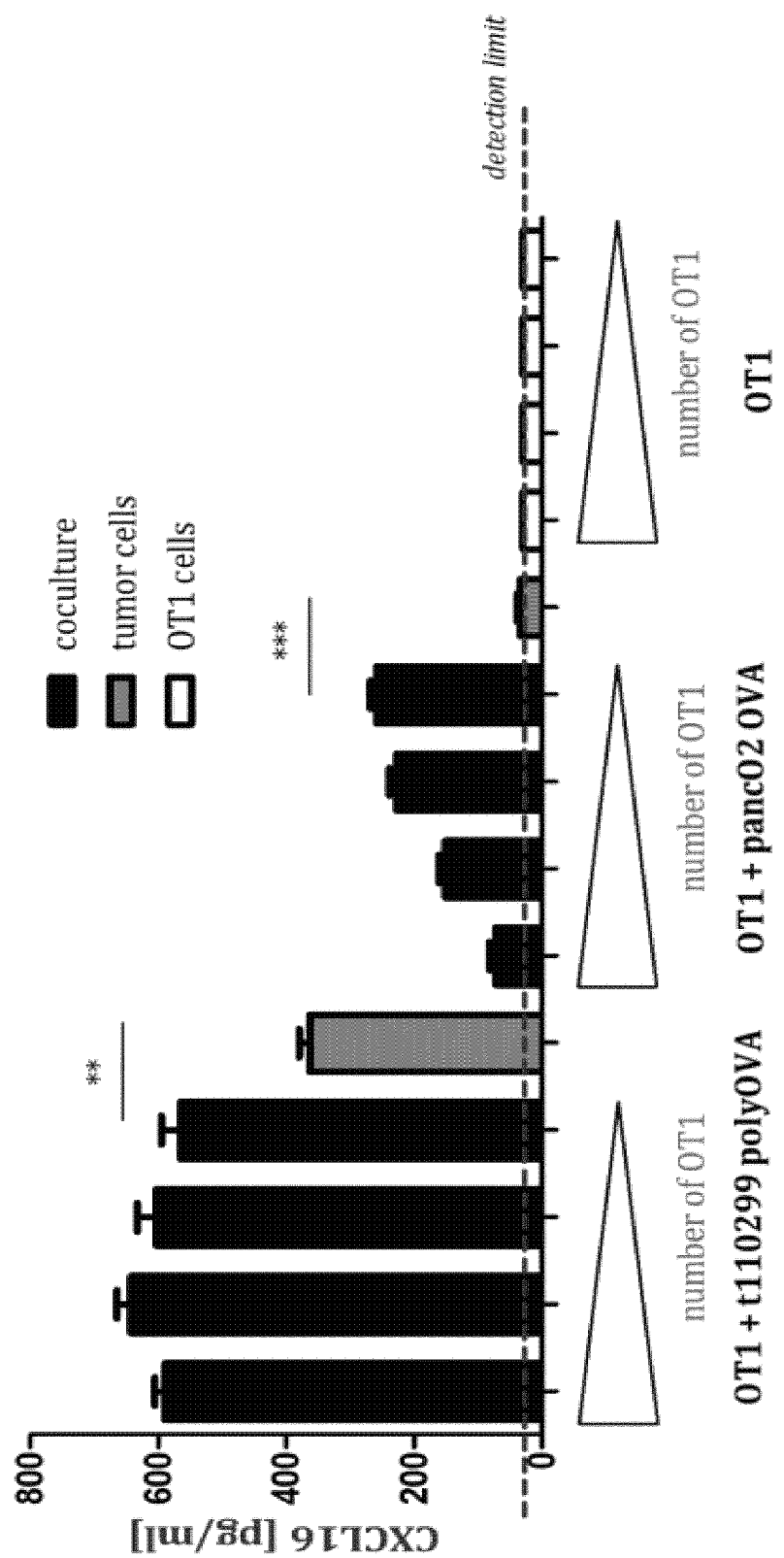

FIG. 2: Induction of CXCL16 from Panc02-OVA and T110299 pancreatic cancer cells upon co-culture with antigen-specific T cells The pancreatic cancer cell lines Panc02-OVA and T110299 ($0.03 \times 10^6$/well) were co-cultured ($0.03 \times 10^6$/well) with T cells (1:1-10:1 ratios) in 96-well plates (flat bottom). Supernatants were harvested after 48 hours. CXCL16 secretion was measured with a CXCL16 ELISA kit (R&D Systems, Inc., MN, USA). As shown in FIG. 2, the antigen recognition in the context of MHC by antigen-specific T cells (OVA-specific, OT-1 T cells) on the surface of pancreatic cancer cells Panc02-OVA and T110299 induces release of CXCL16 from the pancreatic cancer cells.

Figure 3A:
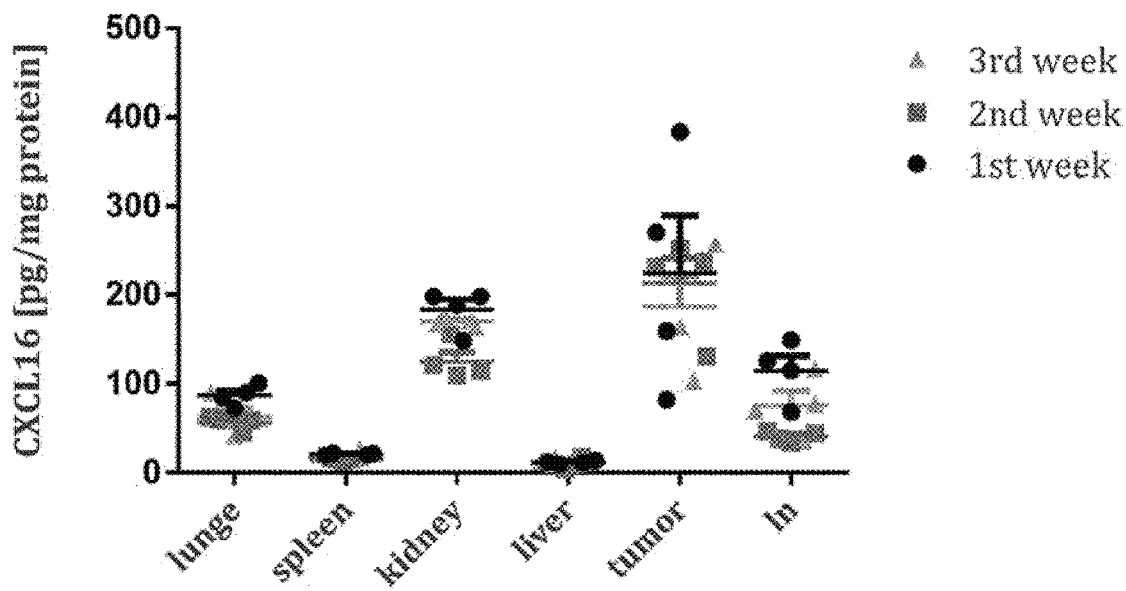
Figure 3B:
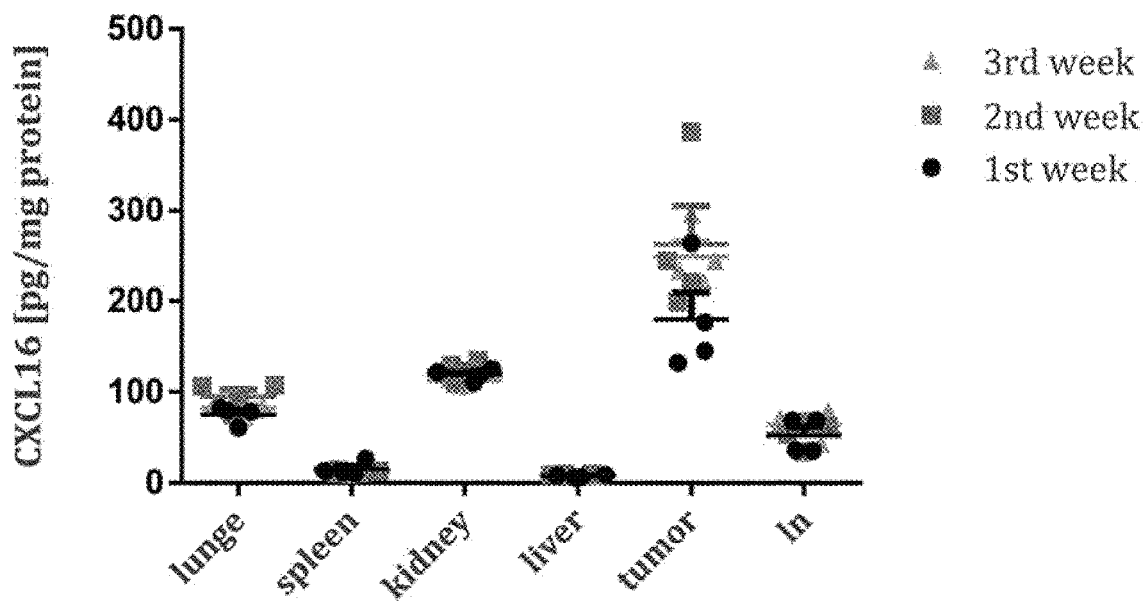

FIG. 3: Expression of CXCL16 in Panc02-OVA and T110299 tumor bearing mice

Expression of CXCL16 in tumor bearing mice was analyzed over time in different organs. Female C57BL/6J mice (4 per group) (Janvier, France (Cat. Number 2014-07-DE-RM-20)) were injected subcutaneously with Panc02-OVA (Jacobs et al. Int J Cancer 128 (2011), 128) or T110299 tumor cells (Düwell et al., Cell Death Differ 21(12) (2014), 1825-1837) at a concentration of $2 \times 10^6$ cells per mice. Organs and tumors were analyzed after one, two or three weeks of induction and frozen in liquid nitrogen. After determination of the protein content by the Bradford method (Bio Rad, München) CXCL16 expression was measured with a CXCL16 ELISA kit (R&D Systems, Inc., MN, USA). The tumor site was found to be the site with the highest CXCL16 expression both in Panc02-OVA and T110299 tumors.

Figure 4A:
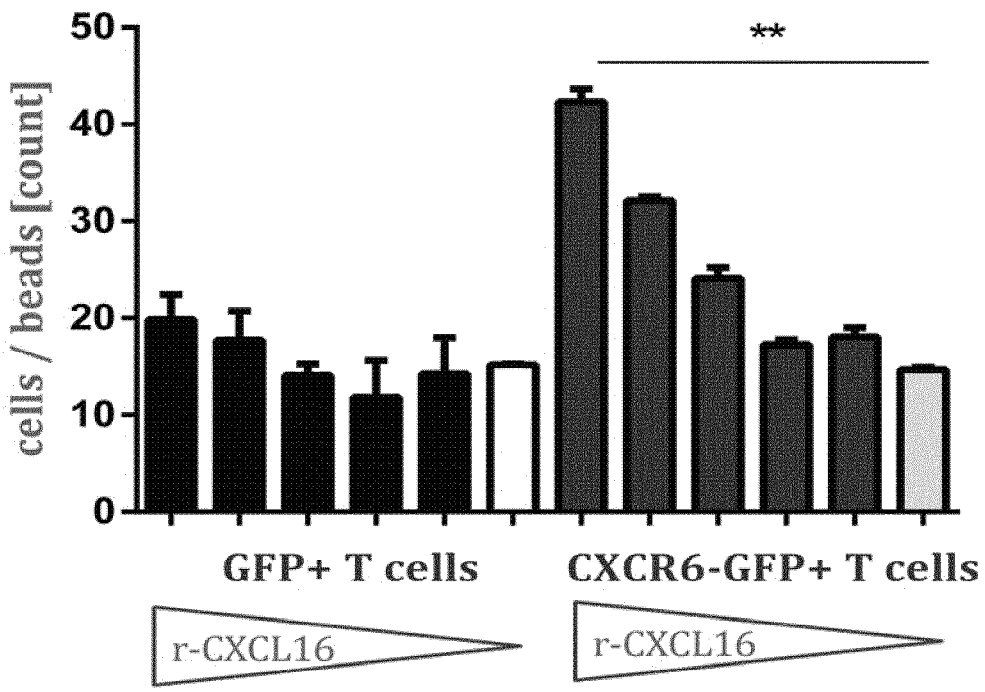

FIG. 4: Migration of CXCR6-transduced T cells towards a gradient of recombinant CXCL16

Figure 4B:
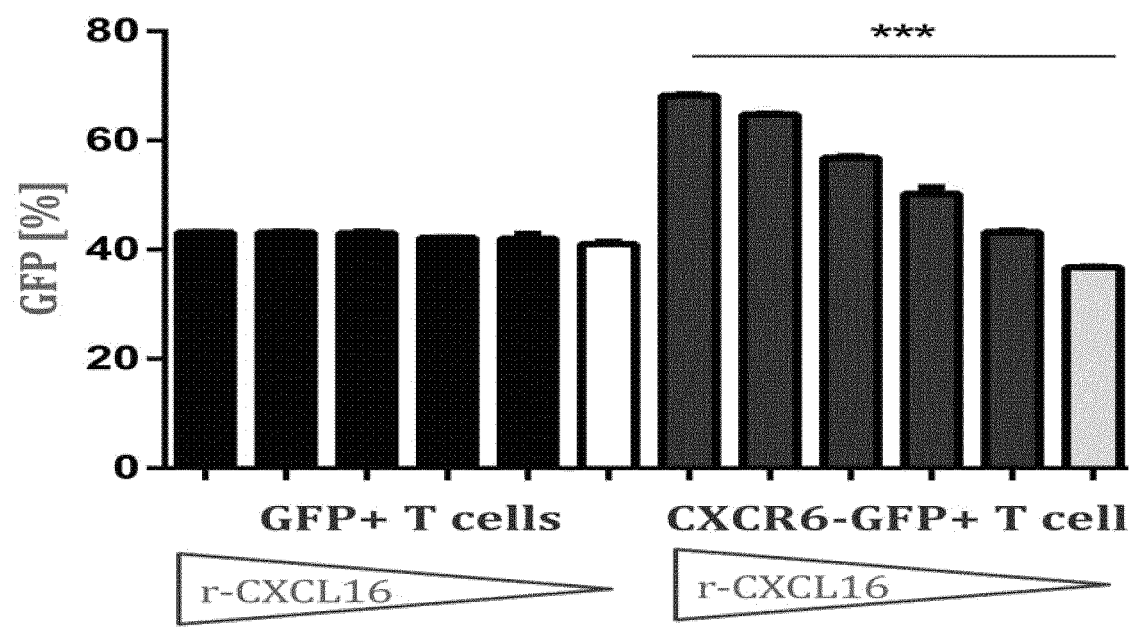

CXCR6 (SEQ ID NOs: 3 (cDNA); 4 (protein))-transduced CD8+ T cells and GFP-transduced CD8+ T cells were compared for their ability to migrate towards a CXCL16 gradient. Migration medium (0.5% BSA in RPMI medium) was used with or without recombinant CXCL16 (SEQ ID NO: 9; serial dilutions from 50 ng/ml to 3.125 ng/ml) (Peprotech, Hamburg) in the lower chamber and T cells in the upper chamber ($1 \times 10^6$ cells/well) of a 96-transwell plate. After 3 hours migrated T cells were resuspended with counting beads (Life Techonologies, Carlsbad, Calif., USA) for quantification. Migratory capacity was analyzed as cell number and GFP expression by flow cytometry (BD FACS Canto II). As shown in FIG. 4, CXCR6 (SEQ ID NOs: 3 (cDNA); 4 (protein))-transduced T cells specifically and dose dependently migrate towards CXCL16, which is not seen in T cells which were only transduced with GFP (SEQ ID NOs: 11 (nucleic acid); 12 (protein)). FIG. 4B shows that the migration is specific as enrichment of GFP is only seen in CXCR6 transduced T cells. P-values are depicted in the Figure,  indicates $p<0.01$ and * $p<0.001$.

Figure 5A:
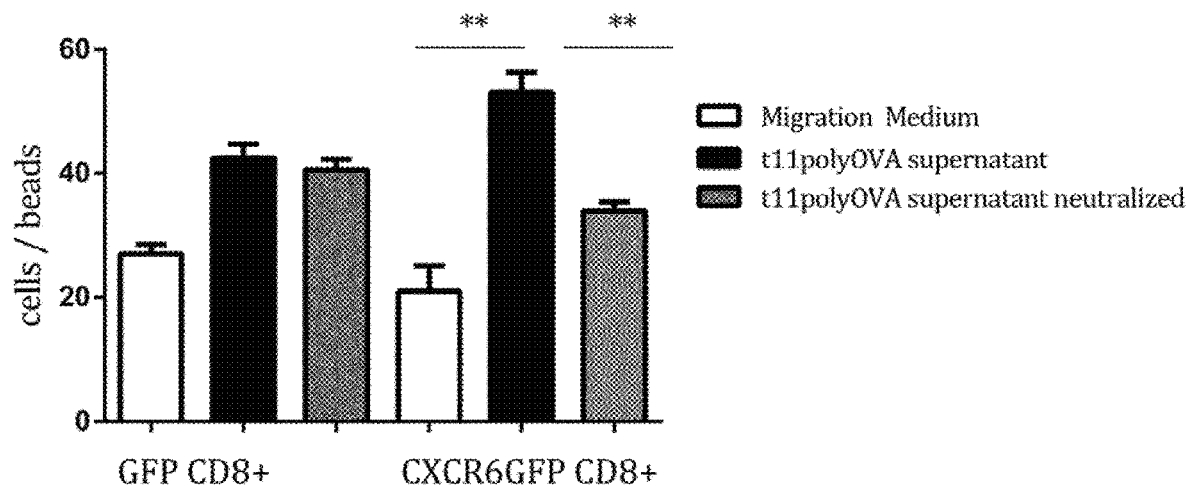
Figure 5B:
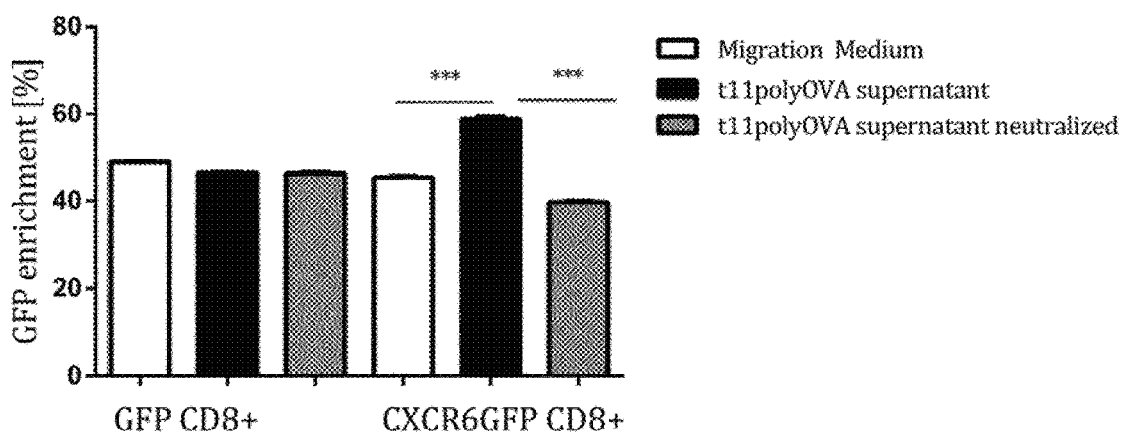

FIG. 5: Migration of CXCR6- and GFP-transduced T cells towards pancreatic cancer cell supernatant Tumor cells (i.e. T110299 cells) were seeded in a 6 well plate ($1 \times 10^6$ cells/well) and stimulated with recombinant IFN-γ and TNF-α (20 ng/ml) (Peprotech, Hamburg). After 48 hours, supernatants were incubated 30 min with or without anti-CXCL16 neutralizing antibody (2 μg/ml) (R&D Systems, Inc., MN, USA, polyclonal). CXCR6 (SEQ ID NOs: 3 (cDNA); 4 (protein))-transduced CD8+ T cells and CD8+ T cells which were only transduced with GFP (SEQ ID NOs: 11 (nucleic acid); 12 (protein)) were seeded at $1 \times 10^6$ cells/well. After 3 hours, migrated T cells were resuspended with counting beads (Life Techonologies, Carlsbad, Calif., USA) for quantification. Migration was quantified as cell number and GFP expression by flow cytometry. As shown in the FIG. 5A, CXCR6 (SEQ ID NOs: 3 (cDNA); 4 (protein))-transduced T cells migrate specifically towards supernatants of T110299 cells, which is not seen with GFP (SEQ ID NOs: 11 (nucleic acid/cDNA); 12 (protein))-transduced T cells. FIG. 5B shows that the migration is specific as enrichment of GFP is only seen in CXCR6 transduced T cells. P-values are depicted in the Figure,  indicates $p<0.01$ and * $p<0.001$.

Figure 6A:
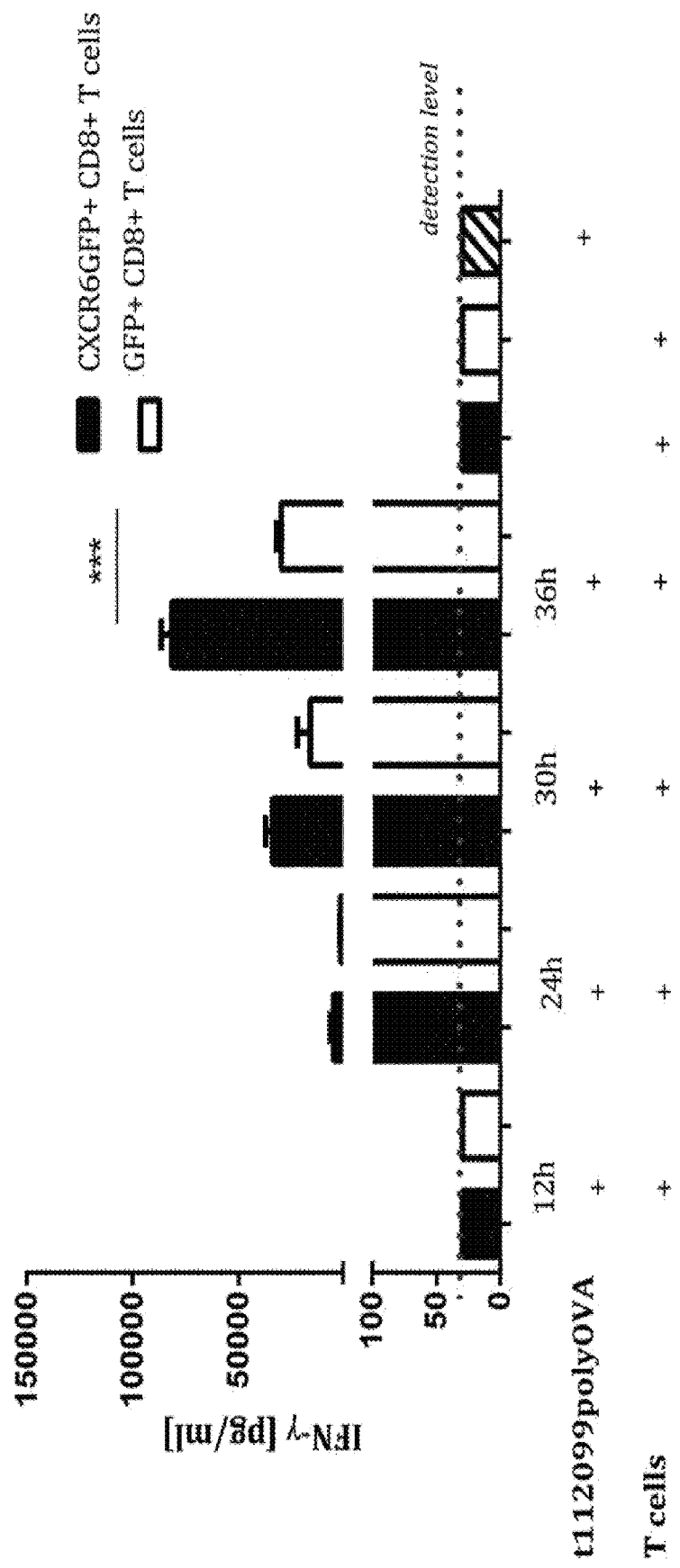
Figure 6B:
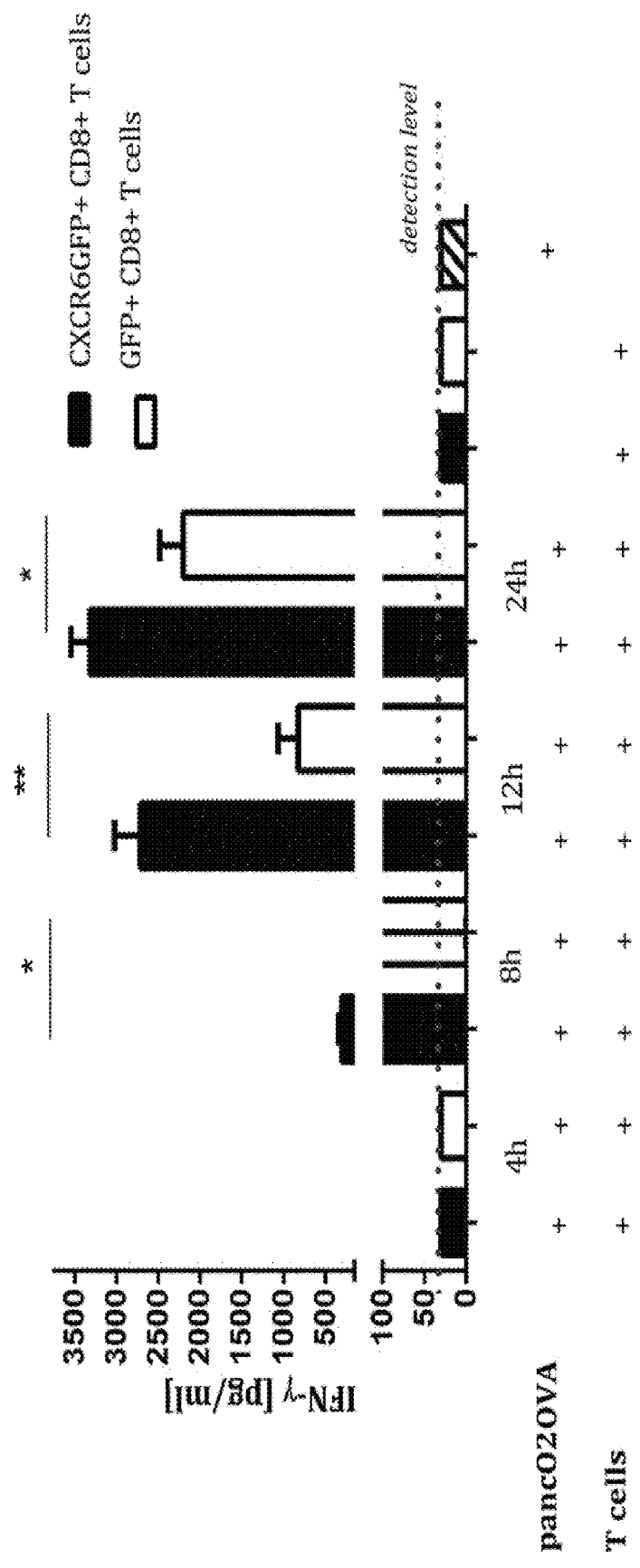

FIG. 6: Activation of CXCR6—in comparison to GFP-transduced T cells in co-culture with T110299 or Panc02-OVA tumor cells The pancreatic cancer cell lines Panc02-OVA and T110299 ($1 \times 10^4$/well) were co-cultured with T cells (1:1 to 1:10 ratios) in 96-well plates (flat bottom). Supernatants were harvested after 3, 8, 12, 24, 30 and 36 hours of co-culture. Activation level was measured as IFN-γ secretion by ELISA (Becton Dickinson, Franklin Lakes, N.J., USA). As shown in FIGS. 6A and 6B, CXCR6 (SEQ ID NOs: 3 (cDNA); 4 (protein))-transduced T cells show enhanced recognition of T110299 and Panc02-OVA in comparison to GFP (SEQ ID NOs: 11 (nucleic acid/cDNA); 12 (protein))-transduced T cells. P-values are depicted in FIGS. 6A and 6B, * indicates $p<0.05$,  $p<0.01$; * $p<0.001$.

Figure 7A:
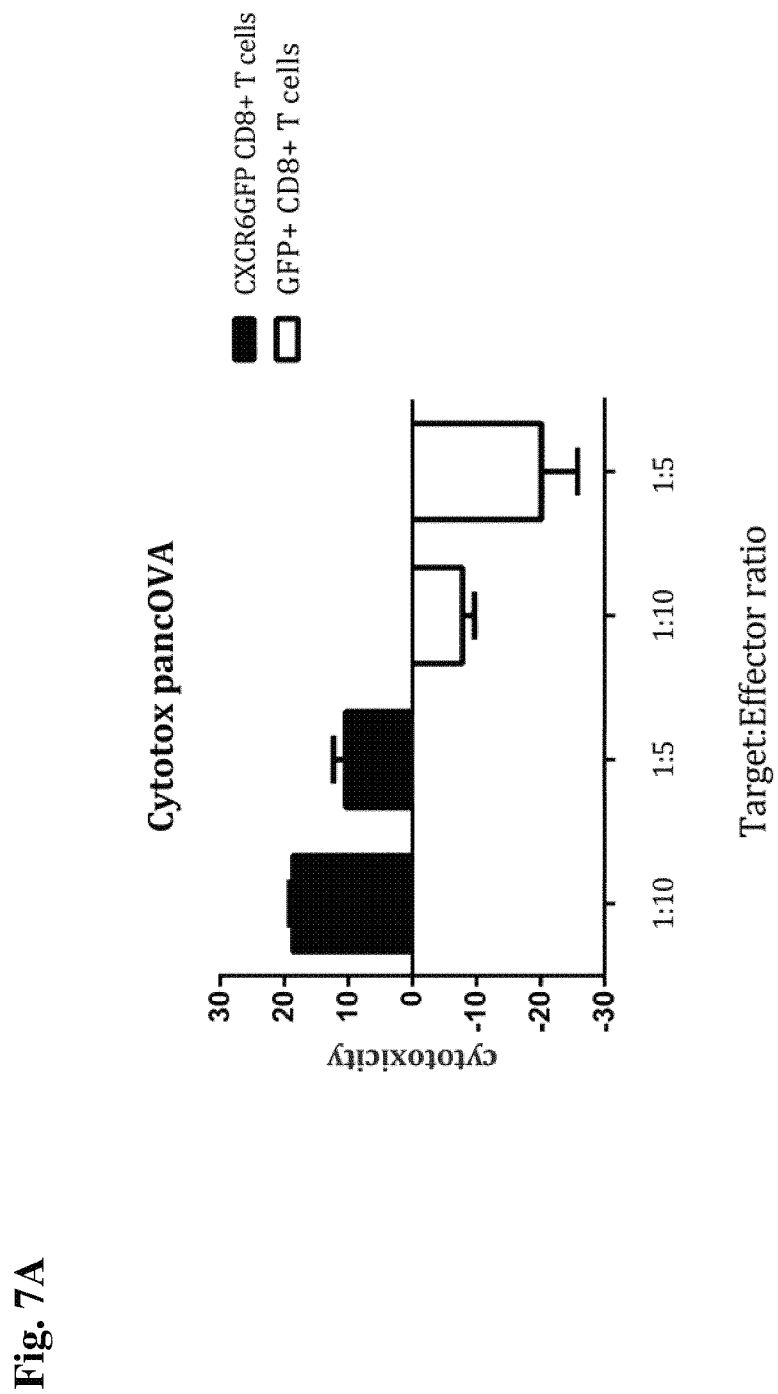
Figure 7B:
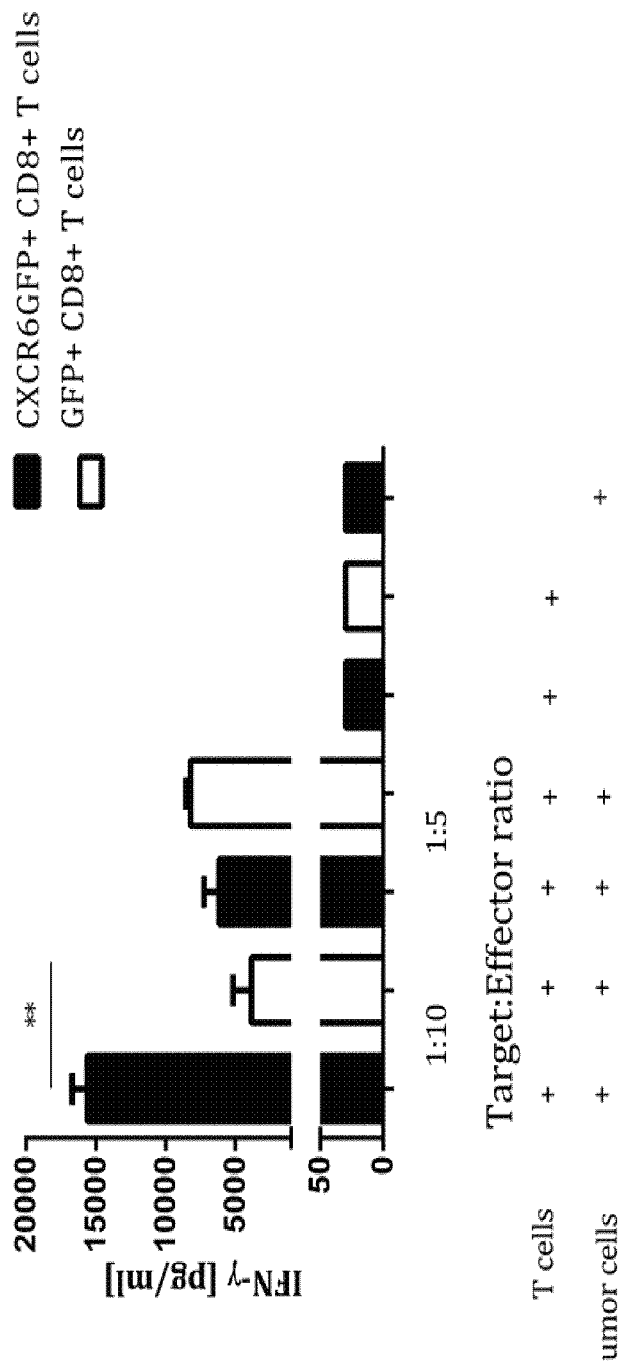
Figure 8A:
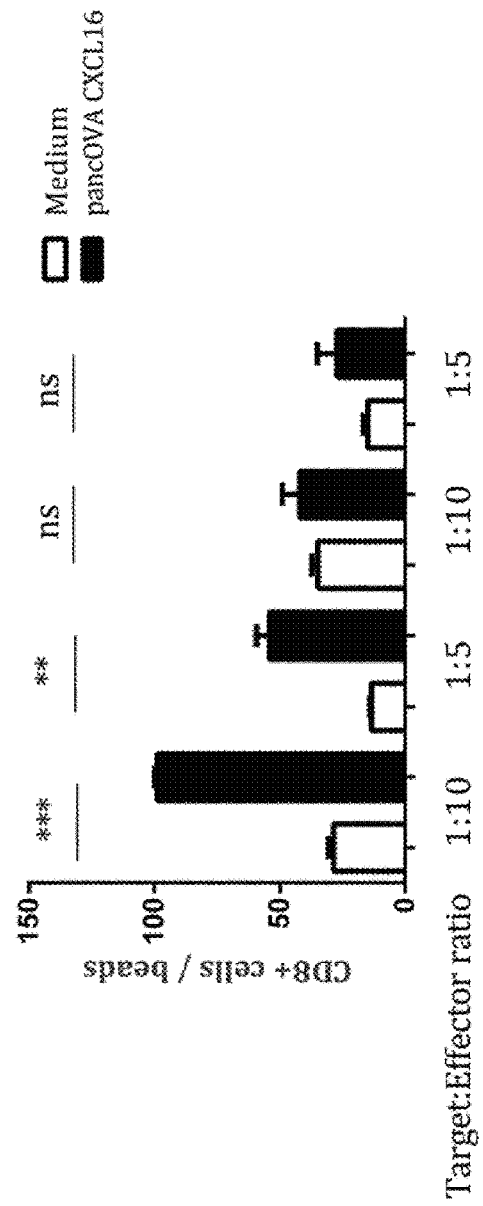
Figure 8B:
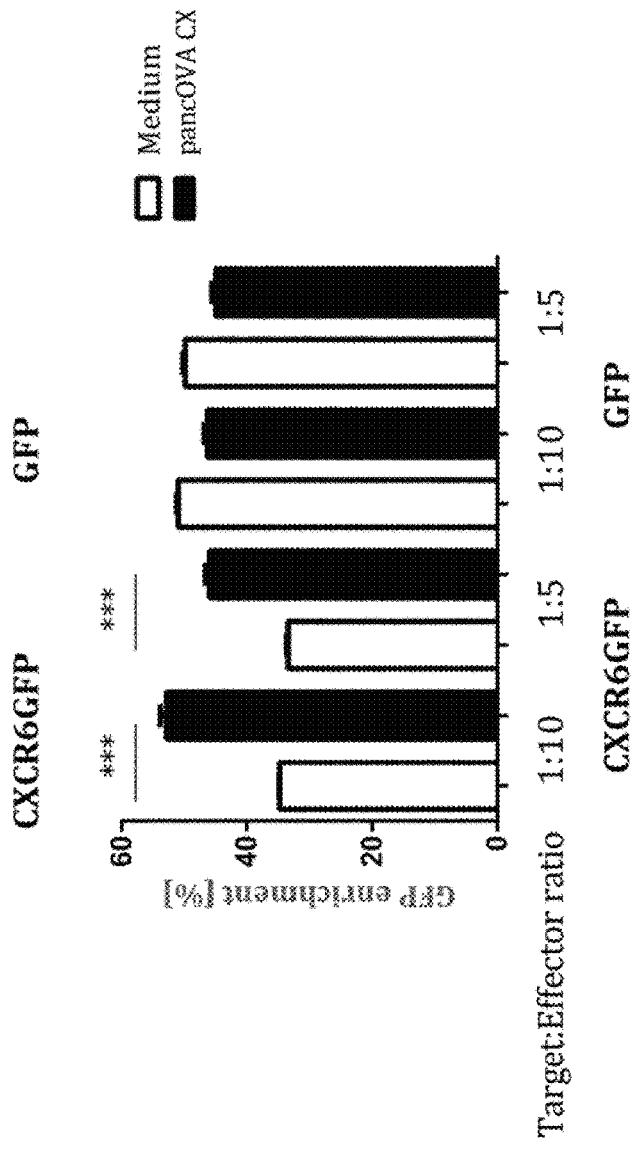
Figure 8C:
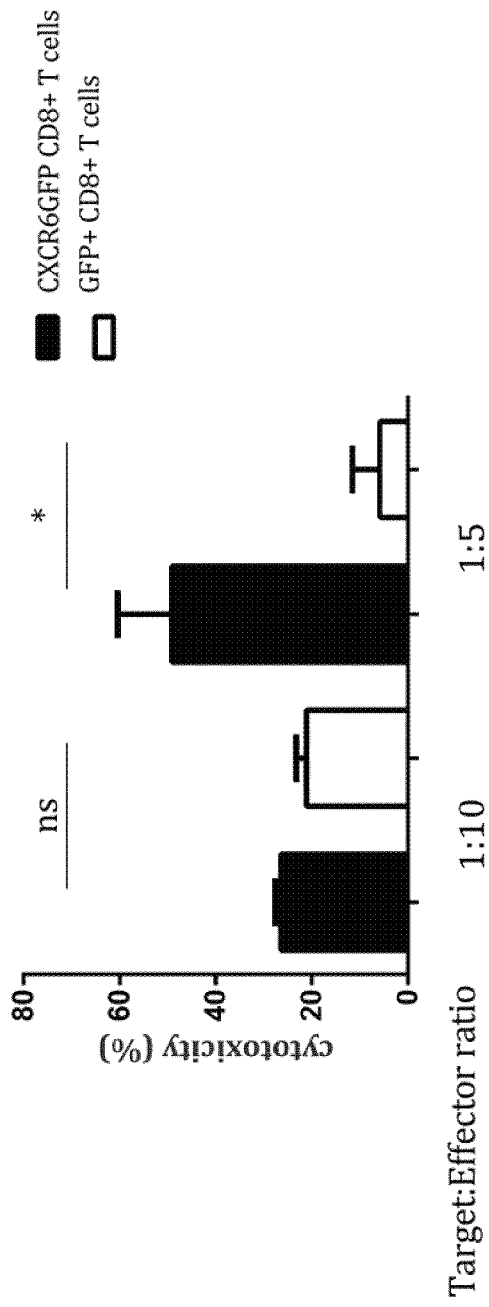
Figure 8D:
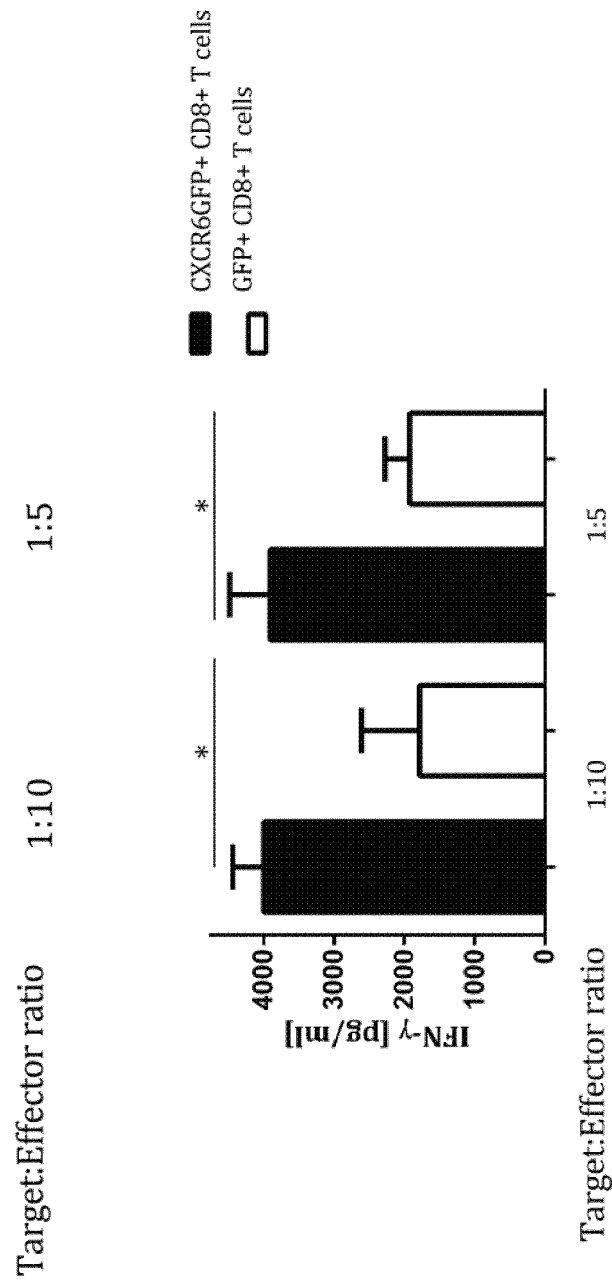

FIG. 7: Lysis of Panc02-OVA tumor cells by CXCR6-versus GFP-transduced OT-1-T cells The pancreatic cancer cell line Panc02-OVA ($3 \times 10^5$ cells/well) was co-cultured with CXCR6 (SEQ ID NOs: 3 (cDNA); 4 (protein))-transduced CD8+ T cells in 96-well plates (flat bottom). Supernatants were harvested after 5 hours of co-culture. Cytotoxicity was measured as LDH release (Promega Corporation, Madison, Wis., USA; see FIG. 7A), and activation level as IFN-γ secretion by ELISA (Becton Dickinson, Franklin Lakes, N.J., USA; see FIG. 7B). As shown in the Figure, CXCR6 (SEQ ID NOs: 3 (cDNA); 4 (protein))-transduced T cells have enhanced and T cell dose dependent lysis capacity of Panc02-OVA tumor cells in comparison to OT-1 T cells which were only transduced with GFP (SEQ ID NOs: 11 (nucleic acid/cDNA); 12 (protein)). The p-value is depicted in the Figure, ** indicates $p<0.01$.

FIG. 8: Migration of CXCR6-transduced OT-1 T cells towards Panc02-OVA-CXCL16 cells and subsequent lysis of these tumor cells in comparison to GFP-transduced OT-1 T cells The pancreatic cancer cell line Panc02-OVA was transduced with CXCL16 (SEQ ID NOs: 7 (cDNA) and 8 (protein); the Uniprot entry number of murine/mouse CXCL16 is Q8BSU2 (accession number with the enzry number version 102 and version 2 of the sequence)). A 96-transwell plate was coated with polylysin (100 μg/ml/well) (Sigma Aldrich, Steinheim). Tumor cells ($1 \times 10^5$/well) were seeded in the lower chamber and incubated for 12 hours. T cells ($8 \times 10^5$ cells/well) were administered in the upper chamber. After 2 hours, migration was stopped by removing the upper chamber. After additional 2 hours tumor cell killing was stopped by measuring LDH and IFN-γ secretion by ELISA. For quantification of migration, T cells were stained with an APC labeled anti-CD8 antibody (Biolegend, San Diego, Calif., USA, clone 53-6.7) and resuspended with counting beads (Life Techonologies, Carlsbad, Calif., USA). Migration was analyzed as cell number and GFP expression by flow cytometry. As shown in FIG. 8A, CXCR6-transduced OT-1 T cells specifically migrate towards CXCL16 producing tumor cells. FIG. 8B demonstrates that the migration towards the CXCL16 tumor cells is specific. Subsequently, the migrated T cells lysed these tumor cells (as shown in FIG. 8C). Tumor lysis correlated with T cell activation as measured by IFNγ release (see FIG. 8D). Migration, killing and activation is superior to the activity of GFP-transduced T cells. P-values are depicted in the Figure, * indicates p<0.05,  p<0.01; * p<0.001 and ns non-significant.

Figure 9:
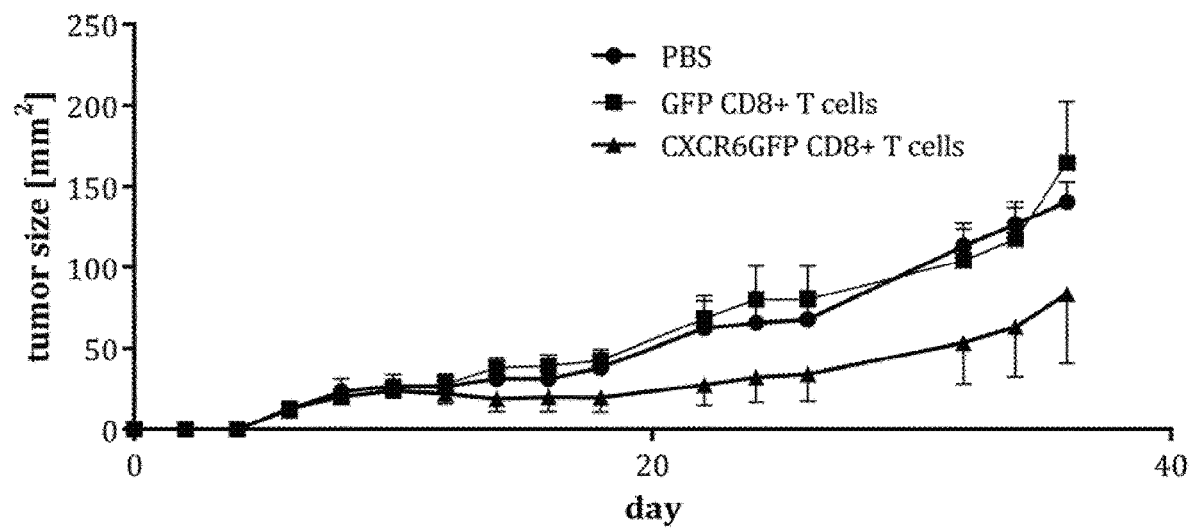

FIG. 9: Treatment of established Panc02-OVA tumors in mice with GFP- or CXCR6-transduced OT-1 T cells Female C57BL/6J Mice (5 per group) (Janvier, Frankreich, Cat. Number 2014-07-DE-RM-20) were injected with Panc02-OVA tumor cells ($2 \times 10^6$/mice) subcutaneously. After 7 days, T cells were adoptively transferred through the tail vein ($10 \times 10^6$ cells per mice). Therapeutic efficiency was measured as tumor growth every other day. As shown in the Figure, the treatment of established Panc02-OVA tumors with CXCR6-transduced OT-1 T cells leads to superior anti-tumoral activity compared to GFP-transduced OT-1 T cells.

Figure 10:
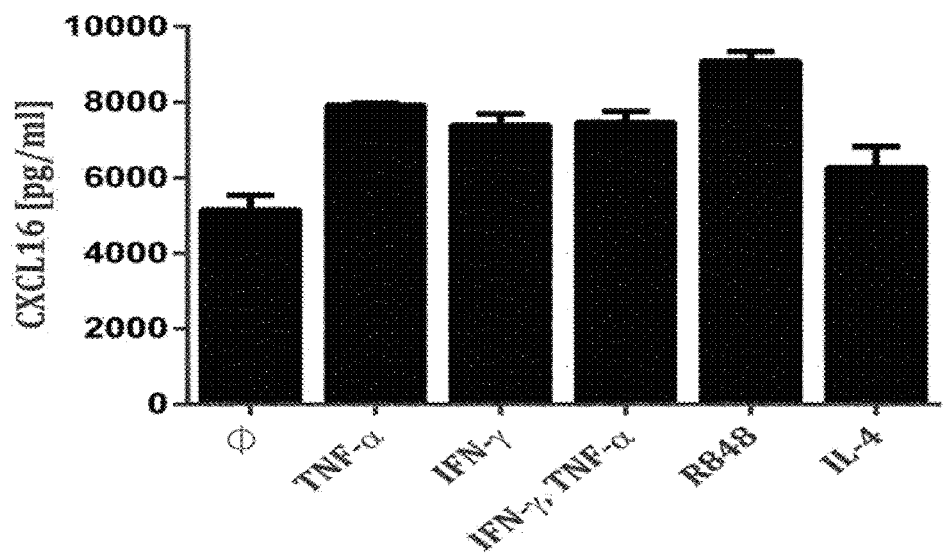

FIG. 10: CXCL16 production by BM-derived dendritic cells

Bone marrow was isolated from a C57BL/6J mouse (Janvier, Frankreich, Cat. Number 2014-07-DE-RM-20) Bone marrow cells were cultured with recombinant GM-CSF (20 ng/ml) (Peprotech, Hamburg) for seven days. Bone marrow derived dendritic cells (BM-DC, $10^4$ per well) were seeded in a 96-well plate (flat bottom) and stimulated with recombinant proteins (20 ng/ml) (TNF-α, IFN-γ or IL-4, Peprotech, Hamburg; or R848 Enzo Life Science, Lörrach). Supernatants were harvested after 48 hours. CXCL16 secretion was measured by ELISA (R&D Systems, Inc., MN, USA, polyclonal). As shown in the Figure, bone marrow-derived dendritic cells produce substantial amounts of CXCL16, which can be further enhanced by different stimuli.

FIG. 11: Clustering of CXCR6- and pMX-transduced T cells to dendritic cells

Figure 11A:
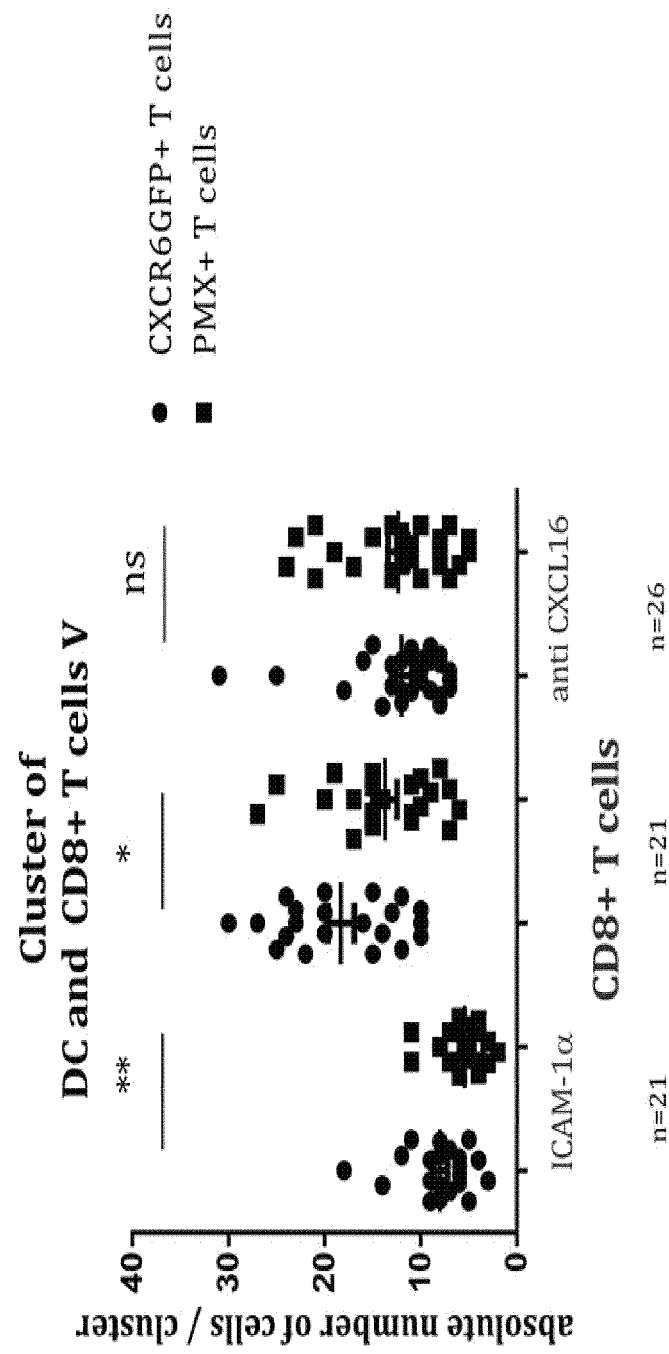
Figure 11B:
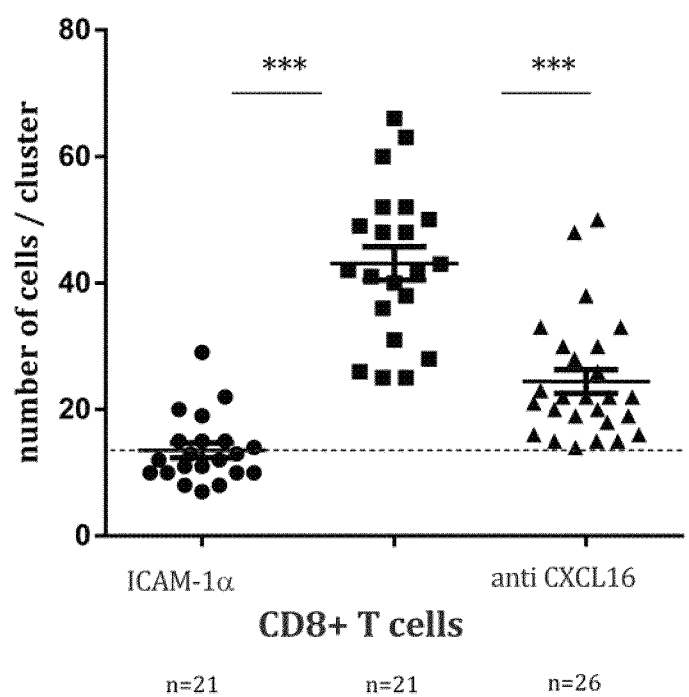

T cells were stained with two different PKH cell linker dyes (Sigma Aldrich, Steinheim). Staining efficiency was verified with flow cytometry. CXCR6 pos.T cells ($3 \times 10^4$ cells per well) were diluted in a 1:1 ratio with control-transduced T cells. T cell numbers were equilibrated by resuspension of 1:1 diluted samples of T cells with counting beads (Life Techonologies, Carlsbad, Calif., USA) and quantification of stained viable cells by flow cytometry. BM-DC were stimulated with $OVA_{257-264}$ peptide (SEQ ID NO: 10; 1 µg/ml) (Invivogen, San Diego, Calif., USA) and CpG (3 µg/ml) (Coley Pharmaceutical Group, Düsseldorf) in 96 well plates ($3 \times 10^3$ per well) and co-cultured with T cells at a 1:10 ratio for 3 hours partly in the presence or absence of anti-ICAM1α antibody (0.5 mg/ml) (BioXCell, NH, USA, clone YNI.7.4) or anti-CXCL16 neutralizing antibody (10 µg/ml) (R&D Systems, Inc., MN, USA, polyclonal) for 3 hours. Cells were gently transferred to a glass-bottomed dish and used for confocal microscopy. Clusters were analyzed for the proportion of CXCR6GFP pos. T cells to control-transduced T cells. As shown in FIGS. 11A and 11B, CXCR6 (SEQ ID NOs: 3 (cDNA); 4 (protein))-transduced T cells show enhanced clustering ability to dendritic cells compared to pMX-transduced T cells. The pMX-vector is an empty retroviral vector, which does not hold any insert. This vector can be found at the Addgene homepage (see https://www.addgene.org/vector-database/3674/). The pMX-transduced T cells are published in Kitamura (2003) Tokyo Exp Hematol. 31(11):1007-14. Enhanced clustering capacity is CXCL16 but not ICAM-1 dependent. P-values are depicted in the Figure, * indicates p<0.05,  p<0.01; * p<0.001 and ns non-significant.

Figure 12:
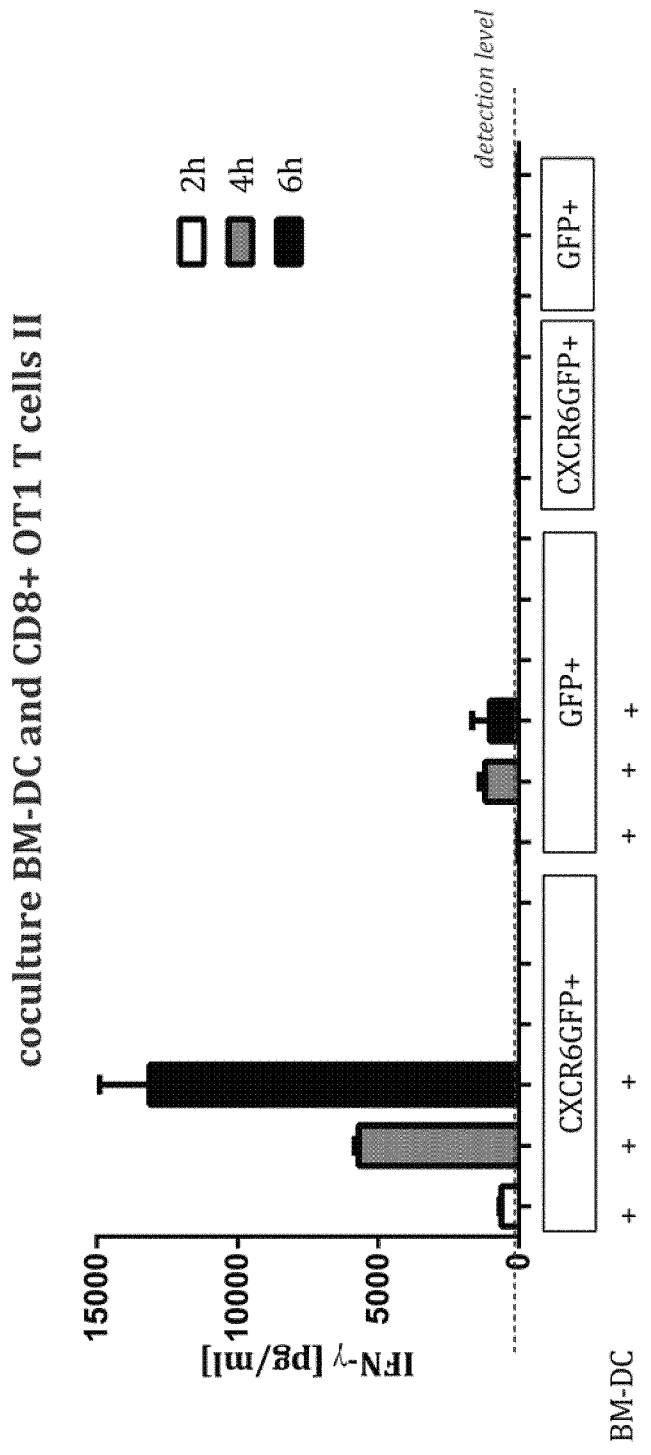

FIG. 12: Activation of CXCR6- and GFP-transduced OT-1 T cells in the presence of dendritic cells Co-culture of BM-DC cells ($5 \times 10^3$ per well) with CXCR6GFP-transduced T cells or with GFP-transduced T cells (1:1 to 1:10 ratios) were performed in 96 well plates (flat bottom) in the presence of $OVA_{257-264}$ peptide (1 µg/ml) (Invivogen, San Diego, Calif., USA). Supernatants were harvested after 2, 4 and 6 hours. IFN-γ secretion was measured by ELISA (Becton Dickinson, Franklin Lakes, N.J., USA). As shown in the Figure, CXCR6 (SEQ ID NOs: 3 (cDNA); 4 (protein))-transduced T cells display enhanced activation capacity by dendritic cells compared to GFP (SEQ ID NOs: 11 (cDNA); 12 (protein))-transduced T cells.

Figure 13:
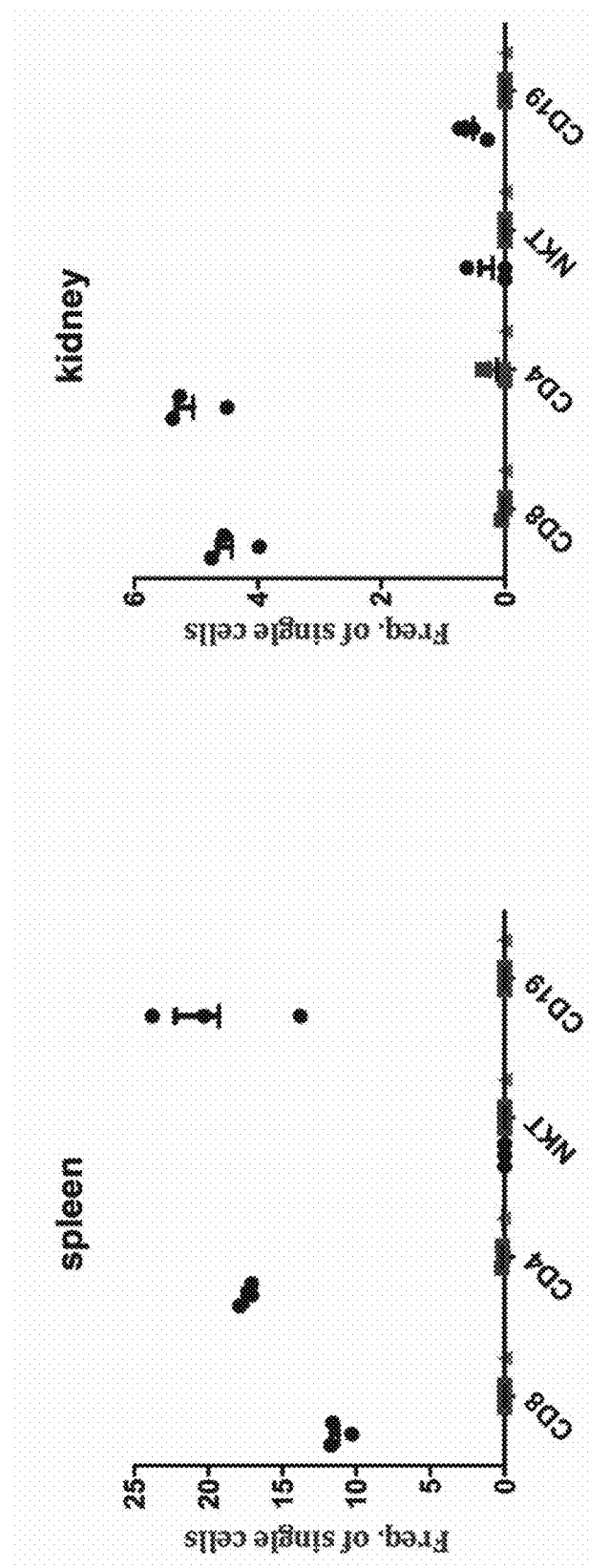
Figure 13:
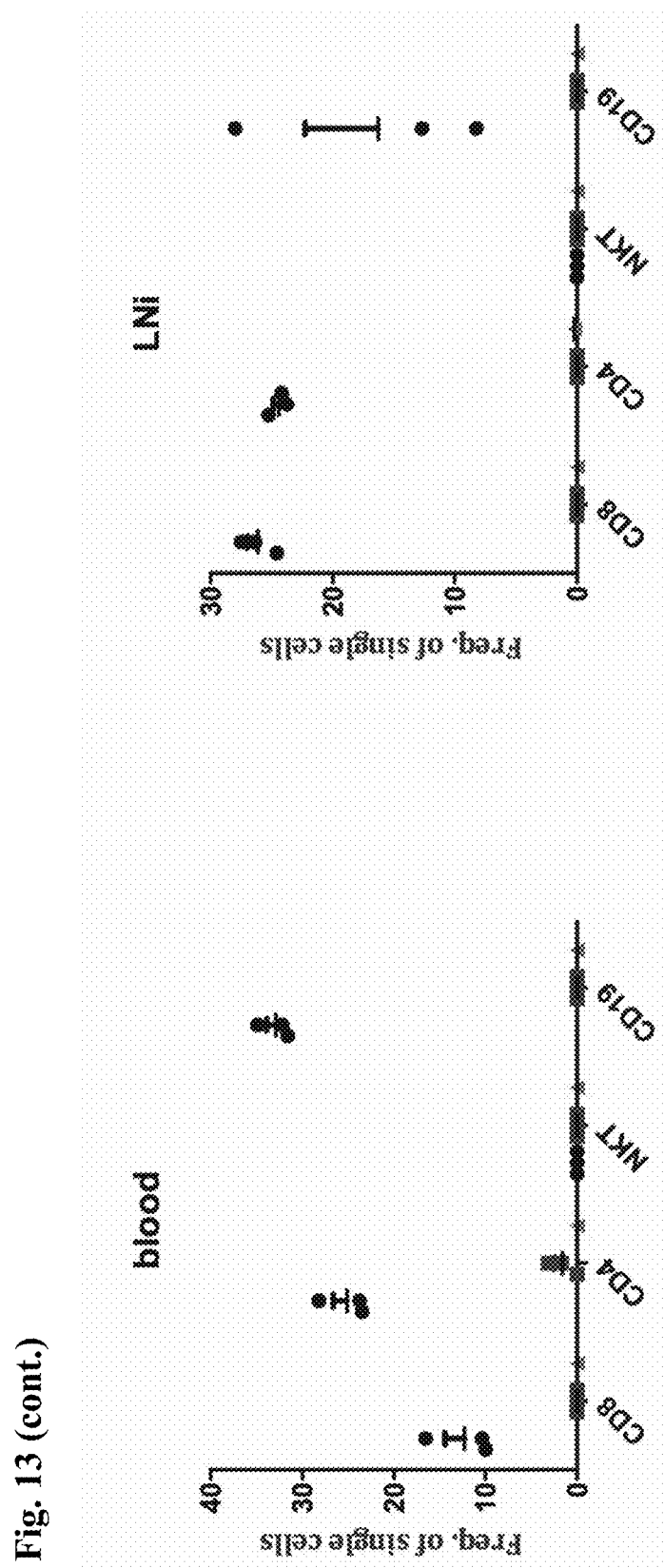
Figure 13:
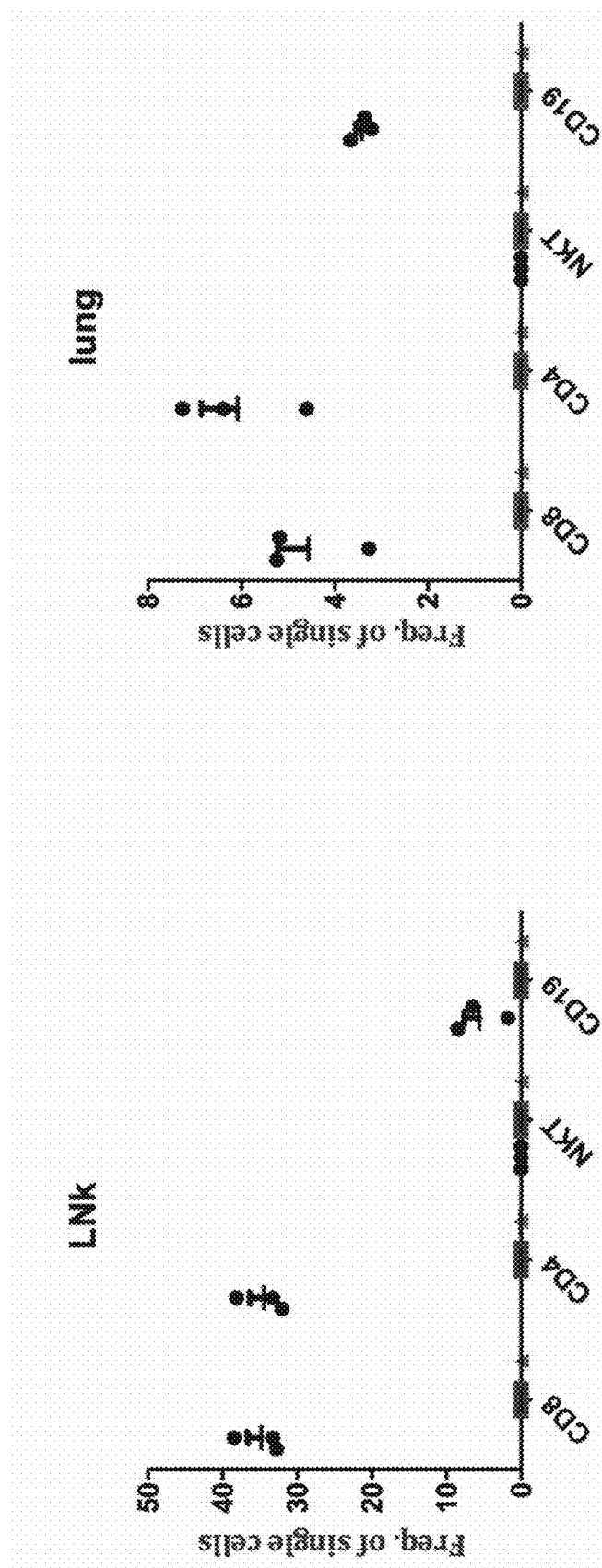
Figure 13:
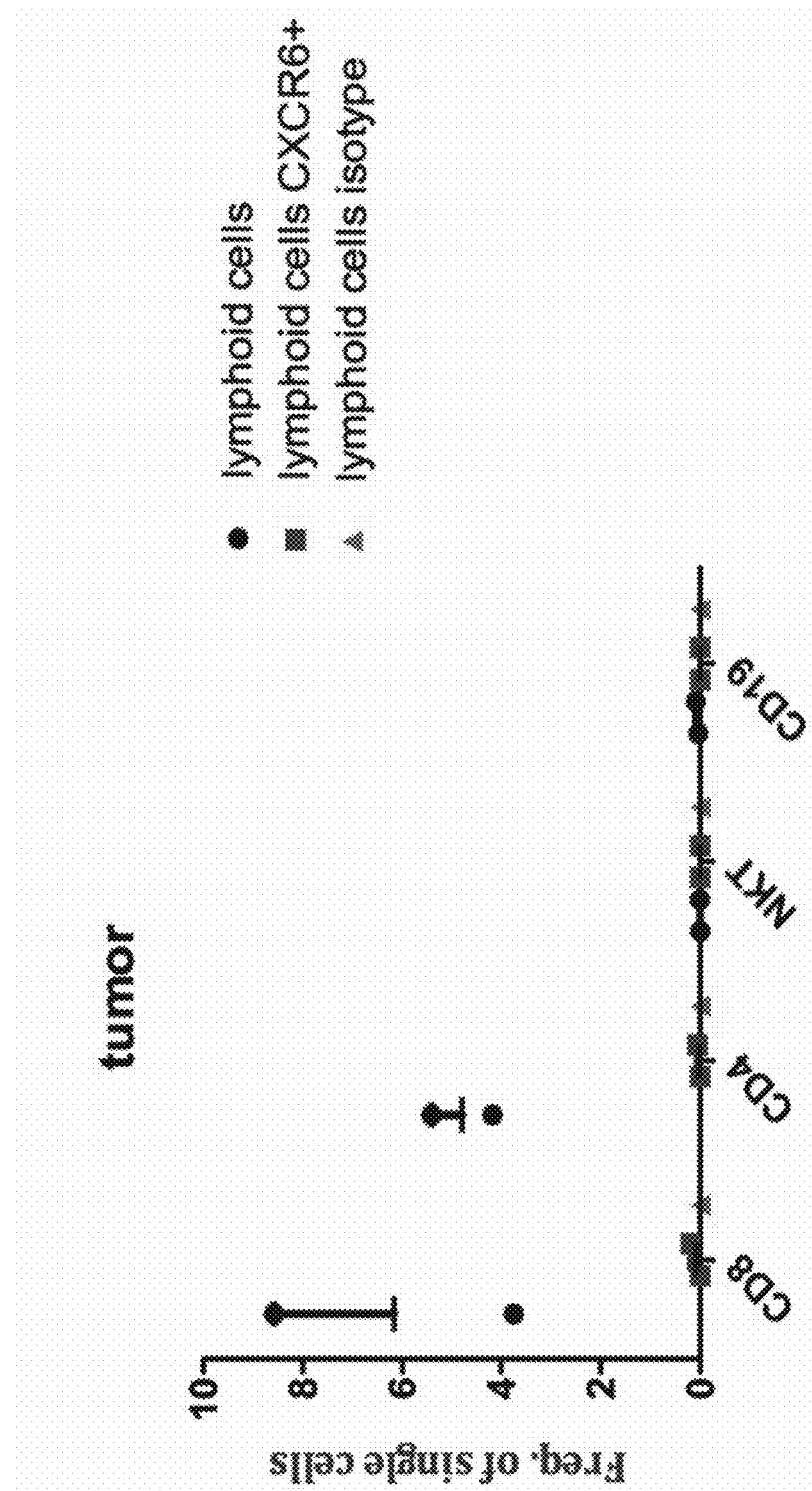

FIG. 13: Expression of CXCR6 in Panc02-OVA tumor bearing mice

Expression of CXCR6 in tumor bearing mice was analyzed in different organs, i.e. spleen, tumor-contralateral lymph node (LNk), tumor, kidney, tumor-ipsilateral lymph node (LNi) and lung and blood to peripheral blood cells. Female C57BL/6J mice (3 per group) (Janvier, France (Cat. Number 2014-07-DE-RM-20)) were injected subcutaneously with Panc02-OVA tumor cells (Jacobs et al. Int J Cancer 128 (2011) at a concentration of $2 \times 10^6$ per mice. Organs and tumors were isolated and processed on day 20 of induction. The tested spleen, tumor-contralateral lymph node (LNk), tumor, kidney, tumor-ipsilateral lymph node (LNi) and lung organs refer to single cell suspensions as obtained from wild type C57BL/6J mice of the corresponding organ or blood to peripheral blood cells from the C57BL/6J mice. For flow cytometric analysis, cells were stained with the following antibodies: (1.) Lymphoid panel: FITC-conjugated anti-mouse CD3e (clone 17A2, BioLegend, San Diego, Calif., USA), PE-conjugated anti-mouse CD4 (clone GK1.5, BioLegend, San Diego, Calif., USA), Pacific Blue-conjugated CD8a (clone 53-6.7, BioLegend, San Diego, Calif., USA), PerCp-Cy5.5-conjugated CD19 (clone 6D5, BioLegend, San Diego, Calif., USA) and PE-Cy7-conjugated NKp46 (clone 29A1.4, BioLegend, San Diego, Calif., USA). (2.) Myeloid panel: PE-Cy7-conjugated NKp46, APC-Cy7-conjugated CD11b (clone Ml/70, BioLegend, San Diego, Calif., USA), PE-conjugated CD11c (clone N418, BioLegend, San Diego, Calif., USA), FITC-conjugated Gr1 (clone RB6-8C5, BioLegend, San Diego, Calif., USA), PerCp-Cy5.5-conjugated Ly-6C (clone HK1.4, BioLegend, San Diego, Calif., USA) and Pacific Blue-conjugated F4/80 (clone BM8, BioLegend, San Diego, Calif., USA). The expression level of CXCR6 was analyzed by using a APC-conjugated anti-mouse CXCR6 antibody (FAB2145A, R&D Systems, Inc., MN, USA) and the corresponding isotype (rat IgG2B, RTK4530, BioLegend, San Diego, Calif., USA). All flow cytometric data were acquired on a BD FACS CantoII and analyzed using the FlowJo software. As shown in FIG. 13, CXCR6 cannot be detected in significant levels on the surface of the analyzed immune cells (CD8 T cells, CD4 Tcells, NK T cells and CD19 B cells) by flow cytometry.

Figure 14A:
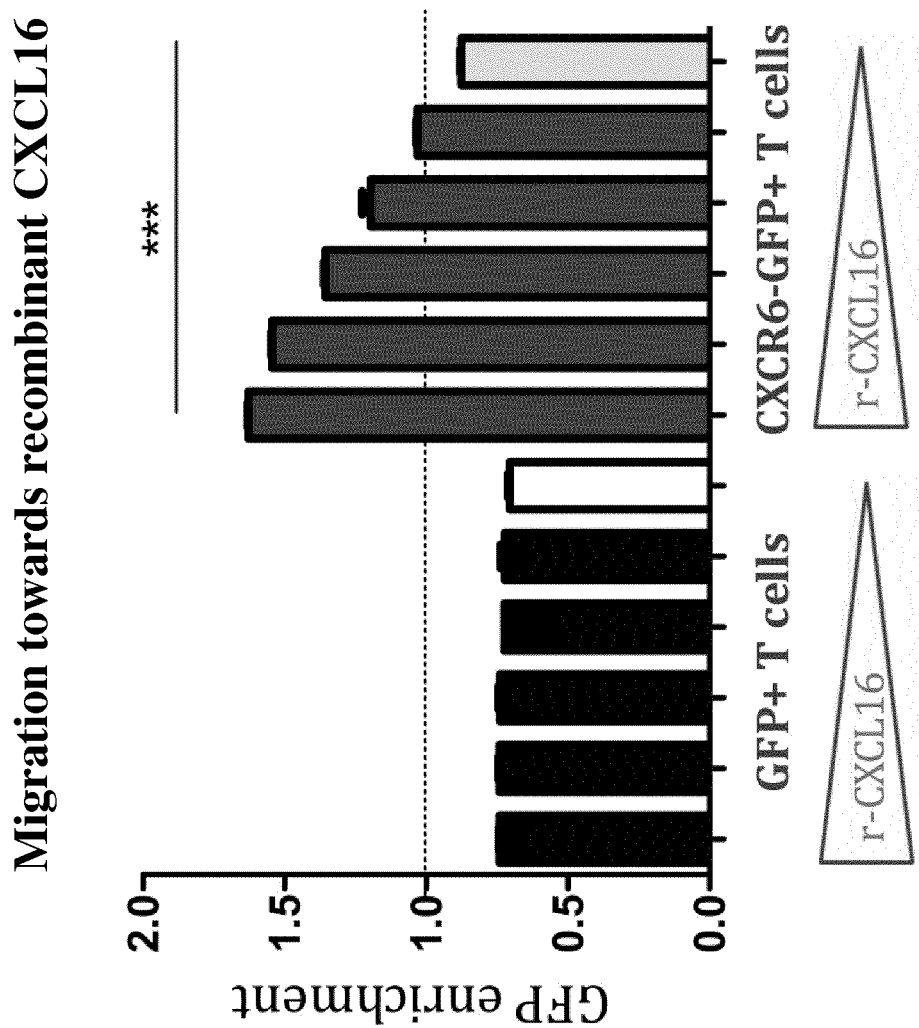

FIG. 14: Migration of CXCR6- and GFP-transduced T cells towards pancreatic cancer cell supernatant (A): CXCR6 (SEQ ID NOs: 3 (cDNA); 4 (protein))-transduced CD8+ T cells and GFP-transduced CD8+ T cells were compared for their ability to migrate towards a CXCL16 gradient. Migration medium (0.5% BSA in RPMI medium) was used with or without recombinant CXCL16 (SEQ ID NO: 9; serial dilutions from 50 ng/ml to 3.125 ng/ml) (Peprotech, Hamburg) in the lower chamber and T cells in the upper chamber ($1 \times 10^6$ cells/well) of a 96-transwell plate. After 3 hours migrated T cells were resuspended with counting beads (Life Techonologies, Carlsbad, Calif., USA) for quantification. Migratory capacity was analyzed as cell number and GFP expression by flow cytometry (BD FACS Canto II). As shown in FIG. 4, CXCR6 (SEQ ID NOs: 3 (cDNA); 4 (protein))-transduced T cells specifically and dose dependently migrate towards CXCL16, which is not seen in T cells which were only transduced with GFP (SEQ ID NOs: 11 (nucleic acid); 12 (protein)).

Figure 14B:
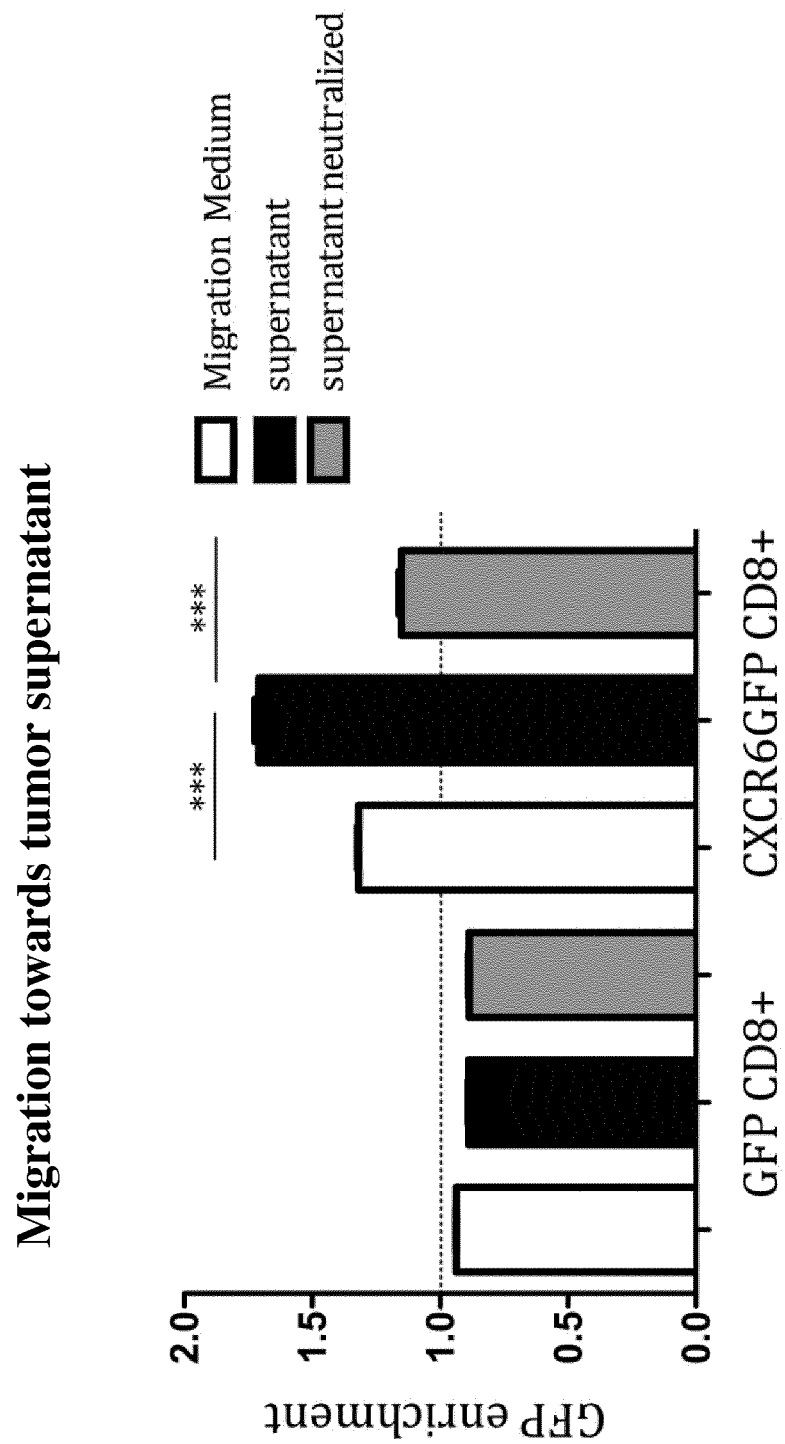

(B): Tumor cells (i.e. Panc02-OVA or T110299 cells) were seeded in a 6 well plate ($1 \times 10^6$ cells/well) and stimulated with recombinant IFN-γ and TNF-α (20 ng/ml) (Peprotech, Hamburg). After 48 hours, supernatants were incubated 30 min with or without an anti-CXCL16 neutralizing antibody (2 µg/ml) (R&D Systems, Inc., MN, USA, polyclonal). CXCR6 (SEQ ID NOs: 3 (cDNA); 4 (protein))-transduced CD8+ T cells and GFP (SEQ ID NOs: 11 (cDNA); 12 (protein))-transduced CD8+ T cells were seeded at a concentration of $1 \times 10^6$ cells/well. After 3 hours, migrated T cells were resuspended with counting beads (Life Techonologies, Carlsbad, Calif., USA) for quantification. Migration was quantified as cell number and GFP expression by flow cytometry. As shown in FIG. 14B, CXCR6 (SEQ ID NOs: 3 (cDNA); 4 (protein))-transduced T cells migrate specifically towards supernatants of T110299 cells, which is not seen with GFP (SEQ ID NOs: 11 (cDNA); 12 (protein))-transduced T cells. P-values are depicted in the Figure, *** p<0.001.

Figure 15:
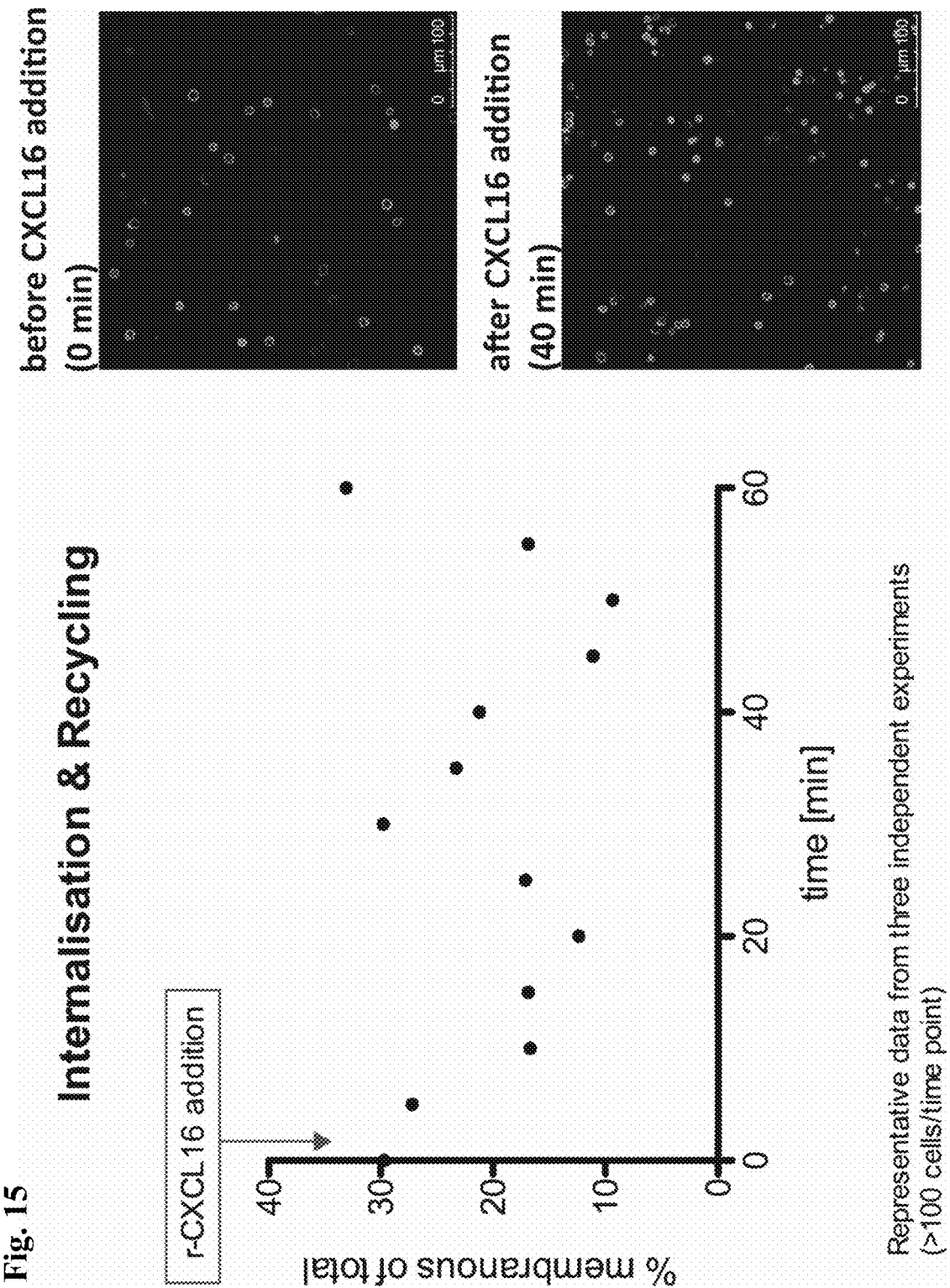

FIG. 15: Internalisation and recycling of CXCR6 due to CXCL16 binding

CXCR6 (SEQ ID NOs: 3 (cDNA); 4 (protein))-transduced CD8+ T cells ($5 \times 10^5$ cells) were treated with 200 ng recombinant CXCL16 (Peprotech, Hamburg) and analyzed by live fluorescence microscopy at time intervals of 5 minutes over a period of 1 hour. Confocal imaging was performed with a Leica SP2 AOBS confocal microscope. As shown in FIG. 15, CXCL16 stimulation resulted in a CXCR6 internalisation and re-expression within a time span of 30 minutes.

Figure 16:
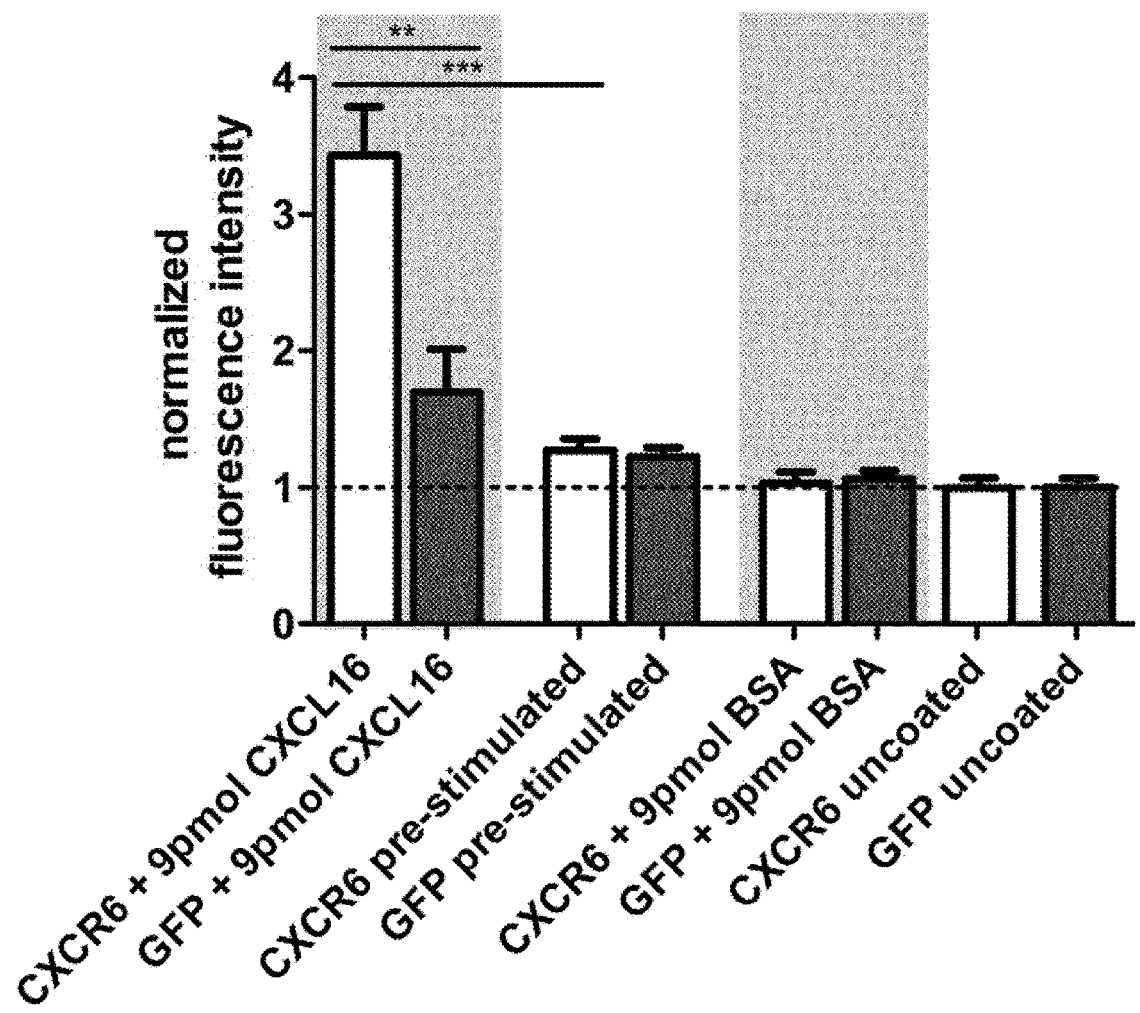

FIG. 16: Adhesion of CXCR6-transduced T cells to recombinant CXCL16

CXCR6 (SEQ ID NOs: 3 (cDNA); 4 (protein))-transduced CD8+ T cells and GFP (SEQ ID NOs: 11 (cDNA); 12 (protein))-transduced CD8+ T cells were compared for their ability to adhere to immobilised recombinant CXCL16. First, T cells were stained with Calcein (Life Technologies, Carlsbad, Calif., USA) and pre-incubated with or without 2 µg/ml anti-mouse CXCL16 neutralizing antibody (R&D Systems, Inc., MN, USA, polyclonal). Nickel-coated 96-well plates (Cat. Number 15442, ThermoScientific, Darmstadt) were pre-incubated with 9 pmol His-tagged CXCL16 (Cat. Number 50142-M08H, SinoBiological, Peking, China) or 9 pmol BSA. The pre-stimulated T cells were transferred to the CXCL16 or BSA coated Nickel plate. After 25-minute incubation and a washing step, attached cells were lysed using RIPA buffer. Calcein was detected with the Mithras LB 940 Multimode Microplate Reader (Berthold Technologies, Bad Wildbad), where the fluorescent signal intensity is proportional to the quantity of adherent cells. As shown in FIG. 16, CXCR6 (SEQ ID NOs: 3 (cDNA); 4 (protein))-transduced T cells attach specifically to CXCL16. P-values are depicted in the Figure,  p<0.01; * p<0.001.

Figure 17A:
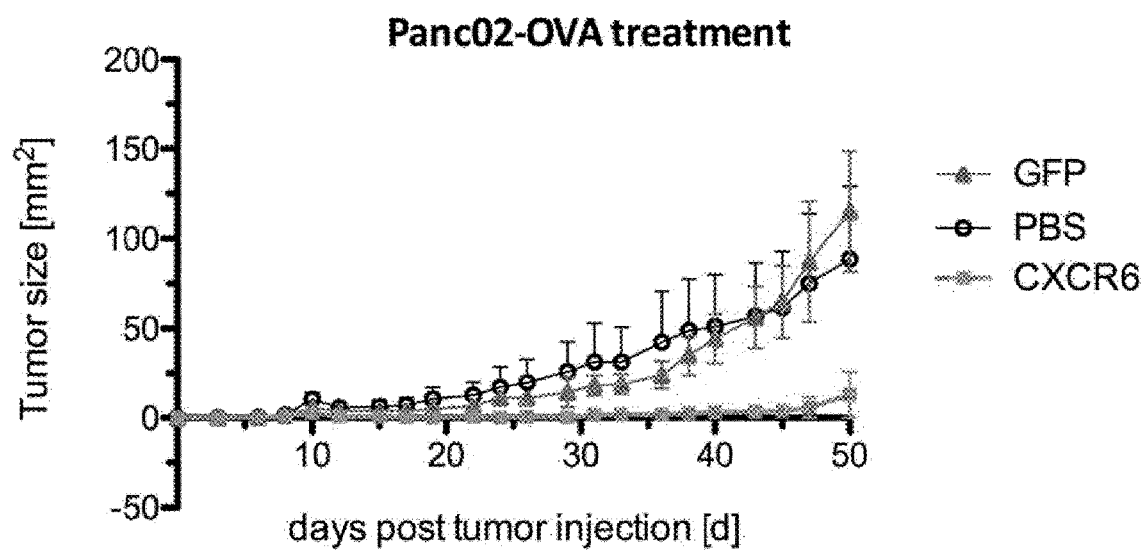
Figure 17B:
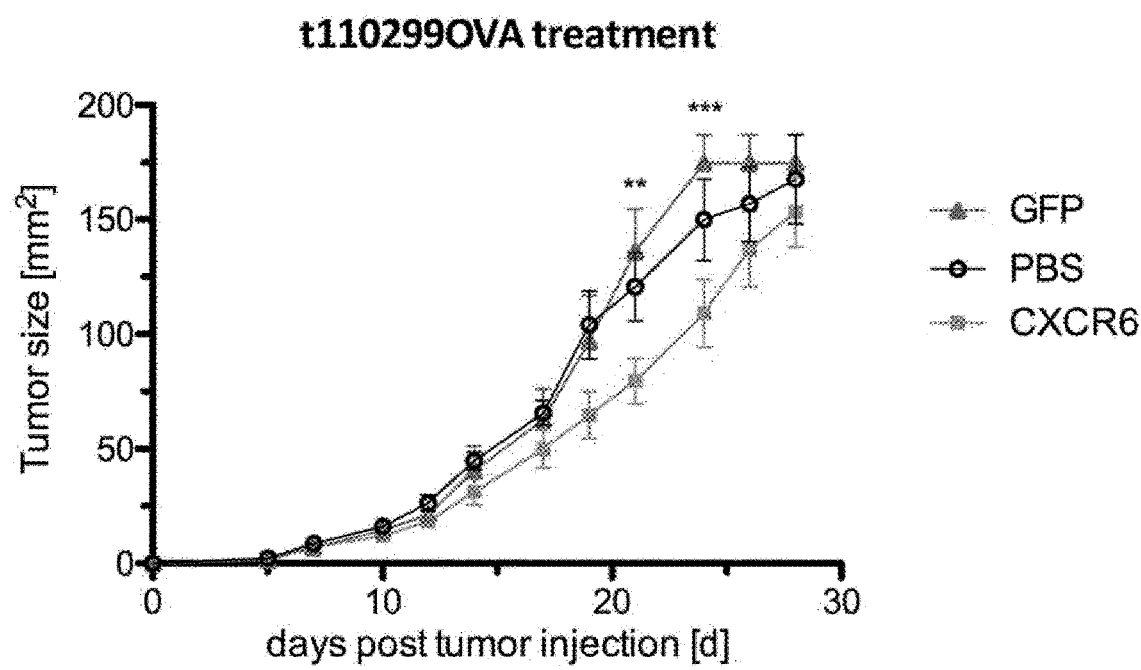

FIG. 17: Treatment of established Panc02-OVA tumors in mice with GFP- or CXCR6-transduced OT-1 T cells Female C57BL/6J Mice (5 per group) (Janvier, Frankreich (Cat. Number 2014-07-DE-RM-20)) were injected with Panc02-OVA tumor cells ($2 \times 10^6$/mice) or T110299-OVA tumor cells ($4 \times 10^6$/mice) subcutaneously. After 5 days, T cells were adoptively transferred through the tail vein ($10 \times 10^6$ cells per mice). Therapeutic efficiency was measured as tumor growth every other day. As shown in FIGS. 17A and 17B, the treatment of established Panc02-OVA tumors or T110299-OVA tumor cells with CXCR6 (SEQ ID NOs: 3 (cDNA); 4 (protein))-transduced OT-1 T cells leads to superior anti-tumoral activity compared to GFP (SEQ ID NOs: 11 (cDNA); 12 (protein))-transduced OT-1 T cells. P-values are depicted in the Figure, *** p<0.001.

Figure 18:
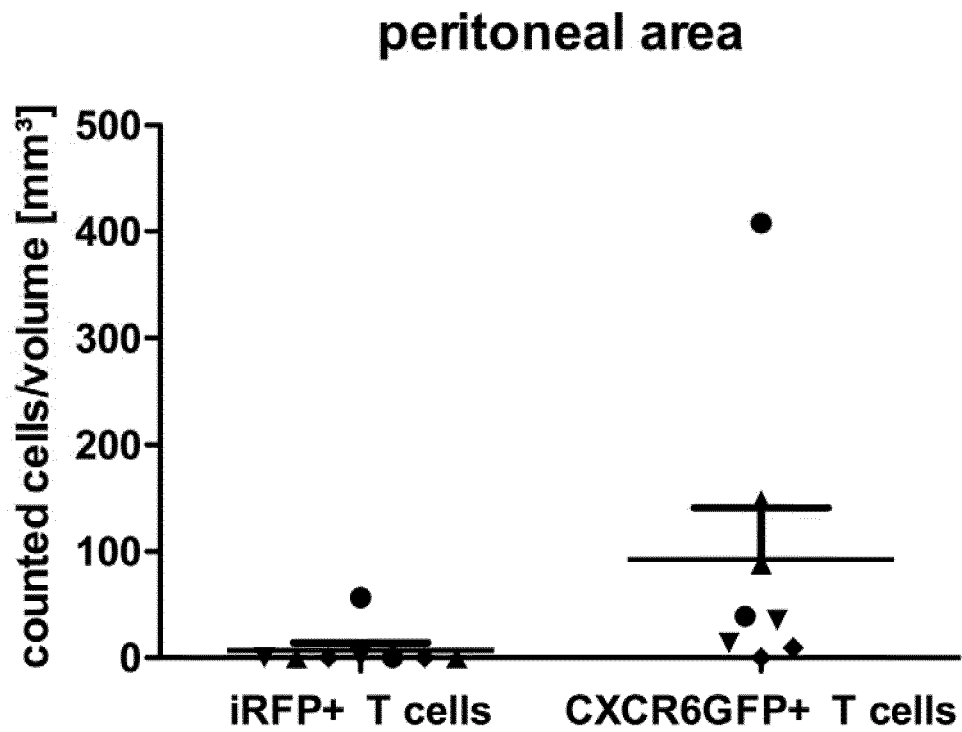
Figure 18:
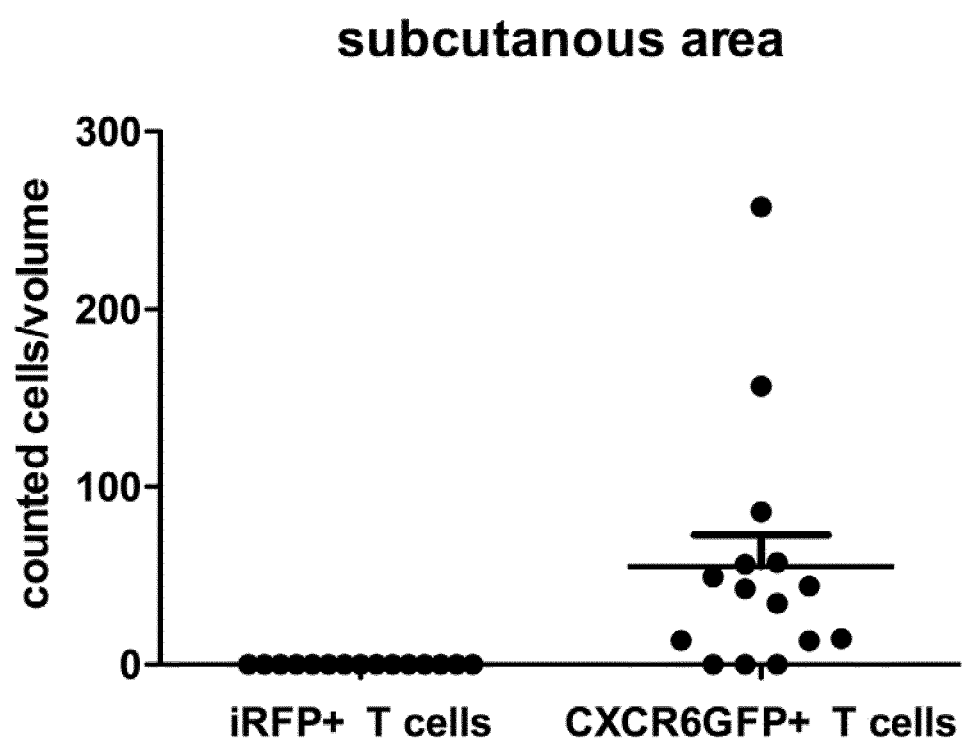
Figure 20:
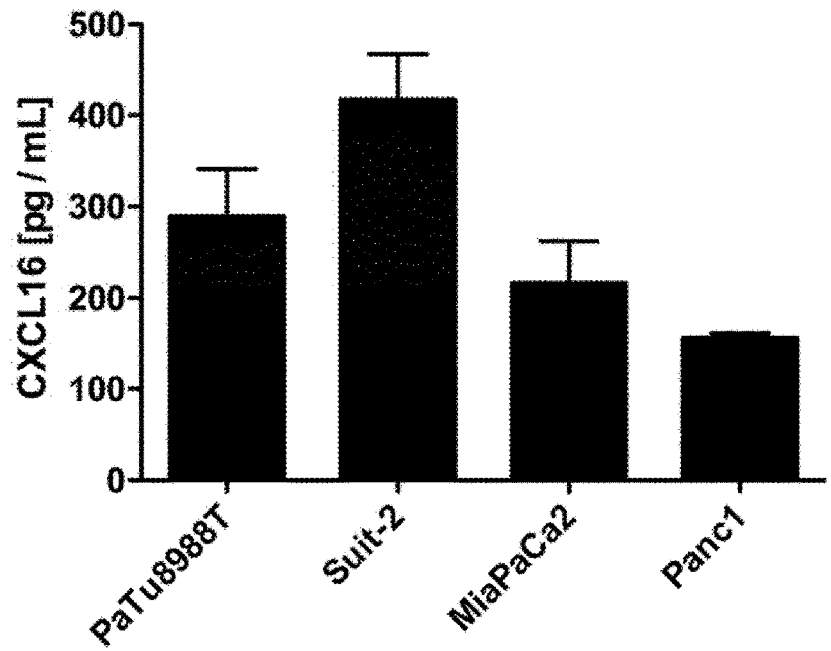

FIG. 18: Quantification of tumor-infiltrating iRFP (Red Fluorescent Protein)—or CXCR6-transduced OT-1 T cells Female C57BL/6J Mice (Janvier, Frankreich (Cat. Number 2014-07-DE-RM-20)) were injected with Panc02-OVA tumor cells ($2 \times 10^6$/mice) subcutaneously. After 5 days, T cells were adoptively transferred through the tail vein ($10 \times 10^6$ cells per mice). Organs and tumors were isolated and processed on day 10 of induction (five days after T cell transfer). 15 minutes before organ removal, eFluor® 450-conjugated anti-mouse CD31 (4 µg/mice, clone 390, eBioscience, Frankfurt) was injected intravenously through the tail vein. For flow cytometric analysis, cells were stained with Pacific Blue-conjugated anti-mouse CD8a (clone 53-6.7, BioLegend, San Diego, Calif., USA) and analyzed with counting beads (Life Techonologies, Carlsbad, Calif., USA) for quantification. For 2 Photon microscopy, tumors were embedded in 1.5% agarose and 2 Photon imaging was performed with the Leica "SP5II MP" system equipped with a "Spectra Physics MaiTai DeepSee" Ti:Sa pulsed laser. As shown in FIG. 20, CXCR6 (SEQ ID NOs: 3 (cDNA); 4 (protein transduced T cells are not only specifically enriched in tumor tissue, but also have the ability to migrate towards tumor areas with few blood vessels.

Figure 19:
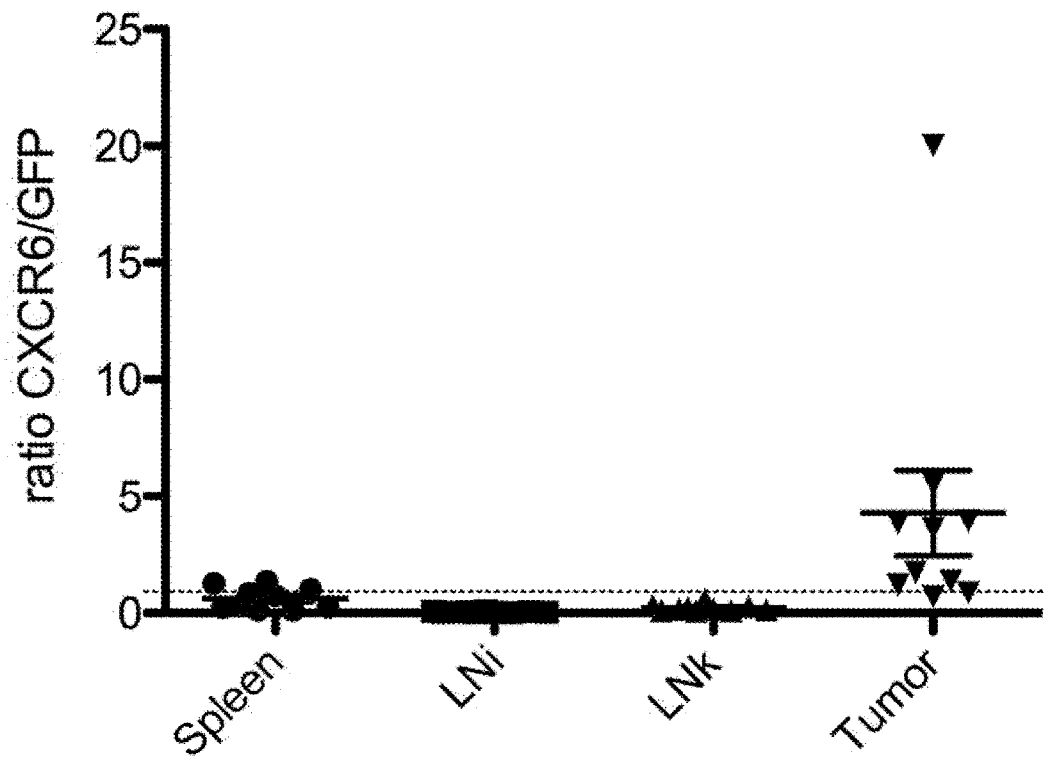

FIG. 19: Quantification of tumor-infiltrating iRFP (Red Fluorescent Protein)—or CXCR6-transduced OT-1 T cells by flow cytometry.

Female C57BL/6J Mice (Janvier, Frankreich (Cat. Number 2014-07-DE-RM-20) were injected with Panc02-OVA tumor cells ($2 \times 10^6$/mice) subcutaneously. After 5 days, T cells were adoptively transferred through the tail vein ($10 \times 10^6$ cells per mice). Organs and tumors were isolated and processed on day 10 of induction (five days after T cell transfer). For flow cytometric analysis, cells were stained with Pacific Blue-conjugated anti-mouse CD8a (clone 53-6.7, BioLegend, San Diego, Calif., USA) and analyzed with counting beads (Life Techonologies, Carlsbad, Calif., USA) for quantification. FIG. 19 demonstrates a specific enrichment of CXCR6 transduced T cells over iRFP transduced T cells.

FIG. 20: CXCL16 secretion by human pancreatic cancer cells

Tumor cells, i.e. human pancreatic cancer cell lines PA-TU-8988T (DSM ACC 162), SUIT-2 clone7 (Iwamura et al., Jpn J Cancer Res 78(1) (1987), 54-62), MIA PaCa-2 (ATCC® CRM-CRL-1420™), and PANC-1 (ATCC® CRM-CRL-1420™) were seeded in a 6-well plate (flat bottom) at a concentration of $0.2 \times 10^6$/well. Supernatants were harvested after 72 hours. Human CXCL16 secretion was measured with a hCXCL16 ELISA kit (R&D Systems, Inc., MN, USA). As shown in FIG. 19, the human pancreatic cancer cell lines PA-TU-8988T (DSM ACC 162), SUIT-2 clone7 (Iwamura et al., Jpn J Cancer Res 78(1) (1987), 54-62), MIA PaCa-2 (ATCC® CRM-CRL-1420™), and PANC-1 (ATCC® CRM-CRL-1420™) release hCXCL16.

Figure 21:
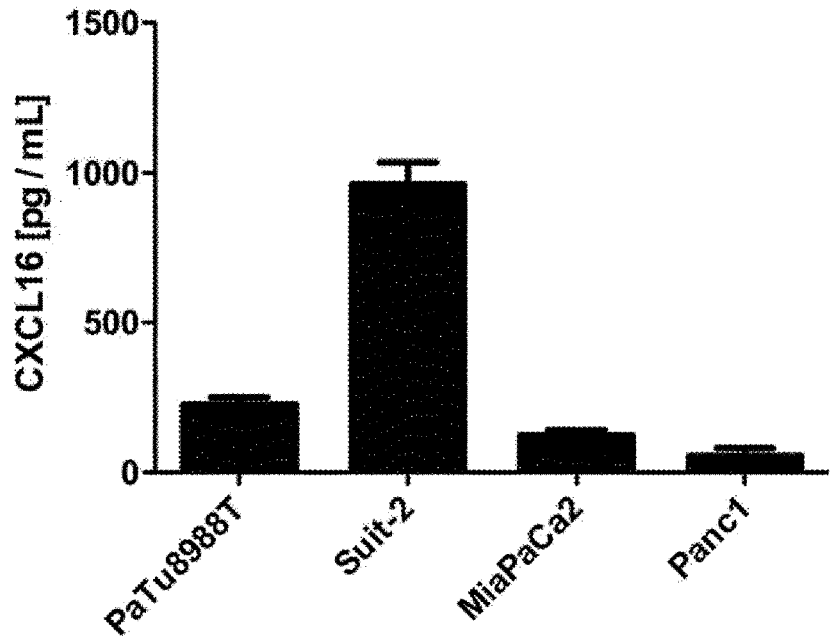

FIG. 21: Sphere formation by human pancreatic cancer cells 96-well plates (flat bottom) were coated with 1.5% agarose. Human pancreatic cancer cell lines PaTu8988T, Suit-2 clone7, MiaPaCa2 and Panc1 (100 and 500 cells/well) were seeded in the agarose-coated 96-well plate (flat bottom). The formation of spheres was observed by PaTu8988T, Suit-2 clone7, MiaPaCa2 and Panc1 tumor cells. Supernatants were harvested after nine days and human CXCL16 production was measured with an hCXCL16 ELISA kit (R&D Systems, Inc., MN, USA).

Figure 22:
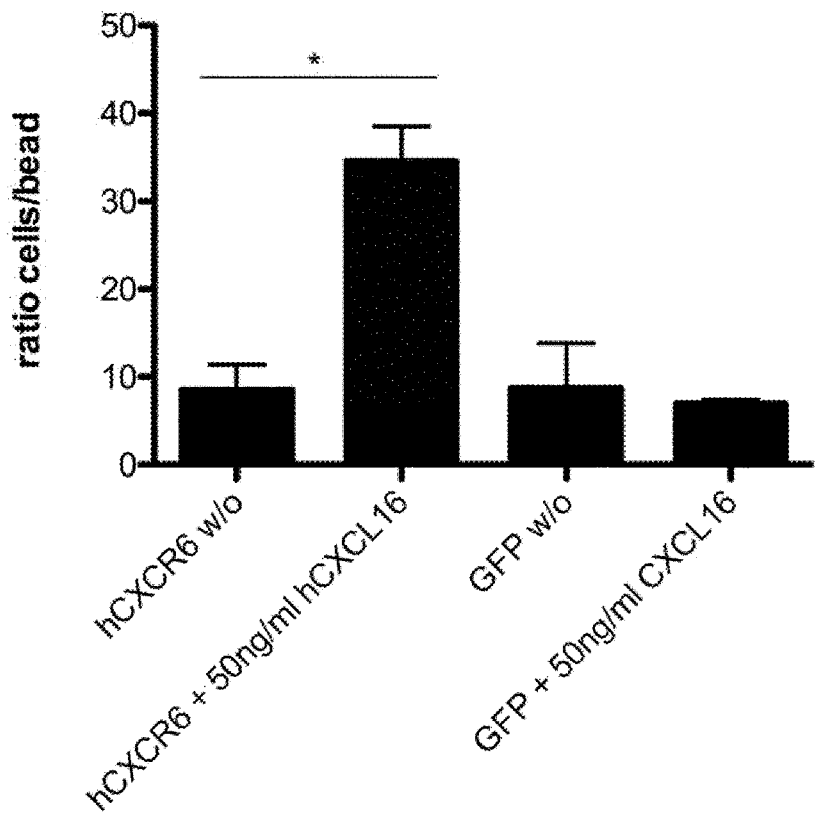

FIG. 22: Migration of CXCR6-transduced human T cells towards recombinant hCXCL16

CXCR6-transduced CD8+ human T cells and GFP-transduced CD8+ human T cells were compared for their ability to migrate towards hCXCL16. Migration medium (0.5% BSA in RPMI medium) was used with or without recombinant hCXCL16 (50 ng/ml) (Peprotech, Hamburg) in the lower chamber and T cells in the upper chamber ($1 \times 10^6$ cells/well) of a 96-transwell plate. After 3 hours migrated T cells were resuspended with counting beads (Life Techonologies, Carlsbad, Calif., USA) for quantification. Migratory capacity was analyzed as cell number and GFP expression by flow cytometry (BD FACS Canto II). As shown in Figure X, CXCR6-transduced human T cells specifically migrate towards hCXCL16, which is not seen with GFP-transduced T cells. P-values are depicted in the Figure, * indicates p<0.05.

THE FOLLOWING EXAMPLES ILLUSTRATE THE INVENTION

Illustratively, as proof of the concept, in the following Examples, the experiments were carried by vector constructs harbouring the mouse/murine sequences of CXCR6 (SEQ ID NO: 3 (cDNA sequence encoding the protein sequence as shown in SEQ ID NO: 4)) and CXCL16 (SEQ ID NO: 7 (cDNA sequence encoding the protein sequence as shown in SEQ ID NO: 8)). Further, in the experiments as exemplified in FIGS. 20 and 21 vector constructs encoding the human sequences of CXCR6 (SEQ ID NO: 1 encoding the protein sequence as shown in SEQ ID NO: 2) was used.

Example 1: Generation of the CXCR6 Vector Construct and the GFP Control Vector Construct The CXCR6 vector capable of transducing CD8+ T cells was generated by amplification of the full length murine CXCR6 sequence (SEQ ID NO: 3) and cloned into the pMP71-vector (Schambach et al., Mol Ther 2(5) (2000), 435-45; EP-B1 0 955 374) after EcoRI and NotI double digestion and ligation. The GFP vector capable of transducing CD8+ T cells was generated by amplification of the full length GFP sequence (SEQ ID NO: 11 (cDNA) and SEQ ID NO: 12 (protein)) and cloned into the pMP71-vector after EcoRI and NotI double digestion and ligation. Cloning was done using polymerase chain reaction from splenocyte cDNA and amplification of CXCR6 corresponding to the above mentioned sequence and the following primers: 5-ATTAGCGGCCGCATGGATGATGGCCATCAGG-3' (SEQ ID NO: 13) and 5'-GGAAACCACCAG-CATGTTTCAGGAATTC-3' (SEQ ID NO: 14). The vector CXCR6GFP was generated in the same way as described above with regard to the CXCR6 and the GFP vector. In brief, the murine full length murine CXCR6 sequence (SEQ ID NO: 3) and the full length GFP sequence (SEQ ID NO: 11 (cDNA) and SEQ ID NO: 12 (protein)) was cloned into the pMP71-vector. The construction of the CXCR6 vector capable of transducing human CD8+ T cells was done in the same way as described above with regard to the CXCR6 vector harbouring the full length murine CXCR6 sequence. In brief length human CXCR6 sequence (SEQ ID NO: 1) was cloned into the pMP71-vector.

Example 2: Transduction of T Cells and Assay Systems for the CXCL16 Secretion, T Cell Proliferation and Killing Assays 2.1 Cell Lines The murine pancreatic cancer cell line Panc02 and its ovalbumin-transfected counterpart Panc02-OVA have been previously described (Jacobs et al., Int J Cancer 128(4) (2011), 897-907). The Panc02-cell line was generated through injection of the carcinogen Methycholantren A into the pancreas of wild type C57Bl/6 mice to induce carcinogenesis.

The tumor cell line T110299 was developed from a primary pancreatic tumor of a Ptf1aCre; KrasG12D; p53fl/R172H mouse 25 and is described in Duewell et al., Cell Death Differ 21(12) (2014), 1825-1837 (Erratum in: Cell Death Differ. 21(12) (2014), 161). The packaging cell line Plat-E has been previously described by Morita et al., Gene Ther 7 (2000), 1063-6). All cells were cultured in DMEM with 10% fetal bovine serum (FBS, Life Technologies, USA), 1% penicillin and streptomycin (PS) and 1% L-glutamine (all from PAA, Germany). 10 µg/ml puromycin and 1 µg/ml blasticidin (Sigma, Germany) were added to the Plat-E medium.

Bone marrow derived dendritic cells were isolated from a C57BL/6J mouse (Janvier, France (Cat. Number 2014-07-DE-RM-20)). Bone marrow cells were cultured with recombinant GM-CSF (20 ng/ml) (Peprotech, Hamburg) for seven days. Bone marrow derived dendritic cells (BM-DC, $10^4$ per well) were seeded in a 96-well plate (flat bottom) and stimulated with recombinant proteins (20 ng/ml) (TNF-α, IFN-γ or IL-4, Peprotech, Hamburg; or R848 Enzo Life Science, Lörrach).

OT-1 T cells are T cells from OT-1 mice Stock number 003831. These OT-1 T cells were produced as follows. Primary splenocytes were harvested from OT-1-mice. Single cell suspensions of splenocytes were stimulated with anti-CD3 (clone 145-2c11 BD Pharmingen, USA), anti-CD28 (clone 37.51, BD Pharmingen, USA) and recombinant murine IL-2 (Peprotech, Germany) in T cell medium over night.

The human pancreatic cancer cell line PA-TU-8988T is obtainable from the cell line depository Leibniz Institute DSMZ-German Collection of Microorganisms and Cell Cultures under the accession number DSM ACC 162. The origin of the deposited cell line PA-TU-89988T is human (*Homo sapiens*). The cell type is pancreas adenocarcinoma. More precisely, the cell line PA-TU-8988T was established in 1985 from the liver metastasis of a primary pancreatic adenocarcinoma from a 64-year-old woman; sister cell line of PA-TU-8988S (DSM ACC 204).

The human pancreatic cancer cell line MIA PaCa-2 is obtainable from the American Type Culture Collection (ATCC) under the accession number CRM-CRL-1420™. The organism of the deposited cell line MIA PaCa-2 is human (*Homo sapiens*). The cell type is epithelial cell (Kras Crm).

The human pancreatic cancer cell line PANC-1 is obtainable from the American Type Culture Collection (ATCC) under the accession number CRL-1469™. The organism of the deposited cell line PANC-1 is human (*Homo sapiens*). The tissue is pancreas/duct.

The human pancreatic cancer cell line SUIT-2 has been previously described in Iwamura et al., Jpn J Cancer Res. 78(1) (1987), 54-62. The pancreatic cancer cell line SUIT-2 is characterized by producing carcinoembyronic antigen and carbohydrate antigen 19-9.

2.2 Animals

Wild type C57Bl/6 mice were bought from Harlan laboratories (The Netherlands). Mice transgenic for a T cell receptor specific for ovalbumine (OT-1) were obtained from the Jackson laboratory, USA (Stock number 003831) and were bred in our animal facility under specific-pathogen free (SPF) conditions. OT-1 mice were crossed to CD45.1 congenic marker mice (obtained from the Jackson laboratory, stock number 002014) and to CD90.1 congeneic marker mice (Stock number: 000406) to generate CD45.1-OT-1 and CD90.1-OT-1 mice, respectively. Wild type C57Bl/6 mice were purchased from Janvier, France. Tumors were induced by subcutaneous injection of $2 \times 10^6$ tumor cells and mice were treated by i.v. injection of T cells as indicated. All experiments were randomized and blinded. For neutralization experiments, anti-IFN-γ antibody R4-6A2 (BioXcell, USA) or isotype control (BioXcell, USA) was applied i.p. at a dose of 200 µg per animal every three days for four doses. Tumor growth and condition of mice were monitored every other day.

2.3 T Cell Transduction 2.3.1 T Cell Transduction of Murine/Mouse T Cells

The retroviral vector pMP71 (Schambach et al., Mol Ther 2(5) (2000), 435-45; EP-B1 0 955 374) was used for transfection of the ecotrophic packaging cell line Plat-E. Transduction was performed according to the method described by Leisegang et al. J Mol Med 86 (2008), 573; Mueller et al. J Virol 86 (2012), 10866-10869; Kobold et al., J Natl Cancer Inst 107 (2015), 364. In brief, packaging cell line Plat E (as described by Morita et al. Gene Ther 7 (2000), 1063) was seeded in 6-well plates and grown over night to 70-80% confluence. On day one, 16 µg of DNA were mixed together with 100 mM CaCl2 (Merck, Germany) and 126.7 µM Chloroquin (Sigma, USA). Plat-E cells were starved for 30 min in low serum medium (3%) and then incubated for 6 h with the precipitated DNA. Medium was then removed and exchanged with culture medium. On day two, primary splenocytes were harvested from C57Bl/6 mice (Janvier). Single cell suspensions of splenocytes were stimulated with anti-CD3 (clone 145-2c11 BD Pharmingen, USA), anti-CD28 (clone 37.51, BD Pharmingen, USA) and recombinant murine IL-2 (Peprotech, Germany) in T cell medium over night. On day 3, 24-well plates were coated with 12.5 µg/ml recombinant retronectin (Takara Biotech, Japan) for 2 h at room temperature, blocked with 2% bovine serum albumin (Roth, Germany) for 30 min at 37° C. and washed with PBS. Supernatant of Plat-E was harvested and passed through a filter (40 µm, Milipore, USA). Fresh T cell medium was then added to Plat E cells. 1 ml of filtered supernatant was distributed in each well and spinoculated for 2 hours at 4° C. Supernatant was then removed from the 24-well plate. $10^6$ T cells were seeded in one ml T cell medium supplemented with 10 U IL-2 and 400,000 anti-CD3 and anti-CD28 beads (Invitrogen, Germany) per well and spinoculated at 800 g for 30 min at 32° C. On day four, Plat E supernatant was again harvested and filtered. 1 ml was added to each well of the 24-well plate and spinoculated at 800 g for 90 min at 32° C. Cells were subsequently incubated for 6 additional hours at 37° C. 1 ml supernatant was replaced by T cell medium with IL-2. On day five, cells were harvested, counted and reseeded at $10^6$ cells/ml density in T cell medium supplemented with 10 ng IL-15 per ml (Peprotech, Germany). T cells were kept at this density until day 10 when cell analysis or functional assays were performed.

Transduction with the retroviral vector pMX (de Witte et al., J. Immunol. 181 (2008), 5128-5136) was performed in the same way as transduction with the vector pMP71 as described above.

2.3.2 Human T Cell Transduction

The retroviral vector pMP71 (Schambach et al., Mol Ther 2(5) (2000), 435-45; EP-B1 0 955 374) was used for transfection of the amphotrophic packaging cell line Plat-A. Transduction was performed according to the method described by Leisegang et al. J Mol Med 86 (2008), 573; Mueller et al. J Virol 86 (2012), 10866-10869; Kobold et al., J Natl Cancer Inst 107 (2015), 364. In brief, packaging cell line Plat A (as described by Morita et al. Gene Ther 7 (2000), 1063) was seeded in 6-well plates and grown over night to 70-80% confluence. On day two, Plat A cells were transfected with the calcium phosphate precipitation method with 18 µg of retroviral vector plasmid pMP71 and then incubated for 6 h. Medium was then removed and exchanged with culture medium. Furthermore, primary PBMCs were isolated and CD3+ T cells were separated by MACS sorting (Miltenyi Biotec, Bergisch Gladbach). CD3+ human T cells were stimulated with anti-human CD3 (clone UCHT1 BD Pharmingen, USA), anti-human CD28 (clone CD28,2, BD Pharmingen, USA), recombinant IL-15 (Peprotech, Germany) and recombinant murine IL-2 (Peprotech, Germany) in T cell medium over night. On day four, 24-well plates were coated with 12.5 µg/ml recombinant retronectin (Takara Biotech, Japan) for 2 h at room temperature, blocked with 2% bovine serum albumin (Roth, Germany) for 30 min at 37° C. and washed with PBS. Supernatant of Plat-A was harvested and passed through a filter (0.45 µm, Milipore, USA). Fresh T cell medium was then added to Plat A cells. 1 ml of filtered supernatant was distributed in each well and spinoculated for 2 hours at 4° C. Supernatant was then removed from the 24-well plate. $10^6$ human T cells were seeded in one ml T cell medium supplemented with IL-2, IL-15 and anti-human CD3 and anti-human CD28 Dynabeads (Invitrogen, Germany) per well and spinoculated at 800 g for 30 min at 32° C. On day five, Plat A supernatant was again harvested and filtered. 1 ml was distributed in each well and spinoculated for 2 hours at 4° C. Supernatant was removed and the infected T cells from the previous day were transferred in the 24-well plate and spinoculated at 800 g for 90 min at 32° C. Cells were subsequently incubated for 6 additional hours at 37° C. After incubation, cells were harvested, counted and reseeded at $10^6$ cells/ml density in T cell medium supplemented with IL-15 and IL-2 (Peprotech, Germany). T cells were kept at this density until day 10 when cell analysis or functional assays were performed.

2.4 Co-Culture of Tumor Cells with T Cells

T cells and tumor cells were co-cultured for 48 h at a ratio of 1:1 or 10:1 in the culture conditions described above. Supernatants were analyzed for IFN-γ by ELISA (BD) as described in section 2.5, infra.

2.5 Lytic Activity of CXCR6-Transduced T Cells in the Presence of CXCL16-Producing Tumor Cells LDH release was measured by a commercial kit (Promega). In brief, LDH catalyzes the reduction of $NAD^+$ to NADH and $H^+$ by oxidation of lactate to pyruvate. Next, diaphorase reacts with NADH and $H^+$ to catalyze the reduction of a tetrazolium salt (INT) to formazan which absorbs at 490 nm.

IFN-γ is measured by ELISA using complementary IFN-γ binding antibodies as capture and as detection antibodies and Horse Radish Peroxidase coupled secondary system.

Cells expressing GFP are analyzed by a flow cytometer and GFP is excited by the 488 nm and detected in the 530 nm filter using a BD FACS Canto II Migration towards CXCL16 was performed using a standard transwell migration where the upper and lower part of the well are separated by commercial porous membranes, which can be passed by T cells. CXCL16 was added to the lower part of the well and the cells in the upper part. If the cells express CXCR6, they will migrate through the pores and can be measured by flow cytometry thereafter.

2.6 Statistical Analysis

For statistics, GraphPad Prism software version 5.0b was used. All variables reported are continuous. Differences between experimental conditions were analyzed using the unpaired two-sided Student's t-test. For comparison of experimental conditions of individual mice, the Mann-Whitney test was used. p-values<0.05 were considered significant. For in vivo experiments, differences between groups were analyzed using two-way ANOVA with correction for multiple testing by the Bonferroni method.

Differences in Panc02-OVA tumor growth in mice were analyzed by comparing tumor surface (defined as the width times the height of a tumor as measured by an analogue caliper) at each time point using two-way ANOVA with correction for multiple testing.

3. Examples of Particular Embodiments

Examples of certain non-limiting embodiments of the disclosure are listed hereafter. In particular, the present invention relates to the following items:

1. A vector capable of transducing T cells comprising a nucleic acid sequence selected from the group consisting of:
   (a) a nucleic acid sequence of SEQ ID NO: 1 or SEQ ID NO: 3, and
   (b) a nucleic acid sequence which is at least 84%, 85%, 86%, 87%, 88%, 89%, 90%, 91%, 92%, 93%, 94%, 95%, 96%, 97%, 98% or 99% identical to the sequence of SEQ ID NO: 1 or SEQ ID NO: 3 and which is characterized by having a chemokine receptor 6 (CXCR6) activity.
2. The vector of item 1, wherein said vector is an expression vector.
3. The vector of item 1 or item 2, wherein said vector is a retroviral vector.
4. The vector of any one of item 1 to 3, wherein said vector further comprises a regulatory sequence which is operably linked to said nucleic acid sequence of item 1.
5. A transduced T cell expressing a chemokine receptor 6 (CXCR6) encoded by a nucleic acid sequence selected from the group consisting of:
   (a) a nucleic acid sequence of SEQ ID NO: 1 or SEQ ID NO: 3, and
   (b) a nucleic acid sequence which is at least 84%, 85%, 86%, 87%, 88%, 89%, 90%, 91%, 92%, 93%, 94%, 95%, 96%, 97%, 98% or 99% identical to the sequence of SEQ ID NO: 1 or SEQ ID NO: 3 and which is characterized by having a chemokine receptor 6 (CXCR6) activity.
6. The transduced T cell of item 5, wherein the chemokine receptor 6 (CXCR6) is stably integrated into the genome of the T cell.
7. The transduced T cell of item 5 or item 6, wherein the chemokine receptor 6 (CXCR6) or a fragment thereof is expressed on the surface of the T cell.
8. The transduced T cell of any one of items 5 to 7, wherein the transduced T cell is co-transduced with a T cell receptor.
9. A method for the production of a transduced T cell expressing a chemokine receptor 6 (CXCR6) comprising the following steps:
   (a) transducing a T cell with a vector comprising a nucleic acid sequence selected from the group consisting of:
      (i) a nucleic acid sequence of SEQ ID NO: 1 or SEQ ID NO: 3, and
      (ii) a nucleic acid sequence which is at least 84%, 85%, 86%, 87%, 88%, 89%, 90%, 91%, 92%, 93%, 94%, 95%, 96%, 97%, 98% or 99% identical to the sequence of SEQ ID NO: 1 or SEQ ID NO: 3 and which is characterized by having a chemokine receptor 6 (CXCR6) activity;
   (b) culturing the transduced T cell under conditions allowing the expression of the chemokine receptor 6 (CXCR6) in or on said T cell; and
   (c) recovering the transduced T cell from the culture.
10. The method of item 9, wherein the transduced T cell is expanded after the transfection by anti-CD3 and anti-CD28 antibodies.
11. The method of item 9 or item 10, wherein the expansion of the transduced T cells is performed in the presence of cytokines, preferably interleukin-2 (IL-2) and/or interleukin-15 (IL-15).
12. A transduced T cell expressing a chemokine receptor 6 (CXCR6) as obtainable by the method of any one of items 9 to 11.
13. The transduced T cell of any one of items 5 to 8 or 12, or obtainable by the method of any one of items 9 to 11 for use as a medicament.
14. The transduced T cell of any one of items 5 to 8, 12 or 13, or obtainable by the method of any one of items 9 to 11 for use in a method of treating a disease characterized by CXCL16 overexpression.
15. A pharmaceutical composition comprising a transduced T cell expressing a chemokine receptor 6 (CXCR6) encoded by a nucleic acid sequence selected from the group consisting of:
   (a) a nucleic acid sequence of SEQ ID NO: 1 or SEQ ID NO: 3, and
   (b) a nucleic acid sequence which is at least 84%, 85%, 86%, 87%, 88%, 89%, 90%, 91%, 92%, 93%, 94%, 95%, 96%, 97%, 98% or 99% identical to the sequence of SEQ ID NO: 1 or SEQ ID NO: 3 and which is characterized by having a chemokine receptor 6 (CXCR6) activity.

16. The pharmaceutical composition of item 15, wherein the transduced T cell comprises the vector of any one of items 1 to 4.

17. The pharmaceutical composition of item 15 or item 16, wherein the transduced T cell is a T cell that has originally been obtained from the patient to be treated with.

18. The pharmaceutical composition of any one of items 15 to 17, wherein the transduced T cell are expanded after transfection by anti-CD3 and anti-CD28 antibodies.

19. The pharmaceutical composition of item 18, wherein the expansion of the transduced T cells is performed in the presence of cytokines, preferably interleukin-2 (IL-2) and/or interleukin-15 (IL-15).

20. The pharmaceutical composition of any one of items 15 to 19 for use in a method of treating a disease characterized by CXCL16 overexpression.

21. A method for the treating of a disease characterized by CXCL16 overexpression in a subject comprising the steps of
    (a) isolating T cells from a subject;
    (b) transducing said isolated T cells with a vector comprising a nucleic acid sequence selected from the group consisting of:
        (i) a nucleic acid sequence of SEQ ID NO: 1 or SEQ ID NO: 3, and
        (ii) a nucleic acid sequence which is at least 84%, 85%, 86%, 87%, 88%, 89%, 90%, 91%, 92%, 93%, 94%, 95%, 96%, 97%, 98% or 99% identical to the sequence of SEQ ID NO: 1 or SEQ ID NO: 3 and which is characterized by having a chemokine receptor 6 (CXCR6) activity; and
    (c) administering said transduced T cells to said subject.

22. The method of item 21, wherein said transduced T cells are administered to said subject by intravenous infusion.

23. The method of item 21 or item 22, wherein said transduced T cells are expanded by anti-CD3 and anti-CD28 antibodies.

24. The method of item 23, wherein the expansion of the transduced T cells is performed in the presence of cytokines, preferably interleukin-2 (IL-2) and/or interleukin-15 (IL-15).

25. The transduced T cell of item 14 for use according to item 14, the pharmaceutical composition of item 20 for use according to item 20, or the method of any one of items 21 to 24, wherein said disease is selected from the group consisting of colorectal cancer, brain cancer, ovarian cancer, prostate cancer, pancreatic cancer, breast cancer, renal cancer, nasopharyngeal carcinoma, hepatocellular carcinoma, gastric cancer, cervical cancer, bladder cancer, lymphoma, sarcoma, and lung cancer.

26. A kit for incorporating a nucleic acid sequence selected from the group consisting of:
    (a) a nucleic acid sequence of SEQ ID NO: 1 or SEQ ID NO: 3, and
    (b) a nucleic acid sequence which is at least 84%, 85%, 86%, 87%, 88%, 89%, 90%, 91%, 92%, 93%, 94%, 95%, 96%, 97%, 98% or 99% identical to the sequence of SEQ ID NO: 1 or SEQ ID NO: 3 and which is characterized by having a chemokine receptor 6 (CXCR6) activity into a T cell comprising a vector of any one of items 1 to 4.

27. The vector of any one of items 1 to 4, the transduced T cell of any one of items 5 to 8, 10, 12, or 13, the method of any one of items 9 to 11, the transduced cell for the use according to any one of items 13 or 14, the pharmaceutical composition of any one of items 15 to 20, the method of any one of items 21 to 25, or the kit of item 26, wherein the T cell is a T cell selected from the group consisting of a CD8+ T cell, CD4+ T cell, a γδ T cell and a natural killer (NK) T cells.

28. The vector, the transduced T cell, the method, the pharmaceutical composition, or the kit according to item 27, wherein the T cell is a CD8+ T cell.

---

The invention claimed is:

1. A T cell expressing a chemokine receptor 6 (CXCR6) having the amino acid sequence of SEQ ID NO:2, which T cell is transduced with an expression vector encoding said CXCR6,
   wherein said T cell has anti-tumoral specificity and/or wherein said T cell is co-transduced with a nucleic acid encoding a T cell receptor or a chimeric antigen receptor, said T cell receptor or said chimeric antigen receptor providing said T cell with specificity for a tumor antigen.

2. A pharmaceutical composition comprising the transduced T cell of claim 1.

3. The transduced T cell of claim 1, wherein the transduced T cell is a T cell originally obtained from the patient to be treated.

4. The transduced T cell of claim 1, wherein the T cell is a T cell selected from the group consisting of a CD8+ T cell, CD4+ T cell, a γδ T cell and a natural killer (NK) T cell.

5. The transduced T cell of claim 1, wherein said T cell is co-transduced with a nucleic acid encoding a chimeric antigen receptor, said chimeric antigen receptor providing said T cell with specificity for a tumor antigen.

6. The transduced T cell of claim 1, wherein said vector comprises the nucleic acid sequence of SEQ ID NO: 1.

* * * * *